United States Patent
Subasinghe et al.

(10) Patent No.: US 7,385,066 B2
(45) Date of Patent: Jun. 10, 2008

(54) THIOPHENE SULFOXIMINES, COMPOSITIONS THEREOF, AND METHODS OF TREATING COMPLEMENT-MEDIATED DISEASES AND CONDITIONS

(75) Inventors: Nalin L. Subasinghe, Exton, PA (US); Shelley Ballentine, Lansdale, PA (US); Jeremy M. Travins, Downingtown, PA (US); Ehab M. Khalil, West Chester, PA (US); Farah Ali, Exton, PA (US); Kristi A. Leonard, West Chester, PA (US); Joan M. Gushue, Harleysville, PA (US); Michael Peter Winters, Morgantown, PA (US); Heather Hufnagel, Glenmoore, PA (US); Maxwell David Cummings, Strafford, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/375,503

(22) Filed: Mar. 14, 2006

(65) Prior Publication Data

US 2007/0066667 A1   Mar. 22, 2007

Related U.S. Application Data

(60) Provisional application No. 60/662,518, filed on Mar. 16, 2005.

(51) Int. Cl.
   C07D 333/34   (2006.01)
(52) U.S. Cl. ........................................ 549/66
(58) Field of Classification Search ............. 549/66
   See application file for complete search history.

(56) References Cited

U.S. PATENT DOCUMENTS 4,025,506 A * 5/1977 Hamanaka et al. ......... 540/332
6,683,055 B1   1/2004 Hillen et al.

FOREIGN PATENT DOCUMENTS

WO   WO 00/61574   10/2000
WO   WO 01/98365   12/2001

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/condtions/09/24/alzheimers.drug.ap/indexhtml>.*
PCT International Search Report, dated Jul. 25, 2006, for PCT Int'l. Appln. No. PCT/US2006/009196.
Subasinghe, N.L. et al., "A novel series of potent and selective small molecule inhibitors of the complement component C1s", BioOrganic & Medicinal Chemistry Letters, Oxford, GB, vol. 14, No. 12, Jun. 21, 2004, pp. 3043-3047.

* cited by examiner

*Primary Examiner*—Kamal Saeed
*Assistant Examiner*—Shawquia Young
(74) *Attorney, Agent, or Firm*—Mary Appollina

(57) ABSTRACT

Disclosed are compounds for treating the symptoms of an acute or chronic disorder mediated by the classical pathway of the complement cascade. The compounds are of Formula I

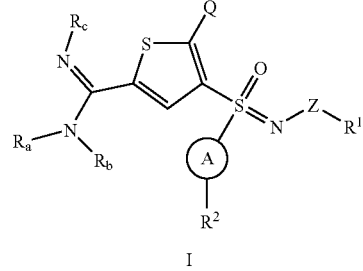

Formula I or a solvate, hydrate, pharmaceutically acceptable salt, or prodrug thereof; wherein $R_a$, $R_b$, and $R_c$ are defined in the specification, as are A Z, Q, $R^1$ and $R^2$.

12 Claims, No Drawings

THIOPHENE SULFOXIMINES, COMPOSITIONS THEREOF, AND METHODS OF TREATING COMPLEMENT-MEDIATED DISEASES AND CONDITIONS

CROSS REFERENCE TO RELATED APPLICATIONS

This application claims priority to U.S. Provisional Application for Patent No. 60/662,518, filed Mar. 16, 2005, the entire disclosure of which are hereby incorporated in their entirely.

BACKGROUND OF THE INVENTION

The present invention is in the field of medicinal chemistry. In particular, the invention is directed to novel heterocyclic sufloximines and their use for inhibiting the enzyme C1s, a protease in the classical pathway of the complement system; and the use of this inhibition to treat or ameliorate acute or chronic disorders in mammals The immune system of the human body is equipped with several defense mechanisms to respond to bacterial, viral, or parasitic infection and injury. One such defense mechanism involves the complement system. Complement consists of a complex series of approximately 30 plasma and membrane protein components, many of which are proteinases. Once activated, this system of enzymes non-specifically complements the immunologically specific effects of antibody by modulating the immune response, lysing target cells, stimulating vascular and other smooth muscle cells, facilitating the transport of immune complexes, producing anaphylatoxins which cause degranulation of mast cells and release of histamine, stimulating chemotaxis (migration) of leukocytes toward the area of complement activity, activating B lymphocytes and macrophages, and inducing phagocytosis and lysis of cells (Eisen, H. N., *Immunology*, Harper & Row Publishers, Inc., Hagerstown, Md., p. 512 (1974); Roitt, I. et al., *Immunology*, Gower Medical Publishing, London, N.Y., pp. 7.1-7.14 (1985); U.S. Pat. Nos. 5,472,939 and 5,268,363).

The complement system functions as a "cascade." The enzyme cascades are initiated when inactive enzyme precursor molecules are activated, through limited proteolysis, by membrane-bound enzymes. A small fragment is lost from the enzyme precursor and a nascent membrane binding site is revealed. The major fragment then binds to the membrane as the next functionally active enzyme of the complement cascade. Since each enzyme is able to activate many enzyme precursors, the system forms an amplifying cascade, resembling the reactions seen in blood clotting and fibrinolysis (Roitt, I. et al., *Immunology*, Gower Medical Publishing, London, N.Y., pp. 7.1-7.14 (1985)).

The proteins of the complement system form three interrelated enzyme cascades, termed the classical, mannan-binding lectin (MBL) and alternative pathways. The classical pathway is usually initiated by antigen-antibody complexes, while the alternative pathway is activated by specific polysaccharides, often found on bacterial, viral, and parasitic cell surfaces. The MBL pathway is mediated by mannan-binding lectin binding to the mannose groups found in many microbial carbohydrates. The classical pathway consists of components C1-C9, while the alternative pathway consists of components C3-C9 (excluding C4) and several factors, such as Factor B, Factor D, and Factor H.

The sequence of events comprising the classical complement pathway consists of three stages: recognition, enzymatic activation, and membrane attack leading to cell death. The first phase of complement activation begins with C1. C1 is made up of three distinct proteins: a recognition subunit, C1q, and the serine proteinase subcomponents, C1r and C1s, which are bound together in a calcium-dependent tetrameric complex, $C1r_2s_2$. An intact C1 complex is necessary for physiological activation of C1 to result. Activation occurs when the intact C1 complex binds to immunoglobulin complexed with antigen. This binding activates C1s which then cleaves both the C4 and C2 proteins to generate C4a and C4b, as well as C2a and C2b. The C4b and C2a fragments combine to form the C3 convertase, which in turn cleaves C3 to form C3a and C3b (Makrides, *Pharmacol. Rev.* 50:59-87 (1998); and U.S. Pat. No. 5,268,363). Both the classical and alternative pathways are capable of individually inducing the production of the C3 convertase to convert C3 to C3b, the generation of which is the central event of the complement pathway. C3b binds to C3b receptors present on neutrophils, eosinophils, monocytes and macrophages, thereby activating the terminal lytic complement sequence, C5-C9 (Roitt, I. et al., *Immunology*, Gower Medical Publishing, London, N.Y., pp. 7.1-7.14 (1985)).

Complement is designed to fight infection and injury; however, this same mechanism, if inappropriately activated, can cause a significant amount of inflammation and tissue damage as a result of the rapid and aggressive enzyme activity. Complement-induced inflammation and tissue damage has been implicated in a number of disease states, including: the intestinal inflammation of Crohn's disease which is characterized by the lymphoid infiltration of mononuclear and polymorphonuclear leukocytes (Ahrenstedt et al., *New Engl. J. Med.* 322:1345-9 (1990)), thermal injury (burns, frostbite) (Gelfand et al., *J. Clin. Invest.* 70:1170 (1982); Demling et al., *Surgery* 106:52-9 (1989)), hemodialysis (Deppisch et al., *Kidney Inst.* 37:696-706 (1990); Kojima et al., *Nippon Jenzo Gakkai Shi* 31:91-7 (1989)), post pump syndrome in cardiopulmonary bypass (Chenoweth et al., *Complement. Inflamm.* 3:152-165 (1981); Chenoweth et al., *Complement* 3:152-165 (1986); Salama et al., *N. Engl. J. Med.* 318:408-14 (1988)), and ischaemia (Huang et al., *Science* 285:595 (1999); Naka et al., *Transplantation* 64:1248 (1997); Pemberton et al., *J. Immunol.* 150:5104 (1993); Chavez-Cartaya et al., *Transplantation* 59:1047 (1995); Hill et al., *J. Immunol.* 149:1723 (1992); Weisman et al., *Science* 249:146 (1990)). Both complement and leukocytes are reported to be implicated in the pathogenesis of adult respiratory distress syndrome (Zilow et al., *Clin. Exp. Immunol.* 79:151-57 (1990); Langlois et al., *Heart Lung* 18:71-84 (1989)). Activation of the complement system is suggested to be involved in the development of fatal complications in sepsis (Hack et al., *Am. J. Med.* 86:20-26 (1989)) and causes tissue injury in animal models of autoimmune diseases such as immune-complex-induced vasculitis (Cochrane, *Springer Seminar Immunopathol.* 7:263 (1984)), glomerulonephritis (Couser et al., *Kidney Inst.* 29:879 (1985)), type II collagen-induced arthritis (Watson & Townes, *J. Exp. Med.* 162:1878 (1985)), and experimental allergic neuritis (Feasby et al., *Brain Res.* 419:97 (1987)). The complement system is also involved in hyperacute allograft and hyperacute xenograft rejection (Knechtle et al., *J. Heart Transplant* 4(5):541 (1985); Guttman, *Transplantation* 17:383 (1974); Adachi et al., *Trans. Proc.* 19(1):1145 (1987)). Complement activation during immunotherapy with recombinant IL-2 appears to cause the severe toxicity and side effects observed from IL-2 treatment (Thijs et al., *J. Immunol.* 144:2419 (1990)).

Complement fragments generated by the classical portion of the complement cascade have been found to be present in the immune complexes formed against indigenous tissue in autoimmune diseases. Such diseases include, but are not limited to: Hashimoto's thyroiditis, glomerulonephritis and cutaneous lesions of systemic lupus erythematosus, other glomerulonephritides, bullous pemphigoid, dermatitis herpetiformis, Goodpasture's syndrome, Graves' disease, myasthenia gravis, insulin resistance, autoimmune hemolyic anemia, autoimmune thrombocytopenic purpura, and rheumatoid arthritis (Biesecker et al. *J. Exp. Med.* 154: 1779 (1981); Biesecker et al., *N. Engl. J. Med.* 306: 264 (1982); Falk et al., *Clin. Research* 32:503A (Abstract) (1984); Falk et al., *J. Clin. Invest.* 72:560 (1983); Dahl et al., *J. Invest. Dermatol.* 82:132 (1984); Dahl et al., *Arch. Dermatol.* 121:70 (1985); Sanders et al. *Clin. Research* 33:388A (Abstract) (1985); and U.S. Pat. Nos. 5,268,363 and 4,722,890).

Compounds that potently and selectively inhibit complement will have therapeutic applications in several acute and chronic immunological and non-immunological disorders, and a variety of neurodegenerative diseases. Evidence from both human and animal studies shows that activation of the classical complement pathway is primarily involved in neurodegenerative diseases of the central nervous system (CNS). Autoimmune diseases in which these inhibitors of the complement cascade system will be therapeutically useful include myasthenia gravis (MG), rheumatoid arthritis, and systemic lupus erythematosus. Neurodegenerative diseases in which inhibitors of the complement cascade system will be therapeutically useful include the demyelinating disorder multiple sclerosis (MS), the neuropathies Guillain-Barré syndrome (GBS) and Miller-Fisher syndrome (MFS), Alzheimer's disease (AD), and prion-related disease (variant Creutzfeld Jacob disease). Other diseases and conditions include hereditary and acquired angioedema (in which a deficiency in complement inhibitory protein leads to an active complement consumption and repeated episodes of life-threatening angiodema), septic shock, paroxysmal nocturnal hemoglobinuria, organ rejection (transplantation), burns (wound healing), brain trauma, soft tissue trauma, asthma, platelet storage, hemodialysis, ischemia-reperfusion injury, and cardiopulmonary bypass equipment (Makrides, *Pharmacol. Rev.* 50:59-87 (1998); Spiegel et al., Strategies for Inhibition of Complement Activation in the Treatment of Neurodegenerative Diseases in: *Neuroinflammation: Mechanisms and Management*, Wood (ed.), Humana Press, Inc., Totowa, N.J., Chapter 5, pp. 129-176; and U.S. Pat. No. 4,916,219).

A number of strategies have been proposed for the inhibition of primarily the classical complement pathway. Efforts to directly inhibit complement activation have focused on chemical compounds that inhibit complement components such as C1r and C1s. Small peptide inhibitors of convertases, such as the C3 and C5 convertases, have also been described (Liszewski and Atkinson, *Exp. Opin. Invest. Drugs* 7: 323-332 (1998). So far, the best studied complement inhibitor for treatment of CNS disorders is soluble recombinant human complement receptor Type 1 (sCR1). sCR1 has proven effective in animal models of CNS diseases and is under investigation for use in man (Fearon, *Clin. Exp. Immunol.* 86 (Suppl. 1): 43-46 (1991)). However, there are several drawbacks to the use of sCR1 in disorders of the CNS: the agent is expensive, must be administered systemically, and has a short half-life in vivo. The next generation of complement inhibitors are likely to solve many of these drawbacks (Spiegel et al., Strategies for Inhibition of Complement Activation in the Treatment of Neurodegenerative Diseases in: *Neuroinflammation: Mechanisms and Management*, Wood (ed.), Humana Press, Inc., Totowa, N.J., Chapter 5, pp. 129-176).

A need continues to exist for non-peptidic compounds that are potent inhibitors of complement, specifically C1s, and which possess greater bioavailability and fewer side-effects than currently available C1s inhibitors. Accordingly, novel C1s inhibitors, characterized by potent inhibitory capacity, are potentially valuable therapeutic agents for a variety of conditions.

SUMMARY OF THE INVENTION

The present invention relates to a racemic or homochiral compound of Formula I:

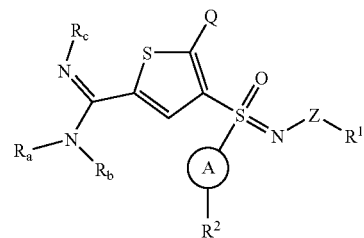

or a solvate, hydrate, pharmaceutically acceptable salt, or prodrug thereof; wherein:

Z is —CO—, —SO$_2$—, —SO$_2$CH$_2$—, —COCH$_2$—, —CONH—, or a direct bond wherein the carbonyl carbon or the sulfur is bonded to the nitrogen;

Q is C$_{1-4}$ alkyl, halo, amino, C$_{1-6}$ alkylthio, C$_{2-6}$ alkenylthio, C$_{1-6}$ alkoxy, trifluoromethyl, methylsulfonyl, or benzylthio;

R$^1$ is hydrogen, C$_{1-4}$ alkyl, aryl, heteroaryl, benzo fused heteroaryl, benzo fused heterocyclyl, any of which except hydrogen is optionally substituted with one or two substituents independently selected from: guanidinyl, halogen, —CF$_3$, —CN, —NO$_2$, —NR$_d$COR$_e$, —CONR$_d$R$_e$, —NR$_d$SO$_2$R$_e$, —SO$_2$NR$_d$R$_e$, —NR$_d$CONHR$_e$, —R$_d$, —NR$_d$R$_e$, —CO$_2$R$_d$, —SO$_2$R$_d$, or heterocyclyl which may be substituted with one R$_d$;

R$^2$ is hydrogen, halogen, aryl or heteroaryl, wherein the aryl or heteroaryl are optionally substituted with up to three substituents independently selected from: C(1-4) alkyl, —NR$_f$R$_g$, guanidinyl;

A is aryl or heteroaryl;

R$_a$, R$_b$ R$_c$, R$_d$ R$_e$, R$_f$ and R$_g$ are independently hydrogen, C$_{1-4}$ alkyl, C$_{6-10}$ aryl, C$_{1-4}$ hydroxyalkyl, C$_{1-4}$ aminoalkyl, mono(C$_{1-4}$)alkylamino(C$_{2-6}$)alkyl, di(C$_{1-4}$)alkylamino(C$_{2-6}$)alkyl, carboxy(C$_{1-4}$)alkyl, cyano, nitro, amino, C$_{1-4}$ alkoxy, hydroxy, or —CO$_2$R$^w$, wherein R$^w$ is hydrogen, hydroxy, C$_{1-4}$ alkoxy, cyano, C$_{1-4}$ alkoxycarbonyl, C$_{1-4}$ alkyl, C$_{3-8}$ cycloalkyl, phenyl, or benzyl.

The present invention provides a novel class of thienyl sulfoximines. The thienyl sulfoximines of Formula I inhibit the enzyme C1s, a protease in the classical pathway of the complement system, and thus, can be used to treat or ameliorate complement-mediated acute or chronic disorders in mammals.

Thus, a first aspect of the present invention is directed to novel compounds of Formula I.

In a second embodiment, the present invention provides a pharmaceutical composition comprising a compound of Formula I and a pharmaceutically acceptable carrier or diluent.

The present invention further provides a method for treating acute and chronic disorders associated with activation of the classical pathway of the complement system by administering to a mammal in need of such treatment a therapeutically effective amount of a compound of Formula I. These acute and chronic conditions are caused either in whole or in part by inflammation and tissue damage that result from aberrant activation of the complement cascade.

In one embodiment, compounds of Formula I can be administered to a mammal to treat complement-mediated inflammation and tissue damage. Examples of conditions that can be treated include intestinal inflammation of Crohn's disease, thermal injury (burns, frostbite), post pump syndrome in cardiopulmonary bypass, and ischaemia (stroke, myocardial infarction, ischaemic colitis, hemorrhagic shock, trauma, post-surgical tissue damage and delayed or impaired function of organ or graft following transplant).

The complement system is activated in hyperacute allograft and hyperacute xenograft rejection, and in acute humoral rejection mediated by donor-specific antibodies. Thus, in yet another embodiment, compounds of Formula I can be administered to a mammal before, during or after the transplant of an organ or a graft to ameliorate the rejection of such organ or graft by the mammal. Grafts can include an allograft or xenograft.

Complement activation during immunotherapy with recombinant IL-2 appears to cause acute vascular leak syndrome that results in the severe toxicity and side effects observed from IL-2 treatment and other conditions such as bone marrow transplantation and acute pancreatitis. In another embodiment of the present invention, a compound of Formula I is administered to a mammal before, during or after treatment of said mammal with IL-2, bone marrow transplantation, or onset of pancreatitis, in an amount effective to reduce the vascular leak syndrome that causes toxicity and side-effects associated with the treatment or disorders.

In another embodiment, compounds of Formula I can be administered to a mammal to treat complement-mediated tissue injury associated with autoimmune diseases. Examples of autoimmune diseases that are treatable according to the present invention include Hashimoto's thyroiditis, Addison's disease, glomerulonephritis and cutaneous lesions of systemic lupus erythematosus, other glomerulonephritides, bullous pemphigoid, pemphigus, Goodpasture's syndrome, Graves' disease, immune-complex-induced vasculitis, hemolytic anemia, myasthenia gravis, allergic neuritis, myasthenia gravis, Type I diabetes mellitus, autoimmune hemolytic anemia, autoimmune thrombocytopenic purpura, type II collagen-induced arthritis, and rheumatoid arthritis. Autoimmune diseases preferred for treatment by inhibitors of the present invention include myasthenia gravis (MG), rheumatoid arthritis, and systemic lupus erythematosus.

Another embodiment of the present invention is directed to administering a therapeutically effective amount of a compound of Formula I to a mammal that has been diagnosed with a neurodegenerative disease. Neurodegenerative diseases in which inhibitors of the complement cascade system will be therapeutically useful include the demyelinating disorder multiple sclerosis (MS), the neuropathies Guillain-Barré syndrome (GBS) and Miller-Fisher syndrome (MFS), Alzheimer's disease (AD), and variant Creutzfeldt-Jakob disease.

In another embodiment, compounds of the present invention can be administered to a mammal to treat complement-mediated complications in sepsis, or symptoms of adult respiratory distress syndrome.

Other diseases and conditions that can be treated include hereditary and acquired angioedema, paroxysmal nocturnal hemoglobinuria, brain trauma and other soft tissue trauma, asthma and hemodialysis.

Compounds of Formula I can also be employed in vitro for human organ and graft storage as well as platelet storage.

DETAILED DESCRIPTION OF THE INVENTION

Compounds useful in the present invention have the general Formula I:

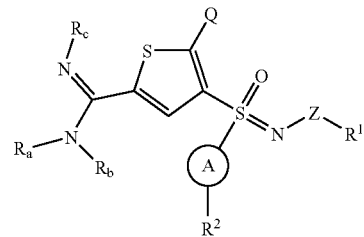

or a solvate, hydrate, pharmaceutically acceptable salt, or prodrug thereof; wherein:

Z is —CO—, —SO$_2$—, —SO$_2$CH$_2$—, —COCH$_2$—, —CONH—, or a direct bond wherein the carbonyl carbon or the sulfur is bonded to the nitrogen;

Q is $C_{1-4}$ alkyl, halo, amino, $C_{1-6}$alkylthio, $C_{2-6}$ alkenylthio, $C_{1-6}$alkoxy, trifluoromethyl, methylsulfonyl, or benzylthio;

$R^1$ is hydrogen, $C_{1-4}$ alkyl, aryl, heteroaryl, benzo fused heteroaryl, benzo fused heterocyclyl, any of which except hydrogen is optionally substituted with one or two substituents independently selected from: guanidinyl, halogen, —CF$_3$, —CN, —NO$_2$, —NR$_d$COR$_e$, —CONR$_d$R$_e$, —NR$_d$SO$_2$R$_e$, —SO$_2$NR$_d$R$_e$, —NR$_d$-CONHR$_e$, —R$_d$, —NR$_d$R$_e$, —CO$_2$R$_d$, —SO$_2$R$_d$, or heterocyclyl which may be substituted with one R$_d$;

$R^2$ is hydrogen, halogen, aryl or heteroaryl, wherein the aryl or heteroaryl are optionally substituted with up to three substituents independently selected from: C(1-4) alkyl, —NR$_f$R$_g$, guanidinyl;

A is aryl or heteroaryl;

$R_a$, $R_b$ $R_c$, $R_d$ $R_e$, $R_f$ and $R_g$ are independently hydrogen, $C_{1-4}$ alkyl, $C_{6-10}$ aryl, $C_{1-4}$ hydroxyalkyl, $C_{1-4}$ aminoalkyl, mono($C_{1-4}$)alkylamino($C_{2-6}$)alkyl, di($C_{1-4}$)alkylamino($C_{2-6}$)alkyl, carboxy($C_{1-4}$)alkyl, cyano, nitro, amino, $C_{1-4}$ alkoxy, hydroxy, or —CO$_2$R$^w$, wherein $R^w$ is hydrogen, hydroxy, $C_{1-4}$ alkoxy, cyano, $C_{1-4}$ alkoxycarbonyl, $C_{1-4}$ alkyl, $C_{3-8}$ cycloalkyl, phenyl, or benzyl.

A preferred group of compounds falling within the scope of the present invention includes compounds of Formula I wherein Q is —SC$_{(1-4)}$alkyl, and A is phenyl.

Another preferred group of compounds falling within the scope of the present invention includes compounds of Formula I wherein $R^1$ is hydrogen, $C_{1-4}$ alkyl, aryl, heteroaryl, benzo fused heteroaryl, benzo fused heterocyclyl, any of which except hydrogen is optionally substituted with one or two substituents independently selected from: guanidinyl, halogen, —$CF_3$, —CN, —$NO_2$, $NR_dCOR_e$, $NR_dSO_2R_e$, $NR_dCONHR_e$, $R_d$, $NH_2$, $CO_2R_e$, $SO_2R_d$, heterocyclyl.

Another preferred group of compounds falling within the scope of the present invention includes compounds of Formula I wherein $R_a$, $R_b$, and $R_c$ are hydrogen, and $R^1$ is selected from hydrogen, $C_{1-4}$ alkyl, phenyl, pyridyl, imidazolyl, thiazolyl, furanyl, thienyl, benzothiazolyl, pyrazolyl, pyrimidinyl, 3,4-Dihydro-2H-benzo[1,4]oxazine, benzimidazolyl, benzofuranyl, indolyl, benzothiophenyl, or 1,3,4oxadiazolyl, any of which except hydrogen is optionally substituted with one or two substituents independently selected from: guanidinyl, halogen, —$CF_3$, —CN, —$NO_2$, $NR_dCOR_e$, $NR_dSO_2R_e$, $NR_dCONHR_e$, $R_d$, $NH_2$, $CO_2R_e$, $SO_2R_d$, heterocyclyl.

Definitions

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2-20 carbon atoms, unless the chain length is limited thereto, wherein there is at least one double bond between two of the carbon atoms in the chain, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably 2 to 8 carbon atoms in length, most preferably 2 to 4 carbon atoms in length.

In all instances herein where there is an alkenyl moiety as a substituent group, the unsaturated linkage, i.e., the vinylene linkage, is preferably not directly attached to a nitrogen, oxygen or sulfur moiety.

The term "alkylthio" as employed herein by itself or as part of another group refers to a straight or branched chain radical of 1 to 20 carbon atoms, unless the chain length is limited thereto, bonded to a sulfur atom, including, but not limited to, methylthio, ethylthio, n-propylthio, isopropylthio, and the like. Preferably the alkylthio chain is 1 to 10 carbon atoms in length, more preferably 1 to 8 carbon atoms in length.

The term "alkoxy" as employed herein by itself or as part of another group refers to a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aralkyl" or "arylalkyl" as employed herein by itself or as part of another group refers to $C_{1-6}$-alkyl groups as discussed above having an aryl substituent, such as benzyl, phenylethyl or 2-naphthylmethyl.

The term "aryl" as employed herein by itself or as part of another group refers to monocyclic or bicyclic aromatic groups containing from 6 to 14 carbons in the ring portion, preferably 6-10 carbons in the ring portion, such as phenyl, naphthyl or tetrahydronaphthyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "dialkylamine" as employed herein by itself or as part of another group refers to an amino group which is substituted with two alkyl groups, each having from 1 to 6 carbon atoms.

The term "enantiomer" as employed herein refers to either of a pair of chemical compounds or salts whose molecular structures have a mirror-image relationship to each other The term "graft" as employed herein by itself or part of another group refers to material, especially living tissue or an organ, surgically attached to or inserted into a bodily part to replace a damaged part or compensate for a defect.

The terms "halogen" or "halo" as employed herein by itself or as part of another group refers to chlorine, bromine, fluorine or iodine, with chlorine being preferred.

The terms "heterocyclic," "heterocyclo" or "heterocycle" as employed herein by themselves or as part of larger groups refer to a saturated or wholly or partially unsaturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Especially useful are rings containing one oxygen or sulfur, one to three nitrogen atoms, or one oxygen or sulfur combined with one or two nitrogen atoms. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, benzofuranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^yR^z$ moiety, wherein $R^y$ and $R^z$ are, independently from one another, hydrogen or $C_1$ to $C_8$ alkyl, or together with the nitrogen to which they are bound, form a saturated or unsaturated 5-, 6-, or 7-membered ring.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, benzofuranyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "homochiral" as employed herein refers to a chemical compound or salt consisting of only one enantiomer.

The term "medical device" as employed herein refers to an instrument, apparatus, implement, machine, contrivance, implant, in vitro reagent, or other similar or related article, including a component part, or accessory which is:

recognized in the official National Formulary, or the United States Pharmacopoeia, or any supplement to them, intended for use in the diagnosis of disease or other conditions, or in the cure, mitigation, treatment, or prevention of disease, in man or other animals, or intended to affect the structure or any function of the body of man or other animals, and which does not achieve any of its primary intended purposes through chemical action within or on the body of man or other animals and which is not dependent upon being metabolized for the achievement of any of its primary intended purposes.

Examples of medical devices include, but are not limited to stents, prostheses, artificial organs, and artificial joints.

The term "monoalkylamine" as employed herein by itself or as part of another group refers to an amino group which is substituted with one alkyl group having from 1 to 6 carbon atoms.

The expression "prodrug" denotes a derivative of a known direct acting drug, which derivative has enhanced delivery characteristics and therapeutic value as compared to the drug, and is transformed into the active drug by an enzymatic or chemical process. Useful prodrugs are those where $R_b$, $R_c$ and/or $R^4$ are —$CO_2R^w$, where $R^w$ is defined above. See U.S. Pat. No. 5,466,811 and Saulnier et al., *Bioorg. Med. Chem. Lett.* 4:1985-1990 (1994).

The term "substituted," as used herein, means that one or more hydrogens of the designated moiety are replaced with a selection from the indicated group, provided that no atom's normal valency is exceeded, and that the substitution results in a stable compound. When a substituent is keto (i.e., =O), then 2 hydrogens attached to an atom of the moiety are replaced.

By "stable compound" or "stable formula" is meant herein a compound that is sufficiently robust to survive isolation to a useful degree of purity from a reaction mixture and formulation into an efficacious therapeutic agent.

The term "stent" refers to any device capable of being delivered by a catheter. A stent is routinely used to prevent vascular closure due to physical anomalies such as unwanted inward growth of vascular tissue due to surgical trauma. It often has a tubular, expanding lattice-type structure appropriate to be left inside the lumen of a duct to relieve an obstruction. The stent has a lumen wall-contacting surface and a lumen-exposed surface. The lumen-wall contacting surface is the outside surface of the tube and the lumen-exposed surface is the inner surface of the tube. The stent can be polymeric, metallic or polymeric and metallic, and it can optionally be biodegradable.

By an "efficacious level" of a composition of the invention is meant a level at which some relief is afforded to the patient who is the recipient of the treatment. By an "abnormal" host inflammatory condition is meant a level of inflammation in the subject at a site which exceeds the norm for the healthy medical state of the subject, or exceeds a desired level. By "secondary" tissue damage or toxic effects is meant the tissue damage or toxic effects which occur to otherwise healthy tissues, organs, and the cells therein, due to the presence of an inflammatory response, including as a result of a "primary" inflammatory response elsewhere in the body.

The "animals" referred to herein are preferably mammals and most preferably humans, although the invention is not intended to be limited to such.

Abbreviations:

| | |
|---|---|
| AcOH | acetic acid |
| AlMe$_3$ | trimethyl aluminum |
| Boc | t-butyloxycarbonyl, also tBoc |
| Boc$_2$O | di-tert-butyl dicarbonate |
| $^t$BuONO | 2-Methyl-2-nitrosooxy-propane |
| m-CPBA | m-chloroperbenzoic acid |
| Cu(OTf)$_2$ | copper(II)trifluoromethanesulfonate |
| DCM | dichloromethane |
| DIEA | diisopropylethylamine |
| DIC | diisopropylcarbonate |
| DME | dimethoxyethane |
| DMAP-resin | 4-dimethylaminopyridine - modified resin |
| DMAP | 4-dimethylaminopyridine |
| DMF | dimethylformamide |
| DMSO | dimethyl sulfoxide |
| DTNB | 5,5'-dithio-bis(2-nitrobenzoic acid) |
| ESI-MS | electrospray ionization mass spectrum |
| Et$_2$O | diethyl ether |
| Et$_3$N | triethylamine |
| EtOAc | ethyl acetate |
| HEPES | 4-(2-hydroxyethyl)piperazine-1-ethanesulfonic acid |
| HPLC | high pressure liquid chromatography |
| LDA | lithium diisopropylamine |
| MeOH | methanol |
| NaOMe | sodium methoxide |
| NaSMe | sodium methanethiolate |
| NMR | nuclear magnetic resonance |
| PCC | pyridinium chlorochromate |
| Pd(dppf)Cl$_2$ | Dichloro(1,1bis(diphenylphosphino)ferrocene)palladium(II) |
| Pd(PPh$_3$)$_4$ | tetrakistriphenylphosphine Pd$^0$ |
| PhI(OAc)$_2$ | iodobenzene diacetate |
| $^i$PrMgCl | isopropylmagnesium chloride |
| RP-HPLC | reverse phase high pressure liquid chromatography |
| RT | room temperature |
| rt | retention time |
| TFA | trifluoroacetic acid |
| TBAF | tetrabutyl ammonium fluoride |
| TEA | triethylamine |
| THF | tetrahydrofuran |
| TLC | thin layer chromatography |

When any variable occurs more than one time in any constituent or in any Formula, its definition on each occurrence is independent of its definition at every other occurrence. Also, combinations of substituents and/or variables are permissible only if such combinations result in stable compounds.

The present invention provides a method for treating acute and chronic disorders associated with activation of the classical pathway of the complement system by administering to a mammal in need of such treatment a therapeutically effective amount of a compound of Formula I.

These acute and chronic conditions include inflammation and tissue damage that arise as a result of rapid and aggressive enzyme activity of the complement cascade. Complement-mediated inflammation and the resultant tissue damage has been implicated in a number of disease states including: 1) ischaemia reperfusion damage, such as occurs post myocardial infarction, post transplant, post surgery and in hemorrhagic shock; 2) antibody-mediated conditions, such as hyperacute allograft and xenograft rejection, organ transplant rejection and auto-immune diseases; and 3) other disease states, such as thermal injury, trauma, adult respiratory distress syndrome (ARDS), sepsis and prion disease.

The compounds of the present invention are believed to inhibit the functioning of the protease activity of C1s. This protease-inhibition activity results in the inhibition or blocking of a variety of complement-mediated immunological functions. Therefore, compounds of Formula I can be used to ameliorate a number of disease states induced by complement-mediated inflammation and tissue damage.

The term "treatment of inflammation" or "treating inflammation" is intended to include the administration of compounds of the present invention to a subject for purposes which can include prophylaxis, amelioration, prevention or cure of an inflammatory response. Such treatment need not necessarily completely ameliorate the inflammatory response. Further, such treatment can be used in conjunction with other traditional treatments for reducing the inflammatory condition known to those of skill in the art.

In one embodiment, compounds of Formula I can be administered to a mammal to treat complement-mediated inflammation and tissue damage that is a consequence of ischaemia/reperfusion injury. Thus, the C1s inhibitors of the present invention can be employed to prevent, or at least ameliorate, inflammation and tissue damage arising from a stroke, myocardial infarction, hemorrhagic shock, and surgery. In particular, compounds of Formula I can be employed to prevent inflammation of transplanted tissue and organs.

The compounds of Formula I can also be provided as a preventive treatment before detection of an inflammatory state, so as to prevent the same from developing in patients at high risk for the same, such as, for example, transplant patients.

The compounds of Formula I can be used to treat chronic or acute inflammation that is the result of an antibody-mediated reaction, such as hyperacute allograft and xenograft rejection, organ transplant rejection and autoimmune diseases, which include arthritis, rheumatoid arthritis, multiple sclerosis (MS), type I diabetes, intestinal inflammation of Crohn's disease, systemic lupus erythematosus (lupus), immune-complex-induced vasculitis, restenosis and psoriasis.

The complement system is activated in hyperacute allograft and hyperacute xenograft rejection, and in acute humoral rejection mediated by donor-specific antibodies. In another embodiment, compounds of Formula I can be administered to a mammal before, during or after the transplant of an organ or a graft to ameliorate the rejection of such organ or graft by the mammal.

Organ transplant and graft patients undergo concurrent immunotherapy. Complement activation during immunotherapy with recombinant IL-2 appears to cause acute vascular leak syndrome that results in the severe toxicity and side effects observed from IL-2 treatment and other conditions such as bone marrow transplantation and acute pancreatitis. Thus, in a further embodiment of the present invention, a compound of Formula I is administered to a mammal before, during or after treatment of said mammal with IL-2, bone marrow transplantation, or onset of pancreatitis, in an amount effective to reduce the vascular leak syndrome that causes toxicity and side-effects associated with the treatment or disorders.

Another embodiment of the present invention is directed to administering a therapeutically effective compound of Formula I to a mammal that has been diagnosed with an autoimmune disease. Autoimmune diseases that are treatable according to the present invention include Addison's disease, Type I diabetes mellitus, Hashimoto's thyroiditis, glomerulonephritis and cutaneous lesions of systemic lupus erythematosus, other glomerulonephritides, bullous pemphigoid, dermatitis herpetiformis, Goodpasture's syndrome, Graves' disease, Parkinson's disease, myasthenia gravis, insulin resistance, autoimmune hemolytic anemia, autoimmune thrombocytopenic purpura, immune-complex-induced vasculitis glomerulonephritis, type II collagen-induced arthritis, rheumatoid arthritis, and allergic neuritis. Autoimmune diseases preferred for treatment by inhibitors of the present invention include myasthenia gravis (MG), rheumatoid arthritis, and systemic lupus erythematosus.

Another embodiment of the present invention is directed to administering a therapeutically effective amount of a compound of Formula I to a mammal that has been diagnosed with a neurodegenerative disease. Neurodegenerative diseases in which inhibitors of the complement cascade system will be therapeutically useful include the demyelinating disorder multiple sclerosis (MS), the neuropathies Guillain-Barré syndrome (GBS) and Miller-Fisher syndrome (MFS), Alzheimer's disease (AD) and variant Creutzfeldt-Jakob disease (vCJD).

In another embodiment, efficacious levels of the C1s inhibitors of the invention are administered so as to provide therapeutic benefits against the secondary harmful inflammatory effects of inflammation.

In an additional embodiment, compounds of the present invention can be administered to a mammal suffering from the symptoms of ARDS. ARDS is a complex pulmonary disorder affecting 150,000 people in the U.S. yearly with a 50% mortality rate. Leukocytes, platelets and the proteolytic pathways of coagulation and complement mediate ARDS. ARDS involves activation of the contact activation pathway and depletion of C1 inhibitor and may be induced by either sepsis or trauma. Sepsis-induced ARDS results in more severe disseminated intravascular coagulation (DIC) and fibrinolysis, more fibrin degradation products and reduced ATIII levels compared to trauma-induced ARDS (Carvalho et al., *J. Lab. Clin. Med.* 112:270-277 (1988)).

In a further embodiment, compounds of Formula I can be administered to a person in septic shock. Septic shock is the most common cause of death of humans in intensive care units in the United States (Parillo et al., *Ann. Int. Med.* 113:227-242 (1990); Schmeichel C. J. & McCormick D., *BioTechnol.* 10:264-267 (1992)). In recent years aggressive fluid infusion therapy has been accepted as a primary means of treatment for septic shock.

The increase in cardiac output and vasodilation in septic shock is attributed to the action of inflammatory mediators. In septic shock, components of the kallikrein-kinin system are depleted, suggesting activation of this system. This is not the case in cardiogenic shock, suggesting that the kallikrein-kinin system is a key player in septic shock (Martinez-Brotons F. et al., *Thromb. Haemostas.* 58:709-713 (1987)). While the actual events leading to septic shock, DIC and hypotension have not been established, the known interactions among various components of the many physiological systems suggest that activation of the contact pathway may lead to a state of septic shock, multi-organ failure, and death (Bone, R. C., *Arch. Intern. Med.* 152:1381-1389 (1992); Colman, R. W., *New Engl. J. Med.* 320:1207-1209 (1989)). The contact activation pathway is also involved in both fibrin deposition and lysis, as well as triggering neutrophil activation, activation of complement and modulation of blood pressure.

Inhibition of the complement cascade is expected to lead to downstream utilities associated with the contact system of coagulation and the complement system. This interaction between components of the complement and coagulation systems at the surface of blood platelets and endothelium can generate inflammatory and chemotactic peptides at sites of vascular thrombus formation and may contribute to the altered hemostasis associated with immune disease states. In addition, immune reactions affecting blood platelets and endothelium can lead to platelet aggregation, the secretion of proteolytic enzymes and vasoactive amines from platelet storage granules, and increase adherence of platelets and leukocytes to the endothelial lining of blood vessels.

Other diseases and conditions that can be treated with compounds of Formula I include hereditary angioedema, paroxysmal nocturnal hemoglobinuria, wound healing, brain trauma, asthma, hemodialysis, infection, dermatosis, inflammatory bowel disease, osteoporosis, osteoarthritis, thermal injury (burns and frostbite), hemolytic anemia and post pump syndrome in cardiopulmonary bypass.

It has been demonstrated that membrane-uptake of C3b and C5b-9 proteins can occur spontaneously during incubation of platelets in citrated plasma. Complement activation can also occur during blood collection as a result of exposure to plastic surfaces supporting the C3-convertase reaction. While the implications of complement activation during blood collection and in vitro storage for transfusion have not been directly addressed, it is nevertheless known that plasma levels of coagulation factors V and VIII rapidly decline in stored platelet concentrates at a rate considerably faster than their decay in cell-free plasma, suggesting consumptive loss. Further, platelet collection and storage is associated with an increase in vesicular plasma membrane microparticles, a product of C5b-9 initiated platelet secretion. These physiological and enzymatic changes greatly reduce the potential shelf life of stored platelets, particularly platelet-rich plasma concentrates used for transfusions, which is generally only 72 hours at best. Furthermore, this interaction of activated C5b-9, platelets, and coagulation factors in stored platelet concentrates will adversely affect the hemostatic effectiveness of these units when infused.

In vitro human organ and tissue storage and survival of the transplanted graft is also adversely affected by the spontaneous activation of the complement system, resulting in membrane insertion of the C5b-9 proteins into vascular endothelium. Activation of C5 to C5a and C5b can be catalyzed by plastics and other synthetic membranes required to maintain perfusion of vascular beds during in vitro tissue and organ storage. In addition, membrane deposition of C5b-9 in vivo has been implicated in the acute rejection of transplanted tissue due to immune activation of the recipient's plasma complement system against the endothelial cells within the donor's organ.

Platelet and endothelial cell activation by C5b-9 also has ramifications in autoimmune disorders and other disease states. The importance of spontaneous complement activation and the resulting exposure of platelets and endothelium to activated C5b-9 to the evolution of vaso-occlusive disease is underscored by consideration that a) leukocyte infiltration of the subendothelium, which is known to occur in regions of atheromatous degeneration and suggests localized generation of C5a at the vessel wall, is potentially catalyzed by adherent platelets; and b) local intravascular complement activation resulting in membrane deposition of C5b-9 complexes accompanies coronary vessel occlusion and may affect the ultimate extent of myocardial damage associated with infarction.

It is therefore an aspect of the present invention to provide a means and method for the modulation and inhibition of complement-mediated platelet and endothelial cell activation in vivo and in vitro. It is a further aspect of the present invention to provide a means and method for increasing the survival and therapeutic efficacy of platelets and tissues or organs collected and stored in vitro.

Preferably, the treatment methods of the invention deliver the C1s inhibitor either by contacting cells of the animal with a C1s inhibitor described above or by administering to the animal a C1s inhibitor described above.

The inhibitors can be used in vitro or in vivo. They can be administered by any number of known routes, including orally, intravenously, intramuscularly, subcutaneously, intrathecally, topically, transdermally, and by infusion (Platt et al., U.S. Pat. No. 4,510,130; Badalamente et al., *Proc. Natl. Acad. Sci. U.S.A.* 86:5983-5987 (1989); Staubli et al., *Brain Research* 444:153-158 (1988)) and will generally be administered in combination with a physiologically acceptable carrier (e.g., physiological saline) or diluent. The effective quantity of inhibitor given will be determined empirically and will be based on such considerations as the particular inhibitor used, the condition of the individual, and the size and weight of the individual. It is to be expected that the general end-use application dose range will be about 0.01 to 100 mg per kg per day, preferably 0.1 to 75 mg per kg per day for an effective therapeutic effect.

Amounts and regimens for the administration of C1s inhibitors and compositions of the invention can be determined readily by those with ordinary skill in the clinical art of treating inflammation-related disorders such as arthritis, tissue injury and tissue rejection. Generally, the dosage of the composition of the invention will vary depending upon considerations such as: type of pharmaceutical composition employed; age; health; medical conditions being treated; kind of concurrent treatment, if any; frequency of treatment and the nature of the effect desired; extent of tissue damage; gender; duration of the symptoms; and contraindications, if any, and other variables to be adjusted by the individual physician. A desired dosage can be administered in one or more applications to obtain the desired results. Pharmaceutical compositions containing the C1s inhibitors of the invention can be provided in unit dosage forms.

In one embodiment, dosing will be by intravenous injection or short-term infusion. In a further embodiment, the C1s inhibitors of the present invention will be administered orally, in the form of a tablet, pill, lozenge, troche or capsule. To achieve optimal therapeutic effect, maintenance dosing may be required. Such maintenance dosing may be given repeatedly during the course of a day by, for instance, repeated individual injections, repeated oral dosing, or by introduction of a continuous drip infusion. Effective dosages can be readily determined by one of ordinary skill in the art through routine trials establishing dose response curves.

Pharmaceutical Compositions

Pharmaceutical compositions for treating a complement-mediated disease state, comprising a compound of Formula I in an amount effective to inhibit C1s protease function in a mammal and a pharmaceutically acceptable carrier or diluent, are within the scope of the present invention.

Pharmaceutical compositions comprising an effective amount of the C1s inhibitors of the invention, in combination with any conventional pharmaceutically acceptable carrier or diluent, are included in the present invention.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of Formula I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, cyclamic acid, pivalic acid and the like; useful inorganic acids are hydrohalide acids such as HCl, HBr, and HI; sulfuric acid; phosphoric acid and the like. Preferred acids for forming acid addition salts include HCl and acetic acid.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations, which can be used orally, include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred salts are hydrochloride and acetate salts. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

When employed as thrombin inhibitors, the compounds of the present invention may be administered in an effective amount within the dosage range of about 0.1 to about 500 mg/kg, preferably between about 0.1 and about 10 mg/kg body weight, on a regimen in single or 2-4 divided daily doses.

Compounds of Formula I may be prepared by a variety of methods. Exemplary synthetic routes for generating sulfoximines of the invention are described below.

EXAMPLE 1a

General Procedure for Preparation of Sulfoximines

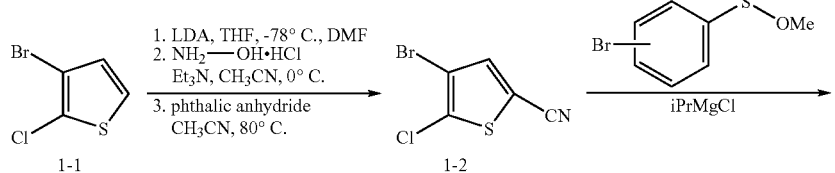

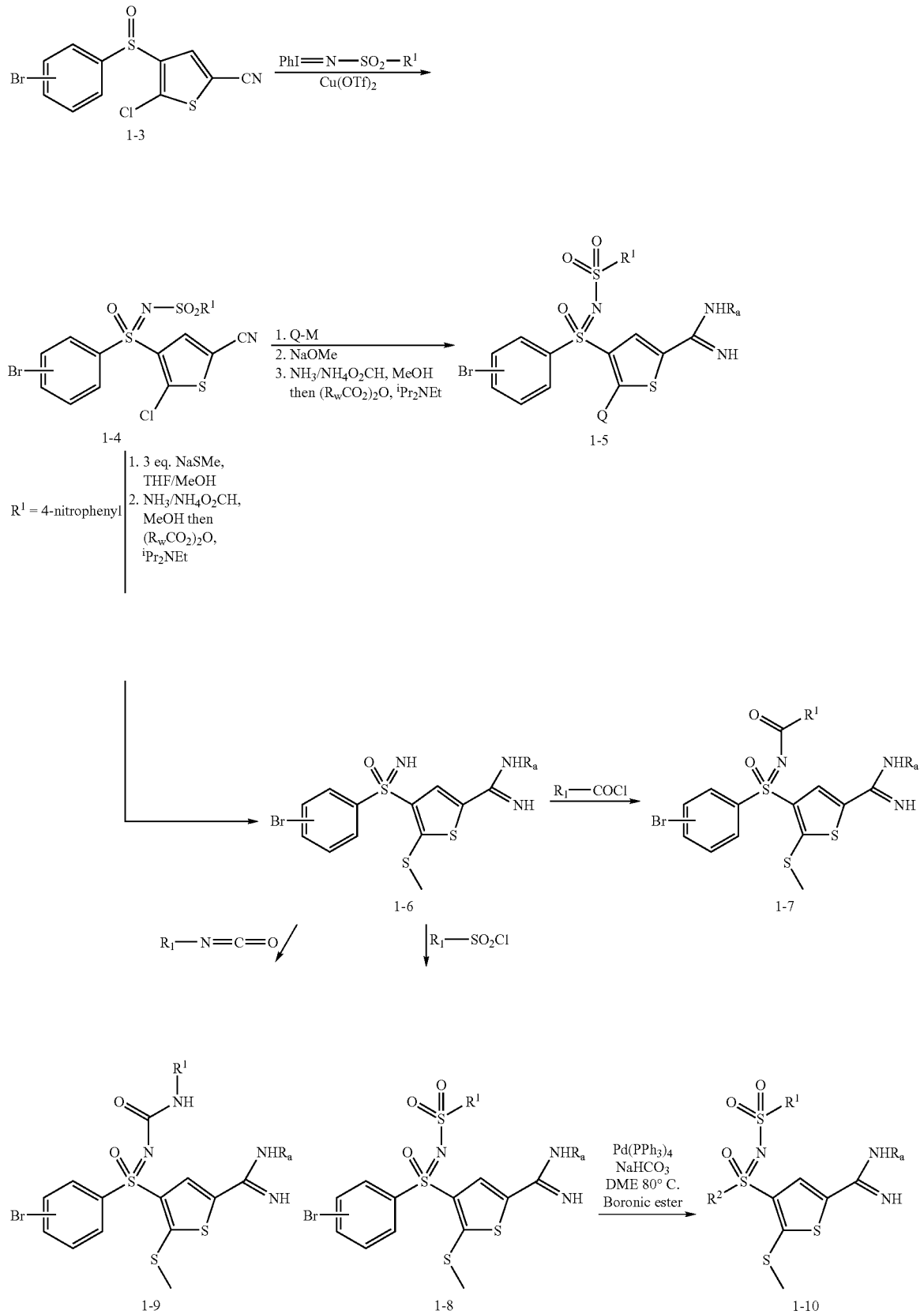

A solution of 3-bromo-2-chloro-thiophene (1-1) is treated with lithium diisopropyl amine (LDA). Formylation with DMF is followed by condensation with hydroxylamine and subsequent water elimination using phthalic anhydride (Wang, E., Lin, G. *Tetrahedron Lett* 39, 4047-4050 (1998)) gives 4-bromo-5-chloro-thiophene-2-carbonitrile (1-2). Treatment with isopropyl magnesium chloride followed by a sulfinic methyl ester, such as meta-bromo benzene sulfinic methyl ester, gives the sulfoxide (1-3) (Andersen, K. K. et al. *J. Am. Chem. Soc.* 86, 5637 (1964)). It is recognized, by those skilled in the art, that different sulfinic esters may be used, such as phenyl, naphthyl, pyridyl, imidazolyl, thiazolyl, furanyl, thienyl, benzothiazolyl, pyrazolyl, pyrimidinyl, benzimidazolyl, benzofuranyl, indolyl, or benzothiophenyl any of which is optionally substituted. Sulfoxide (1-3) is oxidized to sulfoximine (1-4) by a substituted sulfonylimino iodinane. Reactions were carried out in the presence of an aprotic solvent such as acetonitrile, a lewis acid such as copper (II) trifluoromethane sulfonate, under inert atmosphere such as argon or nitrogen, at room temperature (Lacote, E. et al. *Synlett* 2002, 28, 116-118).

Reaction of sulfoximine (1-4) with a nucleophile, Q-M, where M is a metal such as an alkali, allows replacement of the chloro functionality; examples include other halogens, alkyl groups, alkoxides, and alkylthiols. Concomitant conversion of the nitrile to the imidate ester may be observed with certain nucleophiles such as sodium methanethiolate. If simultaneous removal of a para-nitro phenol from a sulfoximine is desired, three equivalents of sodium methanethiolate may be used (Cren, S. et al *Tetrahedron Lett.* 43, 2749-2751 (2002)). Subsequent treatment of the nitrile with sodium methoxide to form the imidate, followed by treatment of the imidate with a solution of methanolic ammonia/ammonium formate reveals the carboxamidine functionality. Protection with tert-butlyoxycarbonyl, or other suitable protecting group gives product (1-5) or, where $R^1$ is removed, product (1-6). Sulfoximine (1-6) may be further reacted with an appropriate electrophile to give products (1-7, 1-8, and 1-9).

Products 1-6 through 1-9 may be further derivatized at the $R^1$, $R^2$, or Q positions, followed by acid mediated removal of the carboxamidine protecting group. Palladium mediated cross coupling with an appropriate boronic ester is an example of $R^1$ derivatization, giving products of formula 1-10.

EXAMPLE 1b

General Synthesis of Sulfonylimino Iodinanes

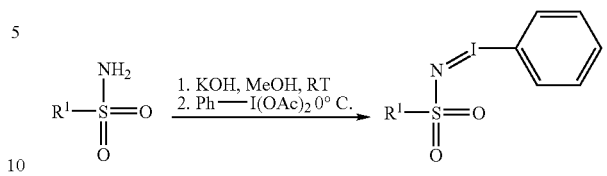

The sulfonylimino iodinane used above was made from the condensation of a sulfonamide with iodobenzene diacetate using a base, such as potassium hydroxide, in a solvent such as methanol at 0° C. (Ronald E. W. et al; *J. Am. Chem. Soc.* 106(17); 4922-4926 (1984)).

EXAMPLE 1c

General Procedure for the Synthesis of Sulfinic Methyl Esters

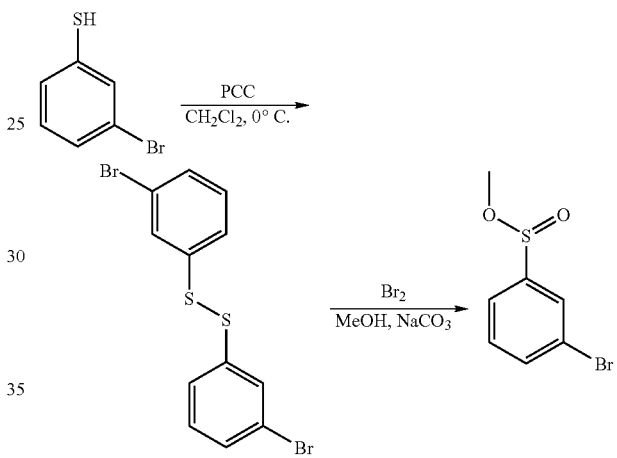

The sulfinic methyl ester used in Example 1a was generated by the oxidation of an aryl thiol, first with PCC (Salehi, P. et al, *Synthetic Communications*, 31(18), 2777-2781 (2001)), and then with bromine. A solution of a bromine substituted benzenethiol is treated with pyridinium chlorochromate to give bis-bromophenyldisulfide. Oxidation with bromine in methanol (Resek, J. E. et al, *Tetrahedron Lett.* 36, 7051-7054 (1995)), followed by aqueous workup, gives bromo-benzenesulfinic acid methyl ester. It is recognized, by those skilled in the art, that different aryl thiols may be used, such as phenyl, naphthyl, pyridyl, imidazolyl, thiazolyl, furanyl, thienyl, benzothiazolyl, pyrazolyl, pyrimidinyl, benzimidazolyl, benzofuranyl, indolyl, or benzothiophenyl any of which is optionally substituted.

EXAMPLE 2

General Procedure for Preparation of Sulfoximines

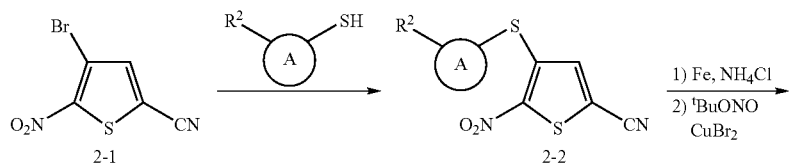

-continued

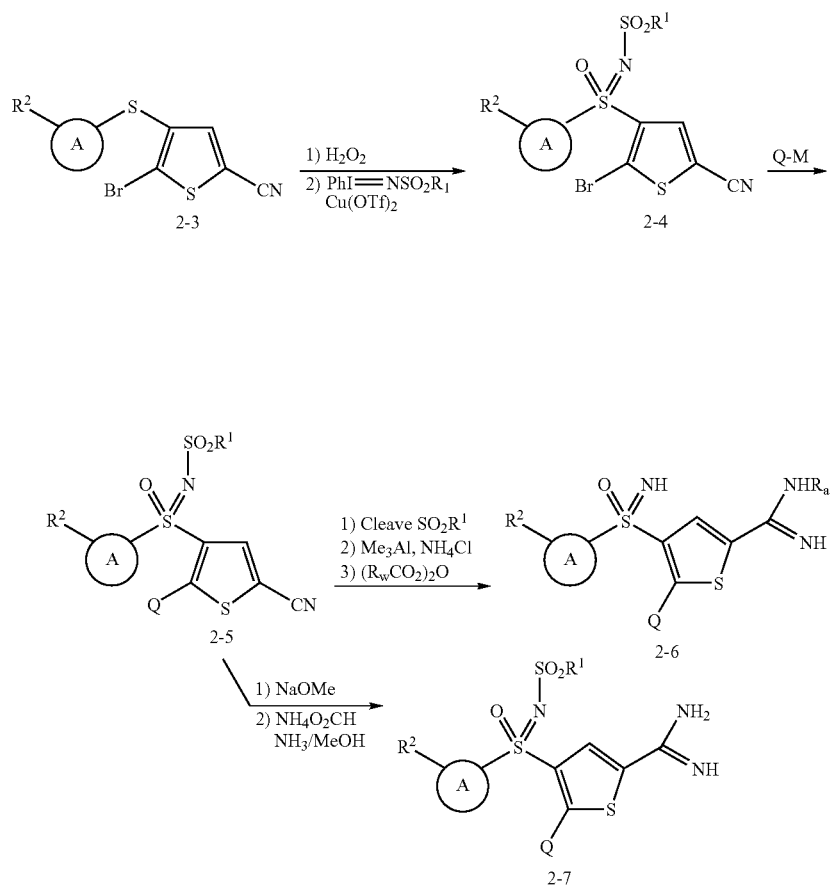

A solution of 4-Bromo-5-nitro-thiophene-2-carbonitrile (2-1) is treated with an optionally substituted aryl or heteroaryl thiol to afford thioether (2-2). Reaction with iron and ammonium chloride (Stanetty, P. and Kremslehner, M., *Heterocycles* 48: 259 (1998)), followed by tert-butyl nitrite and copper (II) bromide gives the bromide (2-3) ((see Doyle; Siegfried; Dellaria, *J. Org. Chem.* 42: 2426 (1977)). Oxidation with hydrogen peroxide followed by treatment with a substituted sulfonylimino iodinane and copper (II) triflate gives the sulfoximine (2-4). Reaction with a metallated nucleophile displaces the bromide to give sulfoximine (2-5). Cleavage of the sulfonamide with a suitable reagent, such as sodium methane thiolate, followed by treatment with trimethyl aluminum and ammonium chloride gives the carboxamidine (Garigipati, R., *Tetrahedron Lett.* 31: 1969 (1990)), which is then protected to give the product (2-6), which may be further derivatized at the sulfoximine, Q, or $R^2$ positions prior to acid catalyzed deprotection of the carboxamidine. Alternatively, the sulfoximine (2-5) may be reacted with sodium methoxide, followed by a methanolic solution of ammonia and ammonium formate to give the carboxamidine as the product (2-7).

Persons skilled in the art recognize that any examples synthesized in racemic form may be separated into the corresponding enantiomers using a high performance liquid chromatograph equipped with a chiral separation column.

EXAMPLE 3

4-[S-(3-Bromophenyl)-N-(2-nitrobenzene-sulfonyl) sulfoxamino]-5-methylsulfanyl-thiophene-2-carboxamidine trifluoroacetate

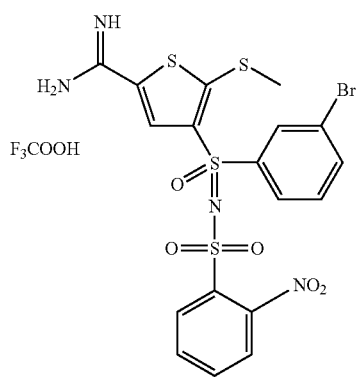

EXAMPLE 3a

[N-(2-Nitrobenzene-sulfonylimino)]phenyl iodinane

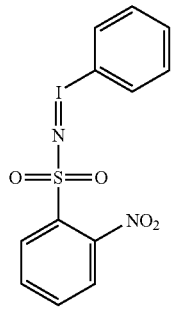

A suspension of 2-nitro-benzenesulfonamide (2.50 g, 12.4 mmol) in methanol (50 mL) was treated with solid potassium hydroxide (1.35 g, 30.9 mmol) and stirred at room temperature for 10 min. During this time the mixture turned clear then returned to a cloudy suspension. The mixture was cooled to 0° C., slowly treated with iodobenzene diacetate (3.38 g, 12.4 mmol), stirred at 0° C. for 10 min., and stirred at room temperature for 4 h. Solids were filtered, quickly washed with cold methanol, and dried under high vac to afford [N-(2-nitrobenzene-sulfonylimino)]phenyl iodinane (3.40 g, 68%) as an off-white solid. The crude material was used directly in the next reaction.

EXAMPLE 3b

4-[(3-Bromo-benzene)-N-(2-nitro-benzenesulfonyl)sulfoximino]-5-chloro-thiophene-2-carbonitrile

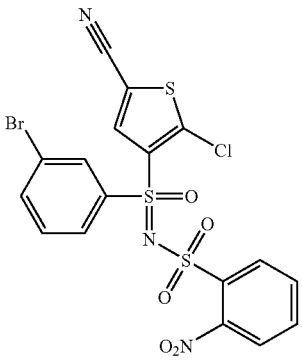

A solution of 4-(3-bromo-benzenesulfinyl)-5-chloro-thiophene-2-carbonitrile ((Example 24: step e) 200 mg, 0.558 mmol) in acetonitrile (3 mL) was treated with [N-(2-nitrobenzene-sulfonylimino)]phenyl iodinane ((Example 3: step a) 451 mg, 1.12 mmol). The flask was flushed with argon. The suspension was treated with copper (II) triflate (80.8 mg, 0.279 mmol) and stirred at room temperature for 2 h. The excess [N-(2-nitrobenzene-sulfonylimino)]phenyl iodinane was removed by filtering the mixture through Celite. The filter cake was washed with ethyl acetate, and the filtrate was washed with water, dried over MgSO$_4$, and concentrated in vacuo. Silica gel chromatography (25% EtOAc/hexanes to 40% EtOAc/hexanes raised in 5% increments) afforded 4-[(3-bromo-benzene)-N-(2-nitro-benzene-sulfonyl)sulfoximino]-5-chloro-thiophene-2-carbonitrile (101 mg, 33%) as a white solid. $^1$H NMR (CDCl$_3$): δ 8.176 (t, 1H, J=2.0 Hz), 8.110-8.081 (m, 1H), 8.078 (s, 1H), 8.072-8.040 (m, 1H), 7.869-7.837 (m, 1H), 7.720 (ddd, 2H, J=2.8 Hz, J=1.6 Hz), 7.701-7.655 (m, 1H), 7.512 (t, 1H, J=8.0 Hz).

EXAMPLE 3c

4-[(3-Bromo-benzene)-N-(2-nitro-benzenesulfonyl)sulfoximino]-5-chloro-thiophene-2-formamide methyl ester

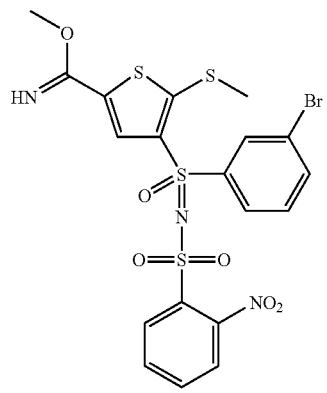

A solution of 4-[(3-bromo-benzene)-N-(2-nitrobenzene-sulfonyl)sulfoximino]-5-chloro-thiophene-2-carbonitrile ((Example 3: step b) 20.0 mg, 0.037 mmol) in tetrahydrofuran (2 mL) was cooled to −78° C. and treated dropwise with sodium thiomethoxide (87.0 μL of a 0.5 M solution in methanol, 0.044 mmol). The solution stirred −78° C. for 1 h and at room temperature for 20 min. Excess sodium thiomethoxide was quenched with 2 drops of glacial acetic acid. The solvents were removed in vacuo to afford 4-[(3-bromo-benzene)-N-(2-nitro-benzenesulfonyl)sulfoximino]-5-chloro-thiophene-2-formamide methyl ester. The crude material was used directly in the next reaction. C$_{19}$H$_{16}$BrN$_3$O$_6$S$_4$: 590.51 (M+1) found 589.8/591.8.

EXAMPLE 3d

4-[S-(3-Bromophenyl)-N-(2-nitrobenzene-sulfonyl)sulfoxamino]-5-methylsulfanyl-thiophene-2-carboxamidine trifluoroacetate

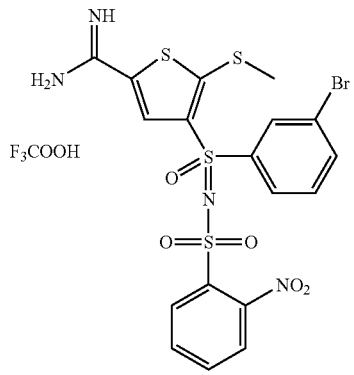

A solution of 4-[(3-bromo-benzene)-N-(2-nitro-benzene-sulfonyl)sulfoximino]-5-chloro-thiophene-2-formamide methyl ester ((Example 3: step c) 21.6 mg, 0.036 mmol) in methanol (5 mL) was treated with ammonium formate (23.1 mg, 0.366 mmol) and ammonia (2 mL of a 2M solution in methanol). The reaction was stirred at room temperature for 17 h. Minimal conversion to product (6%) was seen, therefore ammonia (100 µL of 7M solution in methanol) was added, and the reaction was heated to 40° C. for 12 h. Solvents were removed in vacuo. Preparatory HPLC (10-50% acetonitrile in 0.1% TFA/water over 30 min.) afforded 4-[S-(3-bromophenyl)-N-(2-nitrobenzene-sulfonyl)sulfoxamino]-5-methylsulfanyl-thiophene-2-carboxamidine trifluoroacetate (15.8 mg, 75%) as a colorless glassy solid. $^1$H NMR (CD$_3$OD): δ 8.394 (s, 1H), 8.201 (t, 1H, J=2.0 Hz), 8.066 (d, 1H, J=8.0 Hz), 7.944 (d, 2H, J=8.0 Hz), 7.814 (d, 2H, J=6.0 Hz), 7.750-7.698 (m, 1H), 7.585 (t, 1H, J=8.0 Hz), 2.695 (s, 3H). $C_{18}H_{15}BrN_4O_5S_4$: 575.50 (M+1) found 574.8/576.9.

EXAMPLE 4

4-[S-(3-Bromophenyl)-N-(3-acetamidobenzene-sulfonyl)sulfoxamino]-5-methylsulfanyl-thiophene-2-carboxamidine trifluoroacetate

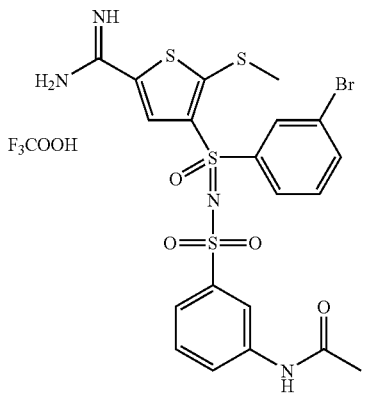

A solution of 4-[S-(3-Bromophenyl)-N-sulfonyl-3-analine sulfoximino]-5-methylsulfanyl-thiophene-2-carbamic acid tert-butyl ester ((Example 34: step b) 10.0 mg, 0.015 mmol) in CH$_2$Cl$_2$ (1 mL) was treated with triethylamine (4.3 µL, 0.031 mmol) and acetic anhydride (1.7 µL, 0.019 mmol). The reaction was stirred at room temperature for 4.5 h. Solvents were evaporated in vacuo. The residue was taken up in CH$_2$Cl$_2$ (1.5 mL) and treated with trifluoroactic acid (250 µL) at room temperature for 1 h. The solvents were evaporated in vacuo. Preparatory HPLC (10-50% acetonitrile in 0.1% TFA/water over 30 min.) afforded 4-[S-(3-bromophenyl)-N-(3-acetamidobenzene-sulfonyl)sulfoxamino]-5-methylsulfanyl-thiophene-2-carboxamidine trifluoroacetate (6.8 mg, 75%) as a colorless glassy solid. $^1$H NMR (CD$_3$OD): δ 8.348 (s, 1H), 8.260 (t, 1H, J=2.0 Hz), 8.073 (t, 1H, J=2.0 Hz), 7.990 (d, 1H, J=8.0 Hz), 7.902 (d, 1H, J=8.0 Hz), 7.633 (d, 1H, J=8.0 Hz), 7.536 (t, 2H, J=8.0 Hz), 7.429 (t, 1H, J=8.0 Hz), 2.687 (s, 3H), 2.179 (s, 3H). $C_{20}H_{19}BrN_4O_4S_4$: 587.56 (M+1) found 586.9/588.9.

EXAMPLE 5

4-[S-(3-Bromophenyl)-N-(3-{N,N-bismethanesulfonyl}aminobenzene-sulfonyl)sulfoxamino]-5-methylsulfanyl-thiophene-2-carboxamidine trifluoroacetate

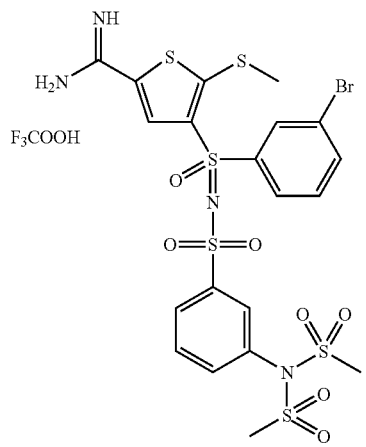

A solution of 4-[S-(3-Bromophenyl)-N-sulfonyl-3-analine sulfoximino]-5-methylsulfanyl-thiophene-2-carbamic acid tert-butyl ester ((Example 34: step b) 10.0 mg, 0.015 mmol) in CH$_2$Cl$_2$ (1 mL) was treated with triethylamine (4.3 µL, 0.031 mmol) and methanesulfonyl chloride (1.4 µL, 0.019 mmol). The reaction was stirred at room temperature for 1.5 h. Solvents were evaporated in vacuo. The residue was taken up in CH$_2$Cl$_2$ (1.5 mL) and treated with trifluoroacetic acid (250 µL) at room temperature for 1.5 h. Solvents were evaporated in vacuo. Preparatory HPLC (10-50% acetonitrile in 0.1% TFA/water over 30 min.) afforded 4-[S-(3-bromophenyl)-N-(3-{N,N-bismethanesulfonylamino}benzene-sulfonyl)sulfoxamino]-5-methylsulfanyl-thiophene-2-carboxamidine trifluoroacetate (7.0 mg, 72%) as a colorless glassy solid. $^1$H NMR (CD$_3$OD): δ 8.346 (s, 1H), 8.139 (t, 1H, J=2.0 Hz), 8.026-7.986 (m, 2H), 7.941 (d, 1H, J=8.0 Hz), 7.907 (d, 1H, J=8.0 Hz), 7.742 (d, 1H, J=8.0 Hz), 7.635 (t, 1H, J=8.0 Hz), 7.562 (t, 1H, J=8.0 Hz), 3.512 (s, 6H), 2.711 (s, 3H). $C_{20}H_{21}BrN_4O_7S_6$: 701.70 (M+1) found 700.9/702.8.

EXAMPLE 6

4-[S-(3-Bromophenyl)-N-(3-ureidobenzene-sulfonyl)sulfoxamino]-5-methylsulfanyl-thiophene-2-carboxamidine trifluoroacetate

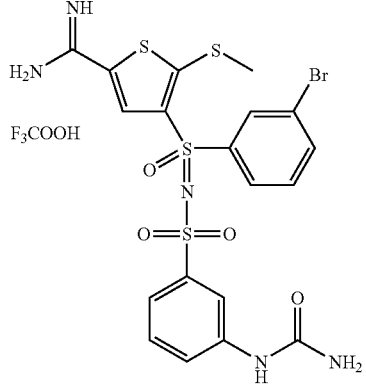

A solution of 4-[S-(3-Bromophenyl)-N-sulfonyl-3-analine sulfoximino]-5-methylsulfanyl-thiophene-2-carbamic acid tert-butyl ester ((Example 34: step b) 20.0 mg, 0.031 mmol) in $CH_2Cl_2$ (2 mL) was treated with pyridine (3.0 μL, 0.037 mmol) and p-nitrophenyl chloroformate (6.2 mg, 0.031 mmol). The reaction was stirred at room temperature for 40 min. Triethylamine (17.3 μL, 0.124 mmol) and ammonia (124 μL of a 0.5M solution in dioxane, 0.062 mmol) were added, and the reaction was stirred at room temperature for 15 h. The reaction was diluted with $CH_2Cl_2$ and washed with saturated aqueous $NaHCO_3$ until the aqueous layer no longer appears yellow. The organic layer was dried over $MgSO_4$ and concentrated in vacuo. The residue was taken up in $CH_2Cl_2$ (3 mL) and treated with trifluoroacetic acid (0.5 mL) at room temperature for 1 h. Solvents were evaporated in vacuo. Preparatory HPLC (10-50% acetonitrile in 0.1% TFA/water over 30 min.) afforded 4-[S-(3-bromophenyl)-N-(3-ureidobenzene-sulfonyl)sulfoxamino]-5-methylsulfanyl-thiophene-2-carboxamidine trifluoroacetate (14.9 mg, 82%) as a colorless glassy solid. $^1$H NMR ($CD_3OD$): δ 8.311 (s, 1H), 8.093 (t, 1H, J=2.0 Hz), 8.067 (t, 1H, J=2.0 Hz), 7.989 (d, 1H, J=8.0 Hz), 7.898 (d, 1H, J=2.0 Hz), 7.535 (t, 1H, J=8.0 Hz), 7.456 (dt, 2H, J=8.0 Hz, J=1.6 Hz), 7.408-7.328 (m, 2H), 2.688 (s, 3H). $C_{20}H_{21}BrN_4O_7S_6$: 588.55 (M+1) found 587.8/589.8.

EXAMPLE 7

4-[S-(3-Bromophenyl)-N-(3-methanesulfonamidobenzene-sulfonyl)sulfoxamino]-5-methylsulfanyl-thiophene-2-carboxamidine trifluoroacetate

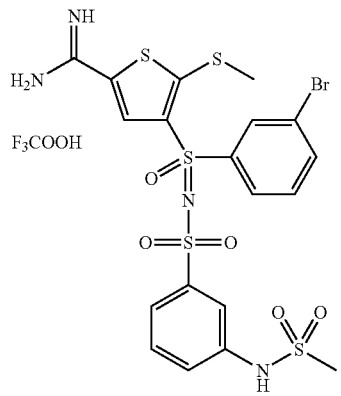

A solution of 4-[S-(3-Bromophenyl)-N-sulfonyl-3-analine sulfoximino]-5-methylsulfanyl-thiophene-2-carbamic acid tert-butyl ester ((Example 34: step b) 10.0 mg, 0.015 mmol) in $CH_2Cl_2$ (1 mL) was treated with triethylamine (2.6 μL, 0.019 mmol) and methanesulfonyl chloride (1.3 μL, 0.017 mmol). The reaction was stirred at room temperature for 16 h. Solvents were evaporated in vacuo. The residue was taken up in $CH_2Cl_2$ (2 mL) and treated with trifluoroacetic acid (0.5 mL) at room temperature for 1 h. Solvents were evaporated in vacuo. Preparatory HPLC (10-50% acetonitrile in 0.1% TFA/water over 30 min.) afforded 4-[S-(3-bromophenyl)-N-(3-methanesulfonamidobenzene-sulfonyl)sulfoxamino]-5-methylsulfanyl-thiophene-2-carboxamidine trifluoroacetate (6.2 mg, 64%) as a colorless glassy solid. $^1$H NMR ($CD_3OD$): δ 8.330 (s, 1H), 8.139 (t, 1H, J=2.0 Hz), 8.033 (d, 1H, J=8.0 Hz), 7.938 (d, 1H, J=8.0 Hz), 7.786 (t, 1H, J=2.0 Hz), 7.575 (t, 2H, J=8.0 Hz), 7.484 (t, 1H, J=8.0 Hz), 7.415 (d, 1H, J=8.0 Hz), 3.057 (s, 3H), 2.709 (s, 3H). $C_{19}H_{19}BrN_4O_5S_5$: 623.61 (M+1) found 622.7/624.8.

EXAMPLE 8

4-[S-(3-Bromophenyl)-N-{3-(5-methyl-[1,3,4]oxadiazol-2-yl)-benzene-sulfonyl}sulfoxamino]-5-methylsulfanyl-thiophene-2-carboxamidine trifluoroacetate

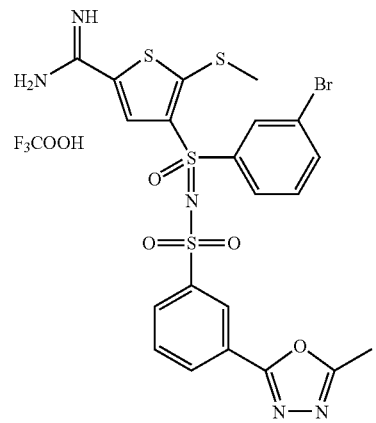

A solution of 4-[S-(3-bromophenyl)-sulfoxamino]-5-methylsulfanyl-thiophene-2-carbamic acid tert-butyl ester ((Example 24: step j) 20.0 mg, 0.041 mmol) in toluene (4 mL) was treated with triethylamine (13.6 μL, 0.100 mmol) and 3-(5-methyl-[1,3,4]oxadiazol-2-yl)-benzenesulfonyl chloride (12.6 mg, 0.049 mmol). The reaction was heated to 50° C. for 36 h. No conversion to product was seen at this time. Dimethyl-pyridin-4-yl-amine (DMAP, 110.0 mg, 0.082 mmol) was added, and the reaction was stirred at 50° C. for an additional 24 h. The reaction was diluted with ethyl acetate and washed with water, and the aqueous layer was extracted with ethyl acetate. The combined organic layers were dried over $MgSO_4$ and concentrated in vacuo. The residue was taken up in $CH_2Cl_2$ (4 mL) and treated with trifluoroacetic acid (1 mL) at room temperature for 1.5 h. The solvents were removed in vacuo. Preparatory HPLC (10-50% acetonitrile in 0.1% TFA/water over 30 min.) afforded 4-[S-(3-bromophenyl)-N-{3-(5-methyl-[1,3,4]oxadiazol-2-yl)-benzene-sulfonyl}sulfoxamino]-5-methylsulfanyl-thiophene-2-carboxamidine trifluoroacetate (14.0 mg, 56%) as a colorless glassy solid. $^1$H NMR ($CD_3OD$): δ 8.406 (t, 1H, J=1.2 Hz), 8.378 (s, 1H), 8.246 (d, 1H, J=8.0 Hz), 8.135 (t, 1H, J=2.0 Hz), 8.095 (d, 1H, J=8.0 Hz), 8.035 (d, 1H, J=8.0 Hz), 7.915 (d, 1H, J=8.0 Hz), 7.758 (t, 1H, J=8.0 Hz), 7.562 (t, 1H, J=8.0 Hz), 2.689 (s, 3H), 2.681 (s, 3H). $C_{19}H_{19}BrN_4O_5S_5$: 612.57 (M+1) found 611.9/613.9.

EXAMPLE 9

4-[S-(3-Bromophenyl)-N-{3-(oxazol-5-yl-benzene-sulfonyl)}sulfoxamino]-5-methylsulfanyl-thiophene-2-carboxamidine trifluoroacetate

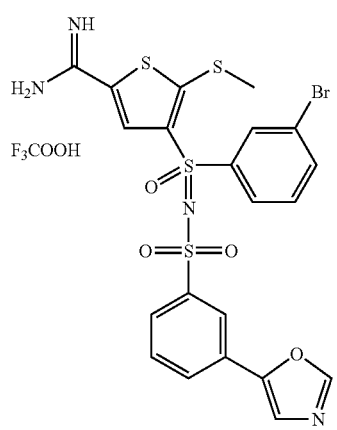

A solution of 4-[S-(3-bromophenyl)-sulfoxamino]-5-methylsulfanyl-thiophene-2-carbamic acid tert-butyl ester ((Example 24: step j) 20.0 mg, 0.041 mmol) in toluene (4 mL) was treated with triethylamine (13.6 µL, 0.100 mmol) and 3-oxazol-5-yl-benzenesulfonyl chloride (11.9 mg, 0.049 mmol). The reaction was heated to 50° C. for 36 h. No conversion to product was seen at this time. Dimethyl-pyridin-4-yl-amine (DMAP, 10.0 mg, 0.082 mmol) was added, and the reaction was stirred at 50° C. for an additional 24 h. The reaction was diluted with ethyl acetate and washed with water, and the aqueous layer was extracted with ethyl acetate. The combined organic layers were dried over MgSO$_4$ and concentrated in vacuo. The residue was taken up in CH$_2$Cl$_2$ (4 mL) and treated with trifluoroacetic acid (1 mL) at room temperature for 1.5 h. The solvents were removed in vacuo. Preparatory HPLC (10-50% acetonitrile in 0.1% TFA/water over 30 min.) afforded 4-[S-(3-bromophenyl)-N-{3-(oxazol-5-yl-benzene-sulfonyl}sulfoxamino]-5-methylsulfanyl-thiophene-2-carboxamidine trifluoroacetate (5.7 mg, 20%) as a colorless glassy solid. $^1$H NMR (CD$_3$OD): δ 8.355 (s, 1H), 8.348 (s, 1H), 8.128 (t, 1H, J=2.0 Hz), 8.088 (t, 1H, J=2.0 Hz), 8.026 (d, 1H, J=8.0 Hz), 7.975 (d, 1H, J=8.0 Hz), 7.916-7.865 (m 2H), 7.674 (s, 1H), 7.639 (t, 1H, J=8.0 Hz), 7.551 (t, 1H, J=8.0 Hz), 2.680 (s, 3H). C$_{19}$H$_{19}$BrN$_4$O$_5$S$_5$: 597.55 (M+1) found 596.9/598.8.

EXAMPLE 10

4-[S-[3-(2-amino-4-guanidino-6-methyl-phenyl)phenyl]-N-(4-ureidobenzene-sulfonyl)sulfoxamino]-5-methylsulfanyl-thiophene-2-carboxamidine bistrifluoroacetate

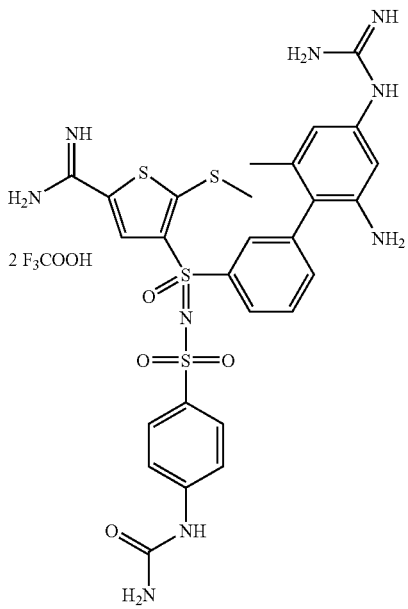

EXAMPLE 10a

4-[S-([6-Methyl-4-(2-trimethylsilanyl-ethoxycarbonyl amino)-biphenyl-2-yl]-carbamic acid 2-trimethylsilanyl-ethyl ester)-N-sulfony-4-urido-benzene sulfoximino]-5-methylsulfanyl-thiophene-2-carbamic acid tert-butyl ester

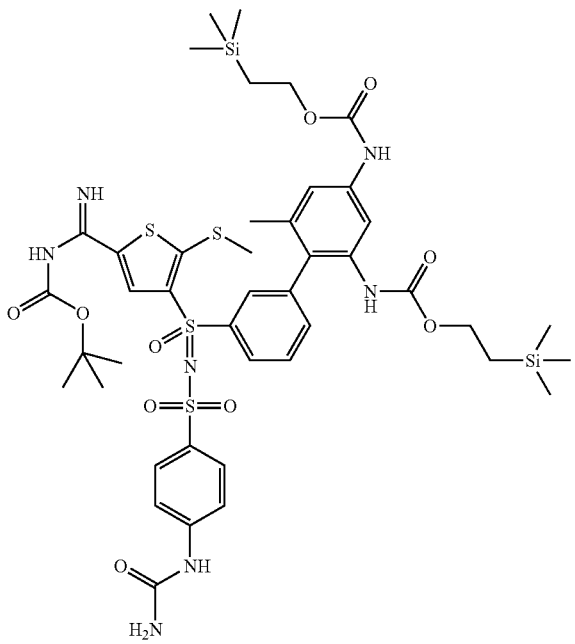

A solution of 4-[S-([6-Methyl-4-(2-trimethylsilanyl-ethoxycarbonylamino)-biphenyl-2-yl]-carbamic acid 2-trimethylsilanyl-ethyl ester)-N-sulfony-4-analine sulfoximino]-5-methylsulfanyl-thiophene-2-carbamic acid tert-butyl ester ((Example 48) 26.5 mg, 0.027 mmol) in CH$_2$Cl$_2$ (2 mL) was treated with pyridine (2.6 µL, 0.033 mmol) and p-nitrophenyl chloroformate (5.5 mg, 0.027 mmol). The reaction was stirred at room temperature for 30 min. Triethylamine (15.1 µL, 0.109 mmol) and ammonia (108.7 µL of a 0.5M solution in dioxane, 0.054 mmol) were added, and the reaction was stirred at room temperature for 45 min. The reaction was diluted with CH$_2$Cl$_2$ and washed with saturated aqueous NaHCO$_3$ until the aqueous layer no longer appeared yellow. The organic layer was dried over MgSO$_4$ and concentrated in vacuo to afford the product 4-[S-([6-Methyl-4-(2-trimethylsilanyl-ethoxycarbonylamino)-biphenyl-2-yl]-carbamic acid 2-trimethylsilanyl-ethyl ester)-N-sulfony-4-urido-benzene sulfoximino]-5-methylsulfanyl-thiophene-2-carbamic acid tert-butyl ester (21.0 mg, 76%) as a pale yellow solid. C$_{43}$H$_{59}$N$_7$O$_{10}$S$_4$Si$_5$: 1018.40 (M+1) found 917.9 (M+1-benzyloxycarbonyl).

EXAMPLE 10b

4-[S-([6-Methyl-biphenyl-2,4-diamine)-N-sulfony-4-ureidobenzene-sulfonyl)sulfoximino]-5-methylsulfanyl-thiophene-2-carbamic acid tert-butyl ester

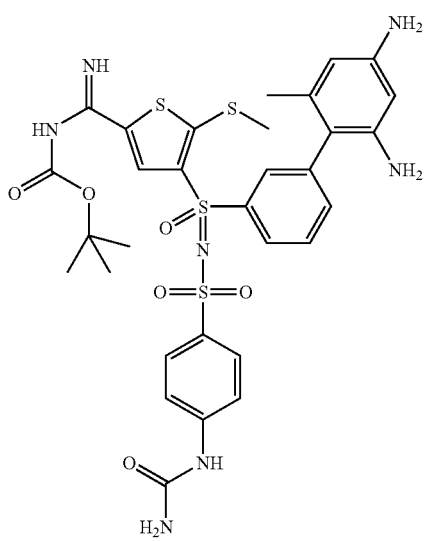

A 4-[S-([6-Methyl-4-(2-trimethylsilanyl-ethoxycarbonylamino)-biphenyl-2-yl]-carbamic acid 2-trimethylsilanyl-ethyl ester)-N-sulfony-4-urea-benzene sulfoximino]-5-methylsulfanyl-thiophene-2-carbamic acid tert-butyl ester ((Example 10: step a) 21.0 mg, 0.021 mmol) in tetrahydrofuran (3 mL) was heated to 50° C. and treated with tetrabutylammonium fluoride (62.0 µL as a 1M solution in tetrahydrofuran, 0.063 mmol). The reaction was stirred at 50° C. for 2.5 h. Solvents were removed in vacuo. The residue was taken up in ethyl acetate and washed well with water. The organic layer was dried over MgSO$_4$ and concentrated in vacuo to afford the product 4-[S-([6-Methyl-biphenyl-2,4-diamine)-N-sulfony-4-ureidobenzene-sulfonyl)sulfoximino]-5-methylsulfanyl-thiophene-2-carbamic acid tert-butyl ester (17.1 mg, 112%, some salt remained) as a light tan solid. C$_{43}$H$_{59}$N$_7$O$_{10}$S$_4$Si$_5$: 729.92 (M+1) found 730.0.

EXAMPLE 10c

4-[S-[3-(2-Amino-4-guanidino-6-methyl-phenyl)phenyl]-N-(4-ureidobenzene-sulfonyl)sulfoxamino]-5-methylsulfanyl-thiophene-2-carboxamidine bistrifluoroacetate

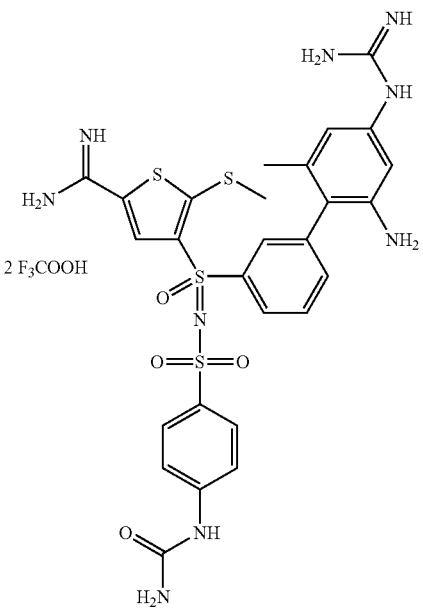

A 4-[S-([6-Methyl-biphenyl-2,4-diamine)-N-sulfony-4-urea-benzene sulfoximino]-5-methylsulfanyl-thiophene-2-carbamic acid tert-butyl ester ((Example 10: step b) 17 mg, 0.023 mmol) in 5% acetic acid/methanol (2 mL) was treated with 1,3-bis(tert-butoxycarbonyl)-2-methyl-2-thiopseudourea (6.8 mg, 0.023 mmol) and heated to 50° C. for 30 min. Solvents were removed in vacuo. The residue was taken up in CH$_2$Cl$_2$ (2 mL) and treated with trifluoroacetic acid (0.5 mL) at room temperature for 1.5 h. Solvents were removed in vacuo. Preparatory HPLC (10-50% acetonitrile in 0.1% TFA/water over 30 min.) afforded 4-[S-[3-(2-amino-4-guanidino-6-methyl-phenyl)phenyl]-N-(4-ureidobenzene-sulfonyl)sulfoxamino]-5-methylsulfanyl-thiophene-2-carboxamidine bistrifluoroacetate (8.2 mg, 52%) as a colorless glassy solid. $^1$H NMR (CD$_3$OD): δ 8.350 (d, 1H, J=4.0 Hz), 8.029 (d, 1H, J=8.0 Hz), 8.000 (d, 1H, J=1.2 Hz), 7.790 (t, 1H, J=8.0 Hz), 7.722 (dd, 2H, J=2.0 Hz, J=9.2 Hz), 7.646 (d, 1H, J=7.6 Hz), 7.497 (dd, 2H, J=2.0 Hz, J=8.8 Hz), 7.670 (d, 1H, J=2.4 Hz), 7.630 (t, 1H, J=1.2 Hz), 2.650 (d, 3H, J=1.6 Hz), 1.978 (d, 3H, J=4.4 Hz). C$_{27}$H$_{29}$N$_9$O$_4$S$_4$: 671.84 (M+1) found 672.1.

EXAMPLE 11

4-[S-(3-Bromophenyl)-N-p-tolyl-formamide]-5-methylsulfanyl-thiophene-2-carboxamidine trifluoroacetate

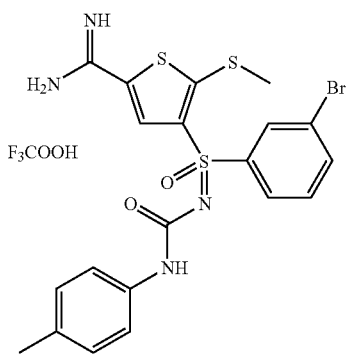

A solution of 4-[S-(3-bromophenyl)-sulfoxamino]-5-methylsulfanyl-thiophene-2-carbamic acid tert-butyl ester (Example 24: step j) 20.0 mg, 0.041 mmol) in tetrahydrofuran (1 mL) was treated with diisopropylethylamine (100 μL, 0.574 mmol) and 1-isocyanato-4-methyl benzene (400 μL of a 0.25 M solution in tetrahydrofuran, 0.751 mmol) at room temperature for 2 h. The reaction was diluted with EtOAc (50 mL) and was washed with citric acid (3×10 mL), NaHCO$_3$ (2×10 mL), and brine (20 mL). The organic layer was dried over Na$_2$SO$_4$ and concentrated in vacuo. The residue was taken up in CH$_2$Cl$_2$ (3 mL) and treated with trifluoroacetic acid (3 mL) at room temperature for 2 h. Solvents were evaporated in vacuo. Preparatory HPLC (10-55% acetonitrile in 0.1% TFA/water over 40 min.) afforded the title compound (5.2 mg, 25%) as a colorless glassy solid. $^1$H NMR (CD$_3$OD): δ 8.43 (s, 1H), 8.394 (s, 1H), 8.16 (d, H, J=8.0 Hz), 7.92 (d, 1H, J=8.0 Hz), 7.58 (t, 1H, J=8.0 Hz), 7.34 (d, 2H, J=8.0 Hz), 7.09 (d, 2H, J=8.8 Hz), 2.72 (s, 3H), 2.29 (s, 3H). C$_{20}$H$_{19}$BrN$_4$O$_2$S$_3$: 523.49 (M+1); found: 522.7/524.6.

EXAMPLE 12

4-[S-(3-Bromophenyl)-N-benzamide]-5-methylsulfanyl-thiophene-2-carboxamidine trifluoroacetate

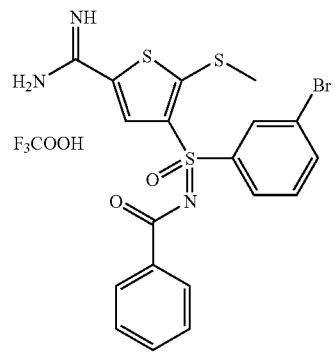

A solution of 4-[S-(3-bromophenyl)-sulfoxamino]-5-methylsulfanyl-thiophene-2-carbamic acid tert-butyl ester (Example 24: step j) 14.0 mg, 0.029 mmol) in tetrahydrofuran (2 mL) was cooled to 0° C. and treated with pyridine (160 μL, 2 mmol) and benzoyl chloride (150 μL of a 0.2M solution in tetrahydrofuran, 0.030 mmol) for 1 h. Because no conversion to product was seen under these conditions, the reaction was warmed to room temperature and stirred for 1 h. The reaction was treated with additional benzoyl chloride (750 μL, 0.150 mmol) over 3 h and allowed to stir at room temperature for 16 h. The reaction was diluted with EtOAc (50 mL) and was washed with citric acid (3×10 mL), NaHCO$_3$ (2×10 mL), and brine (20 mL). The organic layer was dried over Na$_2$SO$_4$ and concentrated in vacuo. The residue was taken up in CH$_2$Cl$_2$ (3 mL) and treated with trifluoroacetic acid (3 mL) for 2 h. Solvents were removed in vacuo. Preparatory HPLC of the residue (10-55% acetonitrile in 0.1% TFA/water over 40 min.) afforded the title compound (4.7 mg, 34%) as a colorless glassy solid. $^1$H NMR (CD$_3$OD): δ 8.48 (s, 1H), 8.36 (t, 1H, J=1.6 Hz), 8.24-8.21 (m, 3H), 7.96 (d, 1H, J=8.0 Hz), 7.66-7.60 (m, 2H), 7.55-7.50 (m, 2H), 2.70 (s, 3H). C$_{19}$H$_{16}$BrN$_3$O$_2$S$_3$: 494.45 (M+1); found: 493.9/495.9.

EXAMPLE 13

4-[S-(3-Bromophenyl)-N-3-nitro-benzamide]-5-methylsulfanyl-thiophene-2-carboxamidine trifluoroacetate

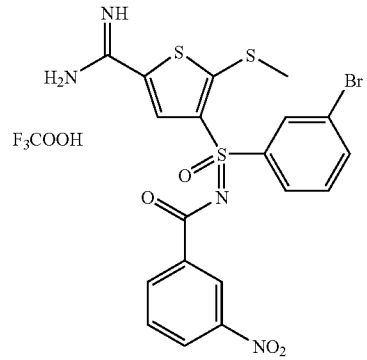

A solution of 4-[S-(3-bromophenyl)-sulfoxamino]-5-methylsulfanyl-thiophene-2-carbamic acid tert-butyl ester (Example 24: step j) 50.0 mg, 0.102 mmol) in tetrahydrofuran (3 mL) was treated with diisopropylethyl amine (175 μL, 1.00 mmol) and 3-nitrobenzoyl chloride (1.00 mL as a 0.5 M solution in CH$_2$Cl$_2$, 0.500 mmol). The reaction was stirred at room temperature for 30 min. The reaction was diluted with EtOAc (50 mL) and was washed with citric acid (3×10 mL), NaHCO$_3$ (2×10 mL), and brine (20 mL). The organic layer was dried over Na$_2$SO$_4$ and concentrated in vacuo. A portion of the residue (10 mg) was chromatographed on silica gel (10-50% EtOAc in Hex) to afford 4-[S-(3-bromophenyl)-N-3-nitro-benzamide]-5-methylsulfanyl-thiophene-2-tert butyl ester. The residue was taken up in CH$_2$Cl$_2$ (3 mL) and treated with trifluoroacetic acid (3 mL) at room temperature for 2 h. Preparatory HPLC (10-55% acetonitrile in 0.1% TFA/water over 40 min.) afforded the title compound (3.5 mg) as a colorless glassy solid. $^1$H NMR (CD$_3$OD): δ 8.49 (s, 1H), 8.37 (t, 1H, J=2.0 Hz), 8.23 (d, 1H, J=8.0 Hz), 8.16 (dt, 1H, J=8.0 Hz, J=1.2 Hz), 8.04 (dd, 1H, J=2.0 Hz, J=2.0 Hz), 7.98 (d, 1H, J=8.0 Hz), 7.63 (t, 1H, J=8.0 Hz), 7.60 (t, 1H, J=8.0 Hz), 7.47 (d, 1H, J=8.0 Hz), 2.71 (s, 3H). C$_{19}$H$_{15}$BrN$_4$O$_4$S$_3$: 539.45 (M+1); found: 538.8/540.8.

EXAMPLE 14

4-[S-(3-Bromophenyl)-N-3-amino-benzamide]-5-methylsulfanyl-thiophene-2-carboxamidine trifluoroacetate

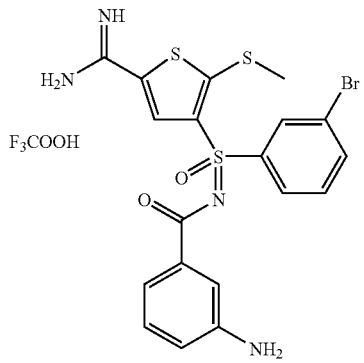

A solution of 4-[S-(3-bromophenyl)-N-3-nitro-benzamide]-5-methylsulfanyl-thiophene-2-tert butyl ester (Example 13: step intermediate) 20 mg, 0.03 mmol) in tetrahydrofuran (1 mL), ethanol (2 mL), and water (1 mL) was treated with sodium dithionite (52 mg, 0.3 mmol) at RT for 2 h. The reaction was diluted with EtOAc (50 mL) and was washed with citric acid (3×10 mL), NaHCO$_3$ (2×10 mL), and brine (20 mL). The organic layer was dried over Na$_2$SO$_4$ and concentrated in vacuo. The residue was taken up in CH$_2$Cl$_2$ (3 mL) and treated with trifluoroacetic acid (3 mL) for 1 h. Solvents were evaporated in vacuo. Preparatory HPLC (10-55% acetonitrile in 0.1% TFA/water over 40 min.) afforded the title compound (7 mg, 35%) as a colorless glassy solid. $^1$H NMR (CD$_3$OD): δ 9.01 (dd, 1H, J=2.0 Hz, J=2.0 Hz), 8.60 (d, 1H, J=7.6 Hz), 8.50 (d, 1H, J=8.0 Hz), 8.49 (s, 1H), 8.375 (t, 1H, J=2.0 Hz), 8.235 (d, 1H, J=8.0 Hz), 7.983 (d, 1H, J=8.0 Hz), 7.803 (t, 1H, J=8.0 Hz), 7.644 (t, 1H, J=8.0 Hz), 2.730 (s, 3H). C$_{19}$H$_{17}$BrN$_4$O$_2$S$_3$: 509.47 (M+1); found: 508.8/510.9.

EXAMPLE 15

4-[S-(3-Bromophenyl)-N-(phenylmethane-sulfonyl)sulfoxamino]-5-methylsulfanyl-thiophene-2-carboxamidine trifluoroacetate

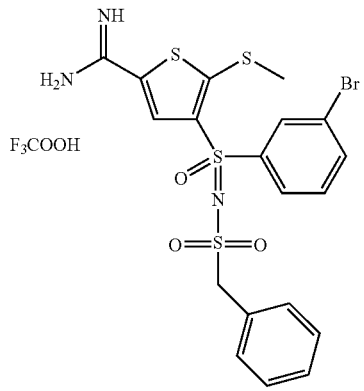

A solution of 4-[S-(3-bromophenyl)-sulfoxamino]-5-methylsulfanyl-thiophene-2-carbamic acid tert-butyl ester (Example 24: step j) 13.0 mg, 0.027 mmol) in CH$_2$Cl$_2$ (3 mL) was treated with triethylamine (175 µL, 1 mmol) and phenyl-methanesulfonyl chloride (0.2M in DCM, 300 µL, 0.6 mmol) at room temperature for 2 h. The reaction was diluted with EtOAc (50 mL) and was washed with citric acid (3×10 mL), NaHCO$_3$ (2×10 mL), and brine (20 mL). The organic layer was dried over Na$_2$SO$_4$ and concentrated in vacuo. The residue was taken up in CH$_2$Cl$_2$ (3 mL) and treated with trifluoroacetic acid (3 mL) at room temperature for 1 h. Solvents were removed in vacuo. Preparatory HPLC (10-55% acetonitrile in 0.1% TFA/water over 40 min.) afforded the title compound (8 mg, 57%) as a colorless glassy solid. $^1$H NMR (CD$_3$OD): δ 8.30 (s, 1H), 8.20 (t, 1H, J=1.6 Hz), 8.02 (d, 1H, J=8.4 Hz), 7.95 (d, 1H, J=8.0 Hz), 7.58 (t, 1H, J=8.0 Hz), 7.48-7.44 (m, 2H), 7.400-7.36 (m, 3H), 4.56 (s, 2H), 2.74 (s, 3H). C$_{19}$H$_{18}$BrN$_3$O$_3$S$_4$: 544.53 (M+1); found: 543.9/545.8.

EXAMPLE 16

4-[S-(3-Bromophenyl)-N-(methanesulfonyl)-sulfoxamino]-5-methylsulfanyl-thiophene-2-carboxamidine trifluoroacetate

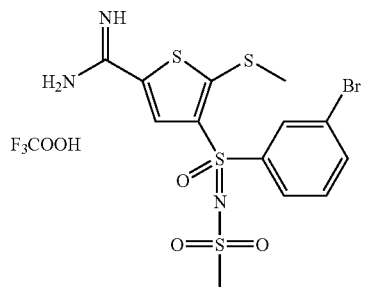

A solution of 4-[S-(3-bromophenyl)-sulfoxamino]-5-methylsulfanyl-thiophene-2-carbamic acid tert-butyl ester (Example 24: step j) 13.0 mg, 0.027 mmol) in CH$_2$Cl$_2$ (3 mL) was treated with triethylamine (175 µL, 1 mmol) and methanesulfonyl chloride (0.2 M in DCM, 200 µL, 0.4 mmol) at room temperature for 3 h. The reaction was diluted with EtOAc (50 mL) and was washed with citric acid (3×10 mL), NaHCO$_3$ (2×10 mL), and brine (20 mL). The organic layer was dried over Na$_2$SO$_4$ and concentrated in vacuo. The residue was taken up in CH$_2$Cl$_2$ (3 mL) and treated with trifluoroacetic acid (3 mL) at room temperature for 1 h. Solvents were removed in vacuo. Preparatory HPLC (10-55% acetonitrile in 0.1% TFA/water over 40 min.) afforded the title compound (7 mg, 58%) as a colorless glassy solid. $^1$H NMR (CD$_3$OD): δ 8.38 (s, 1H), 8.26 (t, 1H, J=1.6 Hz), 8.10 (d, 1H, J=8.0 Hz), 7.96 (d, 1H, J=8.0 Hz), 7.60 (t, 1H, J=8.0 Hz), 3.19 (s, 3H), 2.75 (s, 3H). C$_{13}$H$_{14}$BrN$_3$O$_3$S$_4$: 468.44 (M+1); found: 467.8/469.8.

EXAMPLE 17

4-[S-(3-Bromophenyl)-N-({2-aminophenyl}methane-sulfonyl)sulfoxamino]-5-methylsulfanyl-thiophene-2-carboxamidine trifluoroacetate

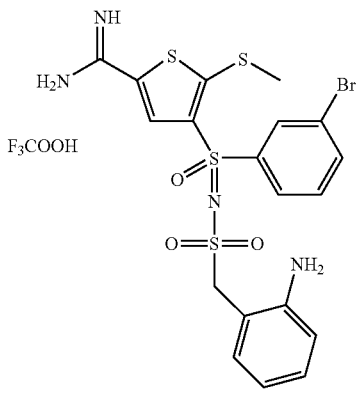

EXAMPLE 17a

4-[S-(3-Bromophenyl)-N-({2-nitrophenyl}methane-sulfonyl)sulfoxamino]-5-methylsulfanyl-thiophene-2-tert butyl ester

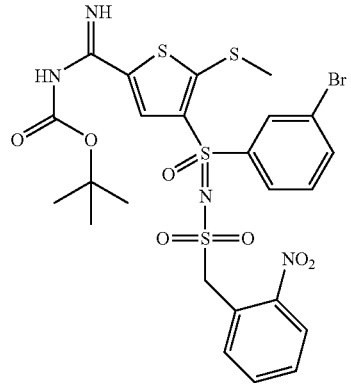

A solution of 4-[S-(3-bromophenyl)-sulfoxamino]-5-methylsulfanyl-thiophene-2-carbamic acid tert-butyl ester (Example 24: step j) 20.0 mg, 0.041 mmol) in tetrahydrofuran (3 mL) was treated with diisopropylethylamine (60.0 µL, 0.344 mmol) and (2-nitrophenyl)methanesulfonyl chloride (240 µL of a 0.2 M solution in DCM, 0.120 mmol) at room temperature for 6 h. The reaction was treated with additional 2-nitrophenylmethanesulfonyl chloride (240 µL of a 0.2 M solution in DCM, 0.120 mmol) and was stirred for 16 h. The reaction was diluted with EtOAc (50 mL) and was washed with citric acid (3×10 mL), NaHCO$_3$ (2×10 mL), and brine (20 mL). The organic layer was dried over Na$_2$SO$_4$ and concentrated in vacuo. Silica gel chromatography (10-60% EtOAc in hexanes) afforded 4-[S-(3-Bromophenyl)-N-({2-nitrophenyl}methane-sulfonyl)sulfoxamino]-5-methylsulfanyl-thiophene-2-tert butyl ester (20 mg, 0.03 mmol) as an off-white solid. C$_{24}$H$_{25}$BrN$_4$O$_7$S$_4$: 689.65 (M+1); found: 688.6/690.6.

EXAMPLE 17b

4-[S-(3-Bromophenyl)-N-({2-aminophenyl}methane-sulfonyl)sulfoxamino]-5-methylsulfanyl-thiophene-2-carboxamidine trifluoroacette

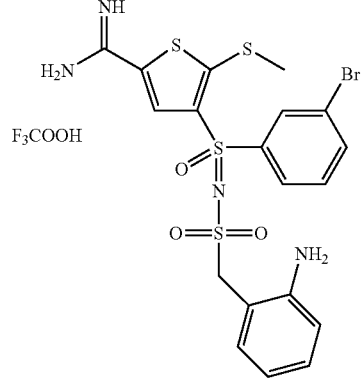

A solution of 4-[S-(3-bromophenyl)-N-({2-nitrophenyl}methane-sulfonyl)sulfoxamino]-5-methylsulfanyl-thiophene-2-tert butyl ester (Example 17: step a; 20.0 mg, 0.029 mmol) in tetrahydrofuran (3 mL) and water (1 mL) was treated with aqueous sodium dithionite (0.5 mL of a 0.5 M solution, 0.250 mmol) and stirred at room temperature for 1 h. The reaction was diluted with ethyl acetate (30 mL) and washed with water (2×10 mL). The organic layer was dried over Na$_2$SO$_4$ and concentrated in vacuo. A portion of the residue (4.0 mg, 0.006 mmol) was taken up in CH$_2$Cl$_2$ (3 mL) and treated with trifluoroacetic acid (3 mL) at room temperature for 2 h. Solvents were evaporated in vacuo. Preparatory HPLC of the residue (10-55% acetonitrile in 0.1% TFA/water over 40 min.) afforded the title compound (3 mg, 70%) as a colorless glassy solid. $^1$H NMR (CD$_3$OD): δ 8.33 (s, 1H), 8.24 (t, 1H, J=1.6 Hz), 8.04 (d, 1H, J=8.4 Hz), 7.97 (d, 1H, J=8.0 Hz), 7.60 (t, 1H, J=8.0 Hz), 7.36 (dd, 1H, J=7.6 Hz, J=1.2 Hz), 7.32 (dt, 1H, J=2.0 Hz, J=7.6 Hz), 7.08 (dd, 1H, J=0.8 Hz, J=8.0 Hz), 7.03 (dt, 1H, J=1.2 Hz, J=7.2 Hz), 4.66 (s, 2H), 2.75 (s, 3H). C$_{19}$H$_{19}$BrN$_4$O$_3$S$_4$: 559.55 (M+1); found: 558.7/560.7.

EXAMPLE 18

4-[S-[3-(2-Amino-4-guanidino-6-methyl-phenyl)phenyl]-N-(3-ureidobenzene-sulfonyl)sulfoxamino]-5-methylsulfanyl-thiophene-2-carboxamidine bistrifluoroacetate

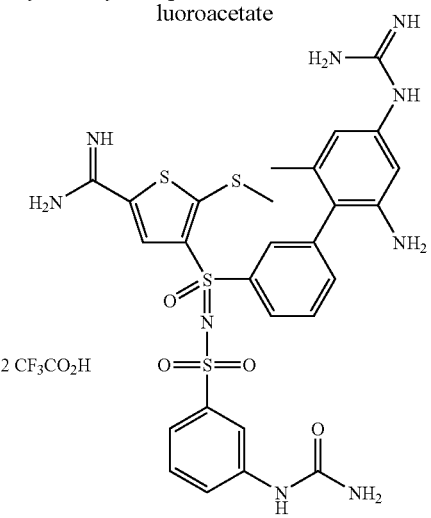

EXAMPLE 18a

4-[S-(3-Bromophenyl)-N-(sulfonyl-3-nitrobenzene)-sulfoximino]-5-chloro-thiophene-2-carbonitrile

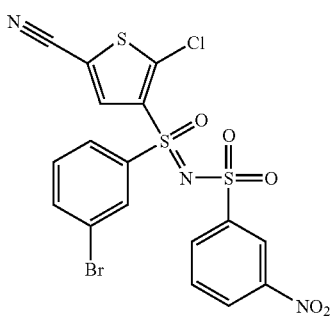

A solution of 4-(3-bromo-benzenesulfinyl)-5-chloro-thiophene-2-carbonitrile (Example 24: step e; 347 mg, 1 mmol), (N-(3-nitrosulfonylbenzene)imino)phenyl iodinane (prepared analogously to (N-(4-nitrosulfonylbenzene) imino)phenyl iodinane in Example 24: step f; 450 mg, 1.2 mmol), and copper triflate (36 mg, 0.1 mmol) in acetonitrile (4 mL) was stirred for 30 min at RT. An additional 80 mg of (N-(3-nitrosulfonylbenzene)imino)phenyl iodinane was added and after 30 min of stirring, the reaction was partitioned between EtOAc (100 mL) and NaHCO$_3$ (30 mL). The layers were separated and the organic layer was washed with water (3×20 mL) and brine (30 mL). The organic solution was dried over Na$_2$SO$_4$, concentrated in vacuo, and the residue was purified via silica gel flash chromatography to yield the product contaminated with sulfoxide starting material. Recrystallization from DCM-Hexanes yielded the product (410 mg, 75%). $^1$H NMR (CDCl$_3$): δ 8.91 (t, 1H, J=2.0 Hz), 8.42 (ddd, 1H, J=1.0, 2.0, 8.1 Hz), 8.34 (ddd, 1H, J=1.2, 1.6, 8.0 Hz), 8.11 (t, 1H, J=2.0 Hz), 8.06 (s, 1H), 7.97 (ddd, 1H, J=1.0, 1.8, 8.1 Hz), 7.74 (ddd, 1H, J=1.0, 1.8, 8.1 Hz), 7.68 (t, 1H, J=8.0 Hz), 7.43 (t, 1H, J=8.0 Hz).

EXAMPLE 18b

4-[S-(3-Bromophenyl)-N-(sulfonyl-3-nitrobenzene)-sulfoximino]-5-methylsulfanyl-thiophene-2-carbamic acid tert-butyl ester

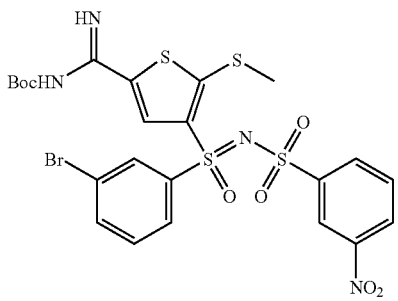

To a solution of 4-[S-(3-bromophenyl)-N-(sulfonyl-3-nitrobenzene)-sufloximino]-5-chloro-thiophene-2-carbonitrile (Example 18: step a; 410 mg, 0.75 mmol) in THF at −78° C. was added a solution of NaSMe (0.5M, 3 mL, 1.5 mmol) in MeOH. The reaction as allowed to warm to RT over 30 min and was stirred for an additional hr at RT. Ethyl acetate (100 mL) and aqueous NaHCO$_3$ (30 mL) were added and the layers were separated. The organic layer was washed with water (10 mL), brine (10 mL), and was dried over Na$_2$SO$_4$. The solution was concentrated and the residue was dissolved in methanolic ammonia (7N, 40 mL) and THF (10 mL). Ammonium formate (200 mg) was added and the reaction was heated at 40° C. for 16 h. The solvent was removed in vacuo and the residue was dissolved in 1:1 dioxane/MeOH (20 mL). Di-tert-butyldicarbonate (6.6 g, 30 mmol) and DIEA (5 mL) were added and the reaction was stirred for 4 h at RT. EtOAc (100 mL) and citric acid (1M, 30 mL) were added and the layers were separated. The organic layer was washed with citric acid (3×30 mL), NaHCO$_3$ (30 mL), brine (50 mL), and was dried over Na$_2$SO$_4$. Concentration of the solution followed by silica gel flash chromatography (5-40% EtOAc in hexanes) yielded the product (325 mg, 64%). $^1$H NMR (CDCl$_3$): δ $^1$H NMR (CDCl$_3$): δ 8.77 (t, 1H, J=2.0 Hz), 8.37 (ddd, 1H, J=1.0, 2.2, 8.2 Hz), 8.30 (ddd, 1H, J=1.0, 1.6, 8.0 Hz), 8.10 (t, 1H, J=2.0 Hz), 8.01 (s, 1H), 7.97 (ddd, 1H, J=1.0, 1.8, 8.1 Hz), 7.73 (ddd, 1H, J=1.0, 1.8, 8.1 Hz), 7.67 (t, 1H, J=8.0 Hz), 7.41 (t, 1H, J=8.0 Hz), 2.55 (s, 3H), 1.50 (s, 9H). C$_{23}$H$_{23}$BrN$_4$O$_7$S$_4$: 675.0 (M+1); found: 674.6/676.6.

EXAMPLE 18c

4-[S-([6-Methyl-4-(2-trimethylsilanyl-ethoxycarbonylamino)-biphenyl-2-yl]-carbamic acid 2-trimethylsilanyl-ethyl ester)-N-sulfonyl-3-nitro-benzene sulfoximino]-5-methylsulfanyl-thiophene-2-carbamic acid tert-butyl ester

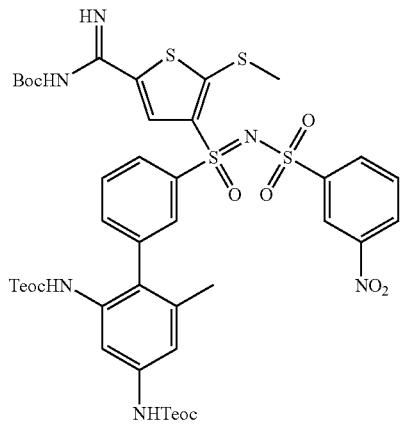

A solution of 4-[S-(3-Bromophenyl)-N-(sulfonyl-3-nitrobenzene)-sulfoximino]-5-methylsulfanyl-thiophene-2-carbamic acid tert-butyl ester (325 mg, 0.48 mmol), di-Teoc-pinacolboronate (Example 18: step b; 403 mg, 0.75 mmol), and saturated NaHCO$_3$ (2 mL) in dimethoxyethane (4 mL) was sparged with argon for 10 min, and tetrakis(triphenylphosphine)palladium (0) (80 mg, 0.072 mmol) was added. The solution was heated to 80° C. for 8 h. The solution was partition between EtOAc (60 mL) and water (20 mL) and the layers were separated. The organic layer was washed with water (20 mL), brine (20 mL) and was dried over Na$_2$SO$_4$. Concentration of the solvent followed by silica gel flash chromatography yielded the product (227 mg, 48%). $^1$H NMR (CDCl$_3$): δ 8.81 (m, 1H), 8.37 (m, 1H), 8.30 (m, 1H), 7.70-8.05 (m, 3H), 7.66 (m, 2H), 7.51 (m, 1H), 7.27 (m, 2H), 6.65 (s, 1H), 5.98 (br m, 1H), 4.27 (m, 2H), 4.09 (m, 2H), 2.57 (br d, 3H), 1.97 (br d, 3H), 1.51 (s, 9H), 1.06 (m, 2H), 0.90 (m, 2H), 0.07 (s, 9H), −0.04 (s, 9H). $C_{42}H_{56}N_6O_{11}S_4Si_2$: 1005.2 (M+1); found: 904.9 ((M+1)-Boc).

EXAMPLE 18d

4-[S-([6-Methyl-4-(2-trimethylsilanyl-ethoxycarbonylamino)-biphenyl-2-yl]-carbamic acid 2-trimethylsilanyl-ethyl ester)-N-sulfonyl-3-analine sulfoximino]-5-methylsulfanyl-thiophene-2-carbamic acid tert-butyl ester

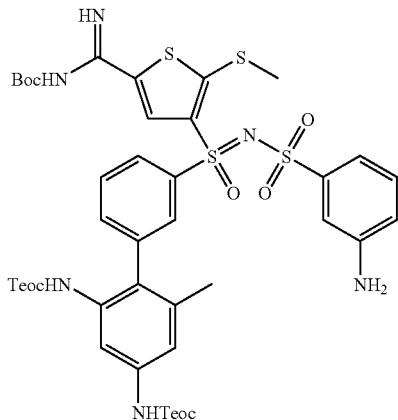

The procedure outlined in Example 33: step b was followed using 4-[S-([6-Methyl-4-(2-trimethylsilanyl-ethoxycarbonylamino)-biphenyl-2-yl]-carbamic acid 2-trimethylsilanyl-ethyl ester)-N-sulfonyl-3-nitro-benzene sulfoximino]-5-methylsulfanyl-thiophene-2-carbamic acid tert-butyl ester ((Example 18: step c) 114 mg, 0.11 mmol), iron powder (100 mg, 2 mmol), saturated ammonium chloride (1 mL), ethanol (4 mL) and dioxane (1 mL). Analogous workup followed by purification by silica gel flash chromatography yielded the product (75 mg, 68%) as a colorless glassy solid. $C_{42}H_{58}N_6O_9S_4Si_2$: 975.3 (M+1); found: 975.1.

EXAMPLE 18e

4-[S-([6-Methyl-4-(2-trimethylsilanyl-ethoxycarbonylamino)-biphenyl-2-yl]-carbamic acid 2-trimethylsilanyl-ethyl ester)-N-sulfonyl-3-ureidobenzene-sulfonyl)sulfoximino]-5-methylsulfanyl-thiophene-2-carbamic acid tert-butyl ester

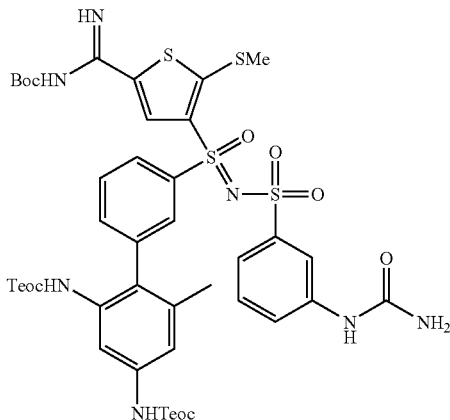

A solution of p-nitrophenyl chloroformate (0.2 M, 385 uL, 0.077 mmol) was added to a 0° C. solution of 4-[S-([6-Methyl-4-(2-trimethylsilanyl-ethoxycarbonylamino)-biphenyl-2-yl]-carbamic acid 2-trimethylsilanyl-ethyl ester)-N-sulfonyl-3-analine sulfonyl sulfoximino]-5-methylsulfanyl-thiophene-2-carbamic acid tert-butyl ester ((Example 18: step d) 75 mg, 0.077 mmol) and pyridine (20 μL, 0.231 mmol) in $CH_2Cl_2$ (2 mL). The reaction was stirred at room temperature for 30 min and the reaction was divided into two portions. Ammonia (5 mL of a 0.5M solution in dioxane, 2.5 mmol) was added and the reaction was stirred at room temperature for 45 min. The reaction was diluted with EtOAc and was washed with saturated aqueous $NaHCO_3$ until the aqueous layer no longer appeared yellow. The organic layer was dried over $Na_2SO_4$ and concentrated in vacuo to afford the title product (35 mg, 76%) as a pale yellow glass which was used without further purification. $C_{43}H_{59}N_7O_{10}S_4Si_5$: 1018.3 (M+1); found: 918.1 ((M+1)-Boc).

EXAMPLE 18f

4-[S-[3-(2-Amino-4-guanidino-6-methyl-phenyl)phenyl]-N-(3-ureidobenzene-sulfonyl)sulfoximino]-5-methylsulfanyl-thiophene-2-carboxamidine bistrifluoroacetate

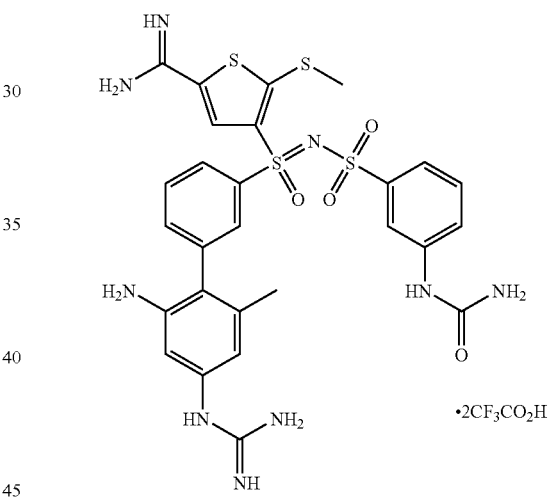

A solution of -[S-([6-Methyl-4-(2-trimethylsilanyl-ethoxycarbonylamino)-biphenyl-2-yl]-carbamic acid 2-trimethylsilanyl-ethyl ester)-N-sulfonyl-3-ureidobenzene-sulfonyl)sulfoximino]-5-methylsulfanyl-thiophene-2-carbamic acid tert-butyl ester (Example 18: step e) 35.0 mg, 0.035 mmol) in tetrahydrofuran (2 mL) was heated to 50° C. and treated with tetrabutylammonium fluoride (1M in THF, 350 μL, 0.35 mmol). The reaction was stirred at 50° C. for 30 min. The residue was taken up in ethyl acetate (30 mL) and was washed with water (5×10 mL). The organic layer was dried over $Na_2SO_4$ and concentrated in vacuo. $C_{31}H_{35}N_7O_6S_4$: 730.2 (M+1); Found: 730.0. The residue was dissolved in 5% acetic acid in methanol (2 mL) was treated with 1,3-bis(tert-butoxycarbonyl)-2-methyl-2-thiopseudourea (11.6 mg, 0.04 mmol) and heated to 40° C. for 12 h. $C_{42}H_{53}N_9O_9S_4$: 972.3 (M+1); found: 972.1. Solvents were removed in vacuo, the residue was taken up in $CH_2Cl_2$ (2 mL) and treated with trifluoroacetic acid (0.5 mL) at room temperature for 1.5 h. Solvents were removed in vacuo. Preparatory HPLC (10-50% acetonitrile in 0.1% TFA/water over 30 min.) afforded 4-[S-[3-(2-amino-4-guanidino-6-methyl-phenyl)phenyl]-N-(3-ureidobenzene-sulfonyl)sulfox-amino]-5-methylsulfanyl-thiophene-2-carboxamidine bistrifluoroacetate (6.3 mg) as a colorless glassy solid. ¹H NMR (CD₃OD): δ 8.36 (m, 1H), 8.15 (m, 1H), 8.00 (m, 1H), 7.99 (m, 1H), 7.75 (m, 1H), 7.63 (m, 1H), 7.44 (m, 2H), 7.37 (m, 1H); 6.65 (s, 1H), 6.61 (m, 1H), 2.66 (br d, 3H), 1.96 (br d, 3H). C₂₇H₂₉N₉O₄S₄: 672.8 (M+1) found: 673.1.

EXAMPLE 19

4-[S-(3-Bromo-benzenesulfonyl)-N-(m-sulfonyl benzoic acid)-sulfoxamino]-5-methylsulfanyl-thiophene-2-carboxamidine trifluoroacetate

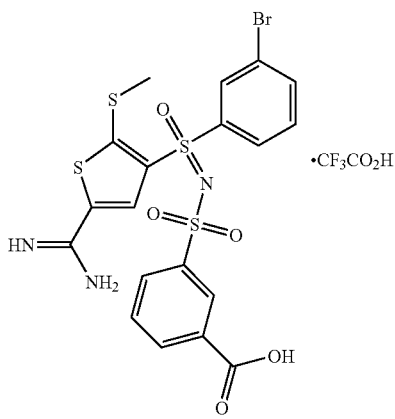

EXAMPLE 19a

3-Sulfamoyl-benzoic acid tert-butyl ester

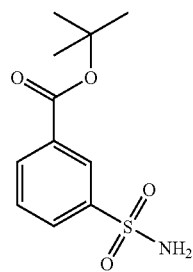

Sulfuric acid (conc., 498 µL, 9.06 mmol) was added to a suspension of MgSO₄ (4.36 g, 36.22 mmol) in CH₂Cl₂ (36 mL). The reaction mixture was stirred for 15 minutes, treated with 3-chlorosulfonyl-benzoic acid (Aldrich, 2 g, 9.06 mmol) and 2-methyl-propan-2-ol (anhydrous, 4.33 mL, 45.27 mmol), capped tightly, and stirred overnight at room temperature. The next day, the mixture was cooled to 0° C., treated with 7N NH₃ in methanol (Aldrich, 40 mL) dropwise, and stirred for 30 minutes. The solvents were removed in vacuo and the crude was dissolved in ethyl acetate and saturated NaHCO₃. The organic layer was washed with saturated NaHCO₃, water, and brine, dried over MgSO₄, filtered, and concentrated in vacuo to afford the title compound as a white solid (1 g, 42.9% yield). ¹H-NMR (CDCl₃): δ 8.51-8.53 (m, 1H), 8.20-8.21 (m, 1H), 8.08-8.11 (m, 1H), 7.57-7.62 (m, 1H), 5.09 (bs, 2H), and 1.61 (s, 9H).

EXAMPLE 19b (N-(m-Sulfonyl benzoic acid tert-butyl ester)imino)phenyliodinane

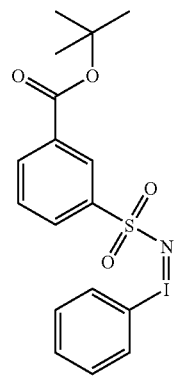

Potassium hydroxide (141 mg, 2.52 mmol) was added to a solution of 3-sulfamoyl-benzoic acid tert-butyl ester (Example 19: step a, 259 mg, 1.01 mmol) in methanol (anhydrous, 4 mL). The reaction mixture was stirred for 30 minutes at room temperature, cooled to 0° C., and purged with argon. Iodobenzenediacetate (Aldrich, 324 mg, 1.01 mmol) was added and the reaction mixture was stirred overnight at room temperature. Water (30 mL) was added to the reaction mixture until a precipitate formed. The mixture was cooled in the refrigerator for 3 hours, and then the solids were filtered and dried overnight to afford the title compound as a yellow solid (237 mg, 51% yield).

EXAMPLE 19c

4-[S-(3-Bromophenyl)-N-(m-sulfonyl benzoic acid tert-butyl ester)sufoxamino]-5-methylsulfanyl-thiophene-2-carbonitrile

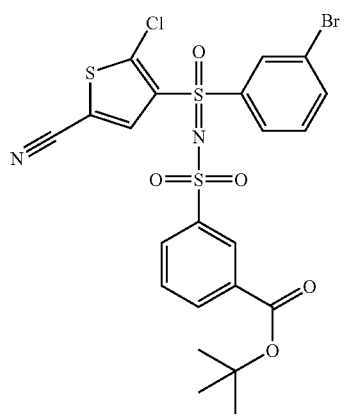

Copper (II) trifluoromethanesulfonate (Aldrich, 8.6 mg, 0.024 mmol) was added to a suspension of 4-(3-bromo-benzenesulfinyl)-5-chloro-thiophene-2-carbonitrile (Example 24: step e, 82.8 mg, 0.24 mmol) and (N-(m-sulfonyl benzoic acid tert-butyl ester)imino)phenyliodinane (Example 19: step b, 219.5 mg, 0.48 mmol) in acetonitrile (anhydrous, 1 mL) under argon. The reaction mixture was stirred at RT under argon overnight, concentrated in vacuo, diluted in ethyl acetate, and washed with brine. The organic layer was dried over magnesium sulfate, filtered, concentrated in vacuo, and purified by column chromatography (silica gel, 40-50% ethyl acetate/hexanes) to afford the title compound as a white solid (47.9 mg, 33.3% yield). $^1$H-NMR (CDCl$_3$): δ 8.54-8.56 (m, 1H), 8.12-8.22 (m, 3H), 8.01-8.04 (m, 2H), 7.83-7.87 (m, 1H), 7.48-7.61 (m, 2H), 1.63 (s, 9H).

EXAMPLE 19d

4-[S-(3-Bromophenyl)-N-(m-sulfonyl benzoic acid tert-butyl ester)-sulfoxamino]-5-methylsulfanyl-thiophene-2-carboximidic acid methyl ester

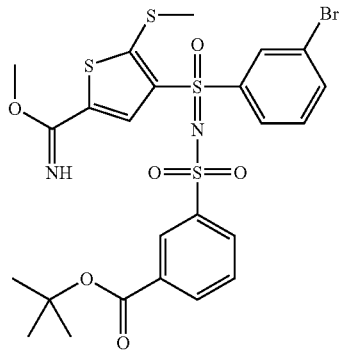

Sodium thiomethoxide solution (0.1M in methanol, 955 μL, 0.096 mmol) was added to a −78° C. solution of 4-[S-(3-bromophenyl)-N-(m-sulfonyl benzoic acid tert-butyl ester)sufoxamino]-5-methylsulfanyl-thiophene-2-carbonitrile (Example 19: step c, 47.9 mg, 0.080 mmol) in THF (anhydrous, 3 mL) under argon. The reaction mixture was warmed to room temperature, stirred overnight, and concentrated in vacuo. The residue was diluted with ethyl acetate and washed with saturated NaHCO$_3$, water, and brine. The organic layer was dried over magnesium sulfate, filtered, and concentrated in vacuo to afford the title compound as a yellow oil (51.4 mg, quantitative). $^1$H-NMR (CDCl$_3$): δ 8.54-8.55 (m, 1H), 8.12-8.18 (m, 3H), 8.00-8.04 (m, 1H), 7.75-7.82 (m, 2H), 7.41-7.57 (m, 2H), 3.85-3.90 (m, 3H), 2.59 (s, 3H), and 1.62 (s, 9H).

EXAMPLE 19e

4-[S-(3-Bromo-benzenesulfonyl)-N-(m-sulfonyl benzoic acid tert-butyl ester)-sulfoxamino]-5-methylsulfanyl-thiophene-2-carboxamidine

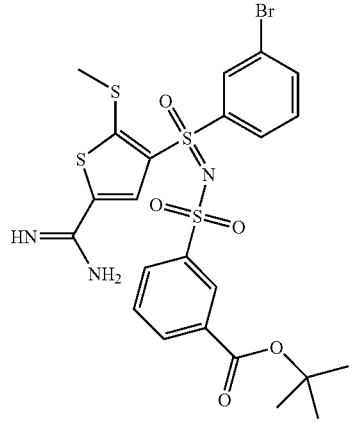

Ammonium formate (Aldrich, 25.1 mg, 0.398 mmol) was added to a solution of 4-[S-(3-bromophenyl)-N-(m-sulfonyl benzoic acid tert-butyl ester)-sulfoxamino]-5-methylsulfanyl-thiophene-2-carboximidic acid methyl ester (Example 19: step d, 51.4 mg, 0.080 mmol) in 2.0 M NH$_3$ in methanol (anhydrous, 4 mL) under argon. The reaction mixture was heated to 40° C. for 4.5 hours, and then stirred overnight at RT. Ammonium formate (25.1 mg, 0.398 mmol) was added, and then the reaction was heated to 40° C. for 2 hours. Another five equivalents of ammonium formate were added, and then the reaction mixture was heated for two hours more. The reaction was cooled to room temperature, diluted with THF (0.5 mL) and TEA (0.5 mL), and concentrated in vacuo to afford the title compound as a yellow oil (50.2 mg, quantitative). ESI-MS (m/z): Calcd. for C$_{23}$H$_{24}$BrN$_3$O$_5$S$_4$: 573.9 (M-tert-butyl); found: 573.9.

EXAMPLE 19f

4-[S-(3-Bromo-benzenesulfonyl)-N-(m-sulfonyl benzoic acid)-sulfoxamino]-5-methylsulfanyl-thiophene-2-carboxamidine trifluoroacetate

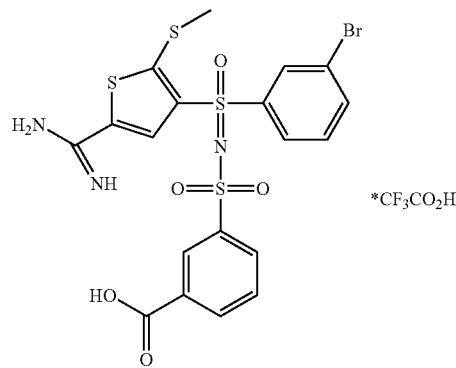

Trifluoroacetic acid (2.5 mL) was added to a 0° C. suspension of 4-[S-(3-bromo-benzenesulfonyl)-N-(m-sulfonyl benzoic acid tert-butyl ester)-sulfoxamino]-5-methylsulfanyl-thiophene-2-carboxamidine (Example 19: step e, 50.2 mg, 0.080 mmol) and Et$_3$SiH (31.8 μL, 0.199 mmol) in CH$_2$Cl$_2$ (5 mL). The reaction mixture was stirred at 0° C. for 1 hour, then warmed to RT and stirred for 4 hours. The solvents were removed in vacuo to afford a brown oil which was purified by preparatory HPLC (10-80% acetonitrile/ 0.1% trifluoroacetic acid in water over 30 minutes) to afford the title compound as a white solid (28.2 mg, 61.7% yield). $^1$H-NMR (CD$_3$OD): δ 8.37-8.39 (m, 1H), 8.32 (s, 1H), 8.20-8.23 (m, 1H), 8.05-8.11 (m, 2H), 7.99-8.02 (m, 1H), 7.89-7.92 (m, 1H), 7.52-7.66 (m, 2H), and 2.67 (s, 3H). ESI-MS (m/z): Calcd. for C$_{19}$H$_{23}$BrN$_3$O$_5$S$_4$: 573.9 (M+1); found: 573.8.

EXAMPLE 20

4-[S-(3-Bromo-benzenesulfonyl)-N-(p-sulfonyl benzoic acid)-sulfoxamino]-5-methylsulfanyl-thiophene-2-carboxamidine trifluoroacetate

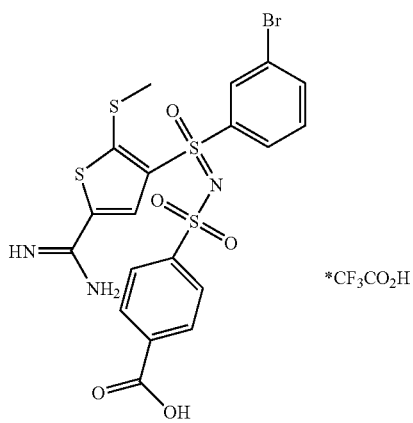

*CF$_3$CO$_2$H

EXAMPLE 20a

4-Sulfamoyl-benzoic acid tert-butyl ester

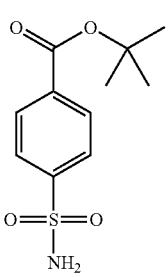

The procedure as in Example 19: step a was followed using 4-chlorosulfonyl-benzoic acid (2 g, 9.06 mmol), MgSO$_4$ (4.36 g, 36.22 mmol), H$_2$SO$_4$ (conc., 498 μL, 9.06 mmol), 2-methyl-propan-2-ol (anhydrous, 4.33 mL, 45.27 mmol), and CH$_2$Cl$_2$ (36 mL). Analogous workup was followed by column chromatography (silica gel, 50-100% ethyl acetate/hexanes) to afford the title compound as a white solid (500 mg, 21.5% yield). $^1$H-NMR (CDCl$_3$): δ 8.12 (d, 2H, J=8.8 Hz), 7.97 (d, 2H, J=8.8 Hz), 4.90 (bs, 2H), 1.61 (s, 9H).

EXAMPLE 20b (N-(p-Sulfonyl benzoic acid tert-butyl ester)imino)phenyliodinane

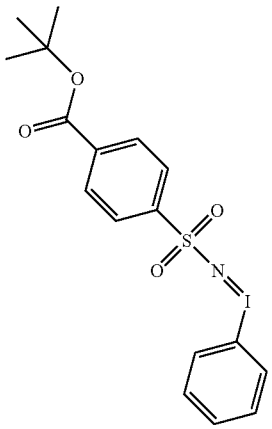

The procedure as in Example 19: step b was followed using 4-sulfamoyl-benzoic acid tert-butyl ester (Example 20: step a, 379 mg, 1.47 mmol), KOH (207 mg, 3.68 mmol), iodobenzenediacetate (474 mg, 1.47 mmol), and methanol (anhydrous, 5.89 mL) to afford a yellow solid (514 mg, 75.9% yield).

EXAMPLE 20c

4-[S-(3-Bromophenyl)-N-(p-sulfonyl benzoic acid tert-butyl ester)sufoxamino]-5-methylsulfanyl-thiophene-2-carbonitrile

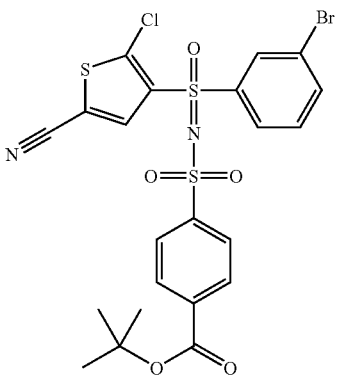

The procedure as in Example 19: step c was followed using 4-(3-bromo-benzenesulfinyl)-5-chloro-thiophene-2-carbonitrile (80 mg, 0.231 mmol), (N-(p-sulfonyl benzoic acid tert-butyl ester)imino)phenyliodinane (Example 20: step b, 212 mg, 0.462 mmol), Cu(OTf)$_2$ (8.35 mg, 0.023 mmol), and acetonitrile (anhydrous, 1 mL). Analogous work up was followed by column chromatography (silica gel, 20-30% ethyl acetate/hexanes) to afford the title compound as a white solid (92 mg, 66.2% yield). $^1$H-NMR (CDCl$_3$): δ 8.17-8.18 (m, 1H), 8.10-8.14 (m, 2H), 8.00-8.05 (m, 4H), 7.84-7.88 (m, 1H), 7.49-7.54 (m, 1H), 1.62 (s, 9H).

EXAMPLE 20d

4-[S-(3-Bromophenyl)-N-(p-sulfonyl benzoic acid tert-butyl ester)-sulfoxamino]-5-methylsulfanyl-thiophene-2-carboximidic acid methyl ester

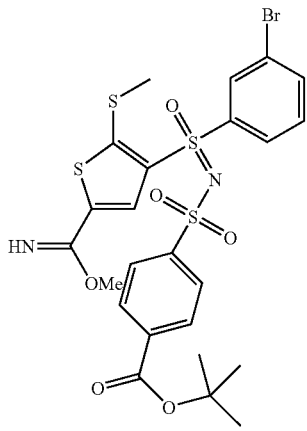

The procedure as in Example 19: step d was followed using 4-[S-(3-bromophenyl)-N-(p-sulfonyl benzoic acid tert-butyl ester)sufoxamino]-5-methylsulfanyl-thiophene-2-carbonitrile (Example 20: step c, 92 mg, 0.153 mmol), 0.1M NaSMe in methanol (1.83 mL, 0.183 mmol), and THF (anhydrous, 3 mL). The reaction mixture was warmed to RT and stirred overnight. The next day, the reaction mixture was cooled to −78° C. and 0.1M NaSMe in methanol (764 µL, 0.076 mmol) was added. The reaction mixture was stirred for 2 hours at −78° C., quenched with saturated NaHCO$_3$, and extracted into ethyl acetate. The organic layer was washed with saturated NaHCO$_3$, water, and brine, dried over magnesium sulfate, filtered, and concentrated in vacuo to afford the title compound as a yellow oil (47.7 mg, 48% yield). ESI-MS (m/z): Calcd. for $C_{24}H_{25}BrN_2O_6S_4$: 645.0 (M+1); found: 644.7.

EXAMPLE 20e

4-[S-(3-Bromo-benzenesulfonyl)-N-(p-sulfonyl benzoic acid tert-butyl ester)-sulfoxamino]-5-methyl-sulfanyl-thiophene-2-carboxamidine

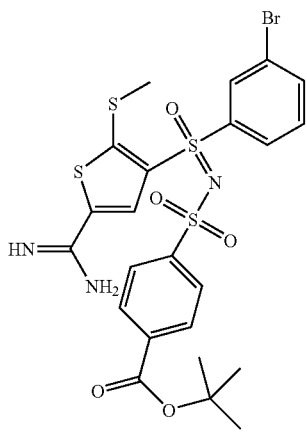

The procedure as in Example 19: step e was followed using 4-[S-(3-bromophenyl)-N-(p-sulfonyl benzoic acid tert-butyl ester)-sulfoxamino]-5-methylsulfanyl-thiophene-2-carboximidic acid methyl ester (Example 20: step d, 47.7 mg, 0.074 mmol), ammonium formate (25 mg, 0.396 mmol), and 2.0 M NH$_3$ in methanol (anhydrous, 5 ml). The reaction mixture was heated to 40° C. for 6 hours, then stirred overnight at RT. THF (0.5 mL) and TEA (0.5 mL) were added and the solvents were removed in vacuo to afford the title compound as a yellow oil (46.6 mg, quantitative). ESI-MS (m/z): Calcd. for $C_{23}H_{24}BrN_3O_5S_4$: 630.0 (M+1); found: 529.8.

EXAMPLE 20f

4-[S-(3-Bromo-benzenesulfonyl)-N-(p-sulfonyl benzoic acid)-sulfoxamino]-5-methylsulfanyl-thiophene-2-carboxamidine trifluoroacetate

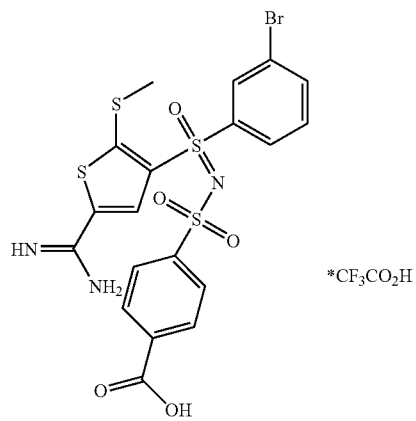

The procedure as in Example 19: step f was followed using 4-[S-(3-bromo-benzenesulfonyl)-N-(p-sulfonyl benzoic acid tert-butyl ester)-sulfoxamino]-5-methylsulfanyl-thiophene-2-carboxamidine (Example 20: step e, 46.6 mg, 0.074 mmol), Et$_3$SiH (29.5 µL, 0.185 mmol), trifluoroacetic acid (2.5 mL), and CH$_2$Cl$_2$ (5 mL). The crude was purified by preparatory HPLC (10-80% acetonitrile/0.1% trifluoroacetic acid in water over 30 minutes) to afford the title compound as a white solid (1.3 mg, 3.1% yield). $^1$H-NMR (CD$_3$OD): δ 8.32 (s, 1H), 8.10-8.15 (m, 3H), 8.02-8.06 (m, 1H), 7.91-7.96 (m, 3H), 7.54-7.60 (m, 1H), 2.70 (s, 3H). ESI-MS (m/z): Calcd. for $C_{19}H_{16}BrN_3O_5S_4$: 573.9 (M+1); found: 573.8.

EXAMPLE 21

4-[S-(3-Bromophenyl)-N-(2-pyridinesulfonyl)-sulfoxamino]-5-methylsulfanyl-thiophene-2-carboxamidine bis trifluoroacetate

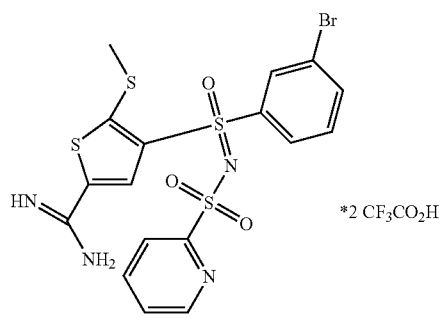

EXAMPLE 21a

4-[S-(3-Bromophenyl)-N-(2-pyridinesulfonyl)sulfoxamino]-5-methylsulfanyl-thiophene-2-carbamic acid tert-butyl ester

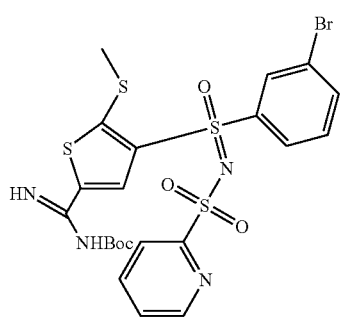

Pyridine-2-sulfonyl chloride (Combiblocks, 14.1 mg, 0.066 mmol) was added to a suspension of 4-[S-(3-bromophenyl)-sulfoxamino]-5-methylsulfanyl-thiophene-2-carbamic acid tert-butyl ester (Example 24: step j, 26.9 mg, 0.055 mmol) and triethylamine (Aldrich, 22.9 µL, 0.16 mmol) in CH$_2$Cl$_2$ (36 mL). The reaction mixture was stirred overnight at room temperature and then additional pyridine-2-sulfonyl chloride (Combiblocks, 35.2 mg, 0.16 mmol) and TEA (Aldrich, 68.8 µL, 0.49 mmol) were added. After stirring for 3 days, the mixture was concentrated in vacuo to afford the title compound as a red oil (8.66 mg, 25% yield). ESI-MS (m/z): Calcd. for C$_{23}$H$_{23}$BrN$_4$O$_5$S$_4$: 530.9 (M-Boc); found: 530.9.

EXAMPLE 21b

4-[S-(3-Bromophenyl)-N-(2-pyridinesulfonyl)-sulfoxamino]-5-methylsulfanyl-thiophene-2-carboxamidine bis trifluoroacetate

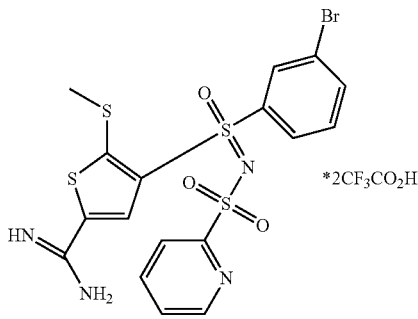

Trifluoroacetic acid (2 mL) was added to 4-[S-(3-bromophenyl)-N-(sulfonyl 2-pyridyl)sulfoxamino]-5-methylsulfanyl-thiophene-2-carbamic acid tert-butyl ester (Example 21: step a, 8.66 mg, 0.014 mmol) in CH$_2$Cl$_2$ (2 mL) at room temperature. The reaction mixture was stirred for 2 hours, concentrated in vacuo, and purified by preparatory HPLC (10-80% acetonitrile/0.1% trifluoroacetic acid in water over 30 minutes) to afford the title compound as a white solid (1.4 mg, 19.2% yield). $^1$H-NMR (CD$_3$OD): δ 8.63-8.65 (m, 1H), 8.41 (s, 1H), 8.16-8.17 (m, 1H), 8.01-8.06 (m, 2H), 7.95-7.98 (m, 1H), 7.92 (dm, 1H, J=8.0 Hz), 7.62-7.66 (m, 1H), 7.56 (t, 1H, J=8.0 Hz), and 2.69 (s, 3H). ESI-MS (m/z): Calcd. for C$_{17}$H$_{15}$BrN$_4$O$_3$S$_4$: 530.9 (M+1); found: 530.9.

EXAMPLE 22

Synthesis of 4-[S-(3-Bromophenyl)-N-(m-sulfonyl pyridyl)-sulfoxamino]-5-methylsulfanyl-thiophene-2-carboxamidine bis trifluoroacetate

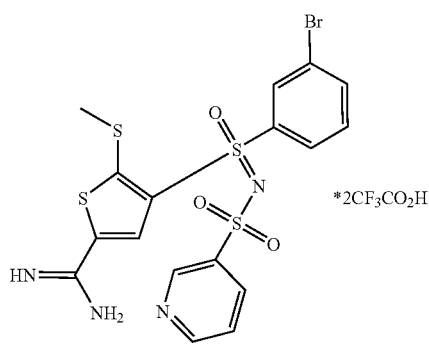

EXAMPLE 22a

4-[S-(3-Bromophenyl)-N-(m-sulfonyl pyridyl)sulfoxamino]-5-methylsulfanyl-thiophene-2-carbamic acid tert-butyl ester

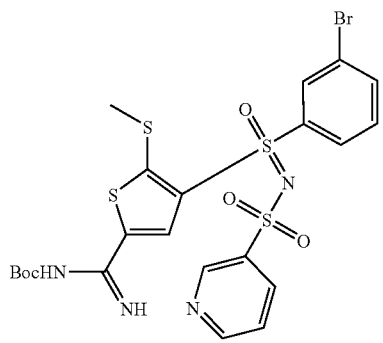

The procedure as in Example 21: step a was followed using 4-[S-(3-bromophenyl)-sulfoxamino]-5-methylsulfanyl-thiophene-2-carbamic acid tert-butyl ester (Example 24: step j, 27.8 mg, 0.057 mmol), pyridine-3-sulfonyl chloride hydrochloride (Chemical Synthesis Services, 51 mg, 0.24 mmol), TEA (94.8 µL, 0.68 mmol), and CH$_2$Cl$_2$ (2 mL). Analogous workup afforded the title compound as a red oil (10.7 mg, 30% yield). ESI-MS (m/z): Calcd. for C$_{23}$H$_{23}$BrN$_4$O$_5$S$_4$: 530.9 (M-Boc); found: 530.9.

EXAMPLE 22b

4-[S-(3-Bromo-benzenesulfonyl)-N-(3-pyridine-sulfonyl)-sulfoxamino]-5-methylsulfanyl-thiophene-2-carboxamidine bistrifluoroacetate

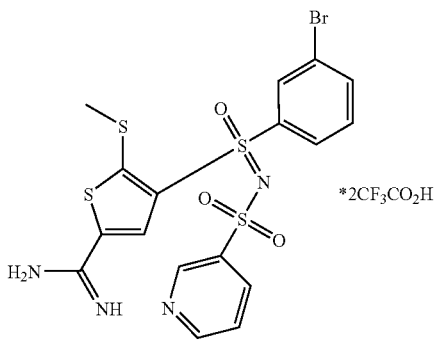

The procedure as in Example 21: step b was followed using 4-[S-(3-bromophenyl)-N-(m-sulfonyl pyridyl)sulfoxamino]-5-methylsulfanyl-thiophene-2-carbamic acid tert-butyl ester (Example 22: step a, 10.7 mg, 0.017 mmol), TFA (2 mL), and $CH_2Cl_2$ (2 mL). Analogous workup and purification afforded the title compound as a white solid (4.3 mg, 47.8% yield). $^1$H-NMR ($CD_3OD$): δ 8.95-9.04 (m, 1H), 8.75-8.85 (m, 1H), 8.39 (s, 1H), 8.27-8.33 (m, 1H), 8.05-8.19 (m, 2H), 7.95-7.98 (m, 1H), 7.57-7.70 (m, 2H), and 2.72 (s, 3H). ESI-MS (m/z): Calcd. for $C_{17}H_{15}BrN_4O_3S_4$: 530.9 (M+1); found: 530.9.

EXAMPLE 23

Synthesis of 4-[S-(3-Bromophenyl)-N-(phenyl)-sulfoxamino]-5-methylsulfanyl-thiophene-2-carboxamidine trifluoroacetate

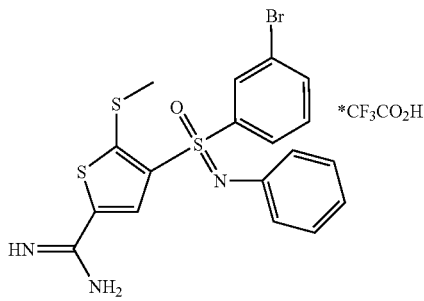

EXAMPLE 23a

4-[S-(3-Bromophenyl)-N-(phenyl)sulfoxamino]-5-methylsulfanyl-thiophene-2-carbamic acid tert-butyl ester

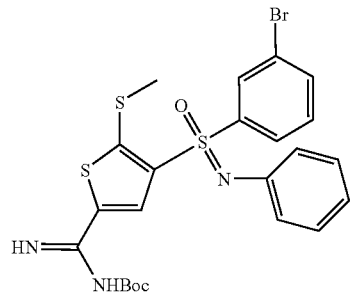

4-[S-(3-Bromophenyl)-sulfoxamino]-5-methylsulfanyl-thiophene-2-carbamic acid tert-butyl ester (Example 24: step j, 10 mg, 0.020 mmol), phenyl boronic acid (Aldrich, 4.97 mg, 0.041 mmol), [1,10]phenanthroline (Aldrich, 3.78 mg, 0.021 mmol), and copper (II) acetate (Aldrich, 3.70 mg, 0.020 mmol) were stirred in $CH_2Cl_2$ (1 mL) over 3 days at room temperature. The mixture was concentrated in vacuo and purified by preparatory thin layer chromatography (silica gel, 30-40% ethyl acetate/hexanes) to afford the title compound as a white solid (4.1 mg, 35% yield). $^1$H-NMR ($CDCl_3$): δ 8.24-8.27 (m, 1H), 8.01-8.06 (m, 1H), 7.88 (s, 1H), 7.65-7.70 (m, 1H), 7.33-7.38 (m, 1H), 7.10-7.20 (m, 4H), 6.92-6.97 (m, 1H), 2.55 (s, 3H) and 1.52 (s, 9H).

EXAMPLE 23b

4-[S-(3-Bromophenyl)-N-(phenyl)-sulfoxamino]-5-methylsulfanyl-thiophene-2-carboxamidine trifluoroacetate

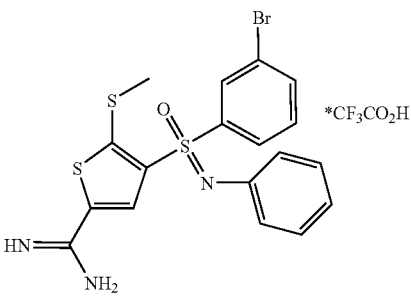

The procedure as in Example 19: step f was followed using 4-[S-(3-bromophenyl)-N-(phenyl)sulfoxamino]-5-methylsulfanyl-thiophene-2-carbamic acid tert-butyl ester (Example 23: step a, 4.1 mg, 0.072 mmol), TFA (2 mL), and $CH_2Cl_2$ (2 mL). Analogous workup and purification afforded the title compound as a white solid (1.7 mg, 50% yield). $^1$H-NMR ($CD_3OD$): δ 8.34 (s, 1H), 8.29-8.31 (m, 1H), 8.13 (dm, 1H, J=8.0 Hz), 7.84 (dm, 1H, J=8.0 Hz), 7.51 (t, 1H, J=8.0 Hz), 7.11-7.19 (m, 4H), 6.92-6.97 (m, 1H), and 2.69 (s, 3H). ESI-MS (m/z): Calcd. for $C_{18}H_{16}BrN_3OS_3$: 466.0 (M+1); found: 465.9.

EXAMPLE 24

4-[S-(3-Bromophenyl)-sulfoximino]-5-methylsulfanyl-thiophene-2-carbamic acid tert-butyl ester

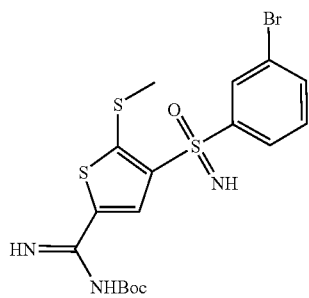

EXAMPLE 24a

4-Bromo-5-chloro-thiophene-2-carbaldehyde

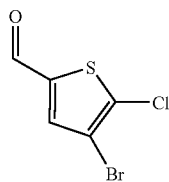

To a −78° C. solution of 3-bromo-2-chloro-thiophene (10.03 g, 50.79 mmol) in THF (anhydrous, 100 mL) was added lithium diisopropyl amide solution (Aldrich, 2.0M in heptane/THF/ethylbenzene, 38.1 mL, 76.20 mmol) dropwise over 45 minutes under argon. The reaction mixture was stirred for one hour at −78° C., treated with DMF (Aldrich, anhydrous, 19.7 mL, 254.40 mmol), stirred for 15 minutes at −78° C., warmed to room temperature, and stirred for 45 minutes. Aqueous citric acid was added and the reaction mixture was stirred for 5 minutes. The mixture was diluted with ethyl acetate and was washed with saturated NaHCO$_3$, water, and brine. The organic layer was dried over magnesium sulfate, filtered, concentrated in vacuo, and purified by column chromatography (silica gel, 1-3% ethyl acetate/hexanes) to afford the title compound as a yellow solid (10.63 g, 92.8% yield).

EXAMPLE 24b

4-Bromo-5-chloro-thiophene-2-carbonitrile

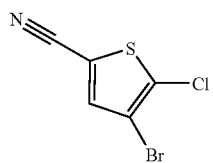

Hydroxylamine hydrochloride (Aldrich, 4.91 g, 70.66 mmol) and triethylamine (anhydrous, 11.2 mL, 80.36 mmol) were added to a 0° C. solution of 4-bromo-5-chloro-thiophene-2-carbaldehyde (Example 24: step a, 10.63 g, 47.14 mmol) in acetonitrile (anhydrous, 250 mL). The reaction mixture was warmed to room temperature and stirred for 1 hour. Phthalic anhydride was added and the reaction mixture was heated to 80° C. overnight. The mixture was cooled to room temperature, diluted with ethyl acetate (400 mL), and washed with aqueous citric acid, saturated NaHCO$_3$, water, and brine. The organic layer was dried over magnesium sulfate, filtered, concentrated in vacuo, and purified by column chromatography (silica gel, 5% ethyl acetate/hexanes) to afford the title compound as a pale yellow solid (9.76 g, 93% yield). $^1$H-NMR (CDCl$_3$): δ 7.47 (s, 1H).

EXAMPLE 24c bis-3-Bromophenyldisulfide

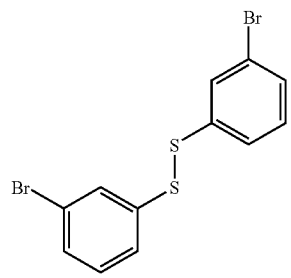

Pyridinium chlorochromate (Aldrich, 11.2 g, 51.96 mmol) was added portionwise to a 0° C. solution of 3-bromobenzenethiol (Aldrich, 6.14 mL, 51.92 mmol) in CH$_2$Cl$_2$ (100 mL). The reaction was stirred at room temperature for 1 hour and then quenched with silica gel for 10 minutes. The slurry was filtered through Celite, which was subsequently washed with hexanes (250 mL). The filtrate was concentrated in vacuo to afford the title compound as a brown oil (8.9 g, 91% yield).

EXAMPLE 24d

3-Bromo-benzenesulfinic acid methyl ester

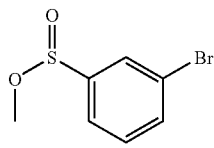

Bromine (Aldrich, 3.65 mL, 71.03 mmol) was added dropwise over 30 minutes to a room temperature solution of bis-3-bromophenyldisulfide (Example 24: step c, 8.9 g, 23.66 mmol) and sodium carbonate (Aldrich, 12.54 g, 118.31 mmol) in methanol (anhydrous, 100 mL). The reaction mixture was stirred overnight and then concentrated in vacuo. The residue was diluted with ethyl acetate (300 mL) and was washed with saturated NaHCO$_3$, water, and brine. The organic layer was dried over magnesium sulfate, filtered, concentrated in vacuo, and purified by column chromatography (silica gel, 10-15% ethyl acetate/hexanes) to afford the title compound as a pale yellow oil (9.8 g, 88% yield). $^1$H-NMR (CDCl$_3$): δ 7.87-7.77 (m, 1H), 7.71 (dm, 1H, J=7.9 Hz), 7.65 (dm, 1H, J=7.8 Hz), 7.45 (t, 1H, J=7.8 Hz), and 3.53 (s, 3H).

EXAMPLE 24e 4-(3-Bromo-benzenesulfinyl)-5-chloro-thiophene-2-carbonitrile

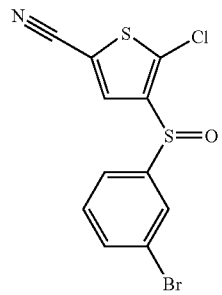

Isopropyl magnesium chloride solution (Aldrich, 2.0 M in THF, 2.92 mL, 5.84 mmol) was added dropwise over 1.5 hours to a −78° C. suspension of 4-bromo-5-chloro-thiophene-2-carbonitrile (Example 24: step b, 1 g, 4.49 mmol) in THF (anhydrous, 20 mL) under argon. The reaction mixture was treated with 3-bromo-benzenesulfinic acid methyl ester solution (Example 24: step d, 1 g, 4.49 mmol, 10 mL of THF) in one portion at −78° C. and then stirred overnight at room temperature. Saturated ammonium chloride solution was added to the mixture and stirred for 30 minutes at room temperature. The reaction mixture was diluted with ethyl acetate and washed with water and brine. The organic layer was dried over magnesium sulfate, filtered, concentrated in vacuo, and purified by column chromatography (silica gel, 15-25% ethyl acetate/hexanes) to afford the title compound as a light yellow solid (1.33 g, 85% yield). $^1$H-NMR (CDCl$_3$): δ 7.86-7.88 (m, 1H), 7.69 (dm, 1H, J=7.9 Hz), 7.64 (dm, 1H, J=7.9 Hz), 7.62 (s, 1H), 7.42 (t, 1H, J=7.9 Hz).

EXAMPLE 24f (N-(p-Nitrosulfonylbenzene)imino)phenyl iodinane

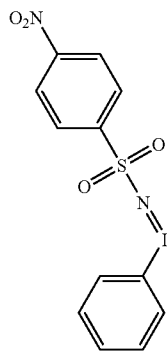

Potassium hydroxide (Aldrich, 5.95 g, 106.09 mmol) was added to a suspension of 4-nitro-benzenesulfonamide (Aldrich, 8.85 g, 42.4 mmol) in methanol (anhydrous, 100 mL). After stirring for 30 minutes, the reaction mixture was purged with argon and then treated with iodobenzene diacetate (Aldrich, 13.67 g, 42.4 mmol). The reaction mixture was stirred overnight at room temperature and then the solids were filtered and dried overnight in a vacuum oven to afford the title compound as a yellow solid (15.32 g, 89% yield).

EXAMPLE 24g

4-[S-(3-Bromophenyl)-N-(sulfonyl-p-nitrobenzene)-sufloximino]-5-Chloro-thiophene-2-carbonitrile

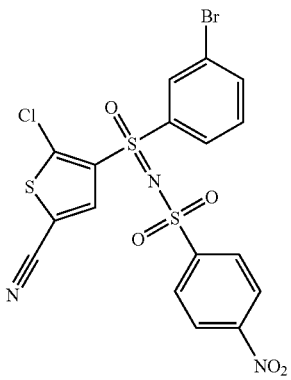

Copper (II) trifluoromethanesulfonate (Aldrich, 278 mg, 0.77 mmol) was added to a suspension of 4-(3-bromo-benzenesulfinyl)-5-chloro-thiophene-2-carbonitrile (Example 24: step e, 1.33 g, 3.84 mmol) and (N-(p-nitrosulfonylbenzene)imino)phenyl iodinane (Example 24: step f, 1.86 g, 4.60 mmol) at room temperature under argon. The reaction mixture was stirred at room temperature for 2 hours, and then filtered. The isolated solid was washed with water, dissolved in THF (50 mL), and concentrated in vacuo to afford the title compound as a light yellow solid (1.89 g, 90% yield). $^1$H-NMR (CDCl$_3$): δ 8.33-8.37 (m, 2H), 8.15-8.20 (m, 3H), 8.04 (s, 1H), 8.01 (dm, 1H, J=8.1 Hz), 7.87 (dm, 1H, J=8.0 Hz), 7.52 (t 1H, J=8.1 Hz).

EXAMPLE 24h

4-[S-(3-Bromophenyl)-sulfoximino]-5-methylsulfanyl-thiophene-2-carboximidic acid methyl ester

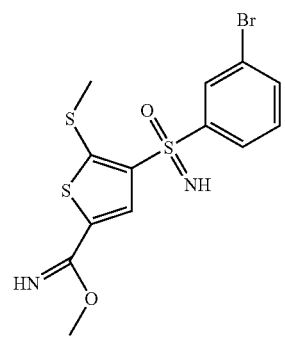

Sodium thiomethoxide solution (1.0 M in methanol, 2.00 mL, 2.00 mmol) was added dropwise over 1 hour to a −78° C. suspension of 4-[S-(3-bromophenyl)-N-(sulfonyl-p-nitrobenzene)-sufloximino]-5-methylsulfanyl-thiophene-2-carbonitrile (Example 24: step g, 1.03 g, 1.88 mmol) in THF (anhydrous, 10 mL) under argon. The reaction was warmed to room temperature and stirred overnight. Additional sodium thiomethoxide solution (1.0 M in methanol, 4.0 mL) was added dropwise over 6 hours at room temperature under argon. Saturated sodium bicarbonate solution (15 mL) was added and the mixture was stirred for 15 minutes at room temperature. The mixture was diluted with ethyl acetate, and then washed with water and brine. The organic layer was dried over magnesium sulfate, filtered, and concentrated in vacuo to afford the title compound as a yellow oil (764 mg, quantitative). ESI-MS (m/z): Calcd. for $C_{13}H_{13}BrN_2O_2S_3$: 404.9 (M+1); found: 404.9.

EXAMPLE 24i

4-[S-(3-Bromophenyl)-sulfoximino]-5-methylsulfanyl-thiophene-2-carboxamidine

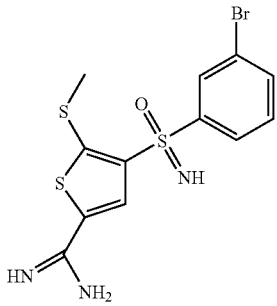

A mixture of ammonium formate (Aldrich, 238 mg, 3.77 mmol) and 4-[S-(3-bromophenyl)-sulfoximino]-5-methylsulfanyl-thiophene-2-carboximidic acid methyl ester (Example 24: step h, 764 mg, 1.88 mmol) in 2.0 M $NH_3$ in methanol (anhydrous, 10 mL) and was heated to 40° C. for 7 hours, then stirred overnight at room temperature under argon. The reaction mixture was treated with THF (0.5 mL) and TEA (0.5 mL) and concentrated in vacuo to afford a yellow oil (680 mg, quantitative). ESI-MS (m/z): Calcd. for $C_{12}H_{12}BrN_3OS_3$: 389.9 (M+1); found: 389.9.

EXAMPLE 24j

4-[S-(3-Bromophenyl)-sulfoximino]-5-methylsulfanyl-thiophene-2-carbamic acid tert-butyl ester

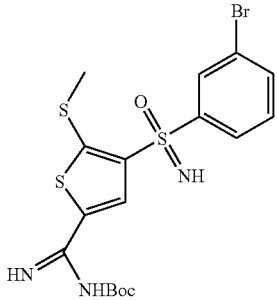

Di-tert-butyl dicarbonate (Aldrich, 1.14 g, 5.23 mmol) and N,N-ethyldiisopropyl-amine (910 µL, 5.22 mmol) were added at room temperature to a suspension of 4-[S-(3-bromophenyl)-sulfoximino]-5-methylsulfanyl-thiophene-2-carboxamidine (Example 24: step i, 680 mg, 1.88 mmol) in THF (anhydrous, 15 mL). The reaction mixture was stirred overnight at room temperature. Additional di-tert-butyl dicarbonate (1.14 g, 5.23 mmol) and DIEA (910 µL, 5.22 mmol) were added and the mixture was stirred overnight. Methanol (2 mL), water (1 mL), di-tert-butyl dicarbonate (1.14 g, 5.23 mmol), and DIEA (910 µL, 5.22 mmol) were added and the mixture was stirred overnight. The mixture was concentrated in vacuo and purified by column chromatography (silica gel, 50% ethyl acetate/hexanes) to afford the title compound as a light yellow solid (300 mg, 35% yield). $^1$H-NMR (CDCl$_3$/CD$_3$OD): δ 8.18-8.19 (m, 1H), 7.99 (dm, 1H, J=7.9 Hz), 7.93 (s, 1H), 7.70 (dm, 1H, J=8.0 Hz), 7.38 (t, 1H, J=8.0 Hz), 2.56 (s, 3H), and 1.50 (s, 9H).

EXAMPLE 25

4-[S-(3-Bromophenyl)-N-Tosylsulfoximino]-5-methylsulfanyl-thiophene-2-carboxamidine trifluoroacetate

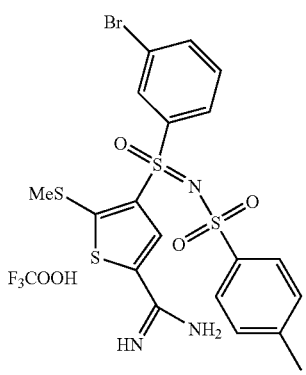

EXAMPLE 25a (N-(p-Toluenesulfonyl)imino)phenyliodinane

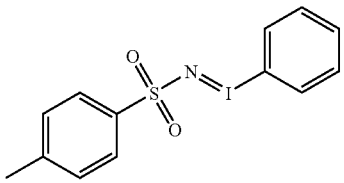

Diacetoxyiodobenzene (12.88 g, 40 mmol) was added to a solution of KOH (5.61 g, 100 mmol) and p-toluenesulfonamide (6.85 g, 40 mmol) in methanol (160 mL) at 8° C. A yellow color developed within 1 minute. The cooling bath was removed, and the solution was allowed to warm to RT with stirring for 3 hours. Water (180 mL) was added and the reaction was refrigerated overnight. The precipitate was collected by filtration and dried overnight in a vacuum dessicator to yield 10 g (66%) of a light yellow solid which was used with out further purification or characterization.

EXAMPLE 25b

4-Bromo-5-nitro-thiophene-2-carbaldehyde

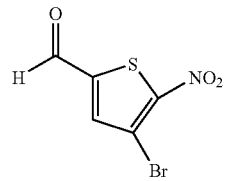

A 5-L, three-neck, round bottom flask was equipped with a mechanical stirrer and temperature probe and charged with 3-bromothiphenecarboxyaldehyde (360.0 g, 1.884 mmol) and $H_2SO_4$ (1.5 L). The flask was cooled to 0° C. using an ice/NaCl bath. In a separate round-bottom flask, $KNO_3$ (209.5 g, 2.076 mol) was dissolved in $H_2SO_4$ (1 L). This solution was transferred to an addition funnel and added to the thiophene over a 2 hour period while maintaining the internal temperature below 4° C. After 30 minutes from the end of the addition, the reaction was complete by TLC analysis (2:1 heptane/EtOAc). A 20 L glass carboy was charged with approximately 10 kg of ice and equipped with a pneumatic stirrer. The reaction mixture was poured slowly into the ice and washed with $H_2O$ (3 L), then heptane (3 L) and dried in a vacuum oven to yield the title compound as a tan solid (426.2 g, 96%). $^1$H-NMR ($CDCl_3$): δ 9.9 (1H, s), 8.8 (s, 1H).

EXAMPLE 25c

4-Bromo-5-nitro-thiophene-2-carbaldehyde oxime

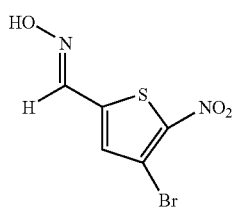

A 12-L three neck, round bottom flask equipped with mechanical stirring, a temperature probe and a reflux condenser was charged with 4-Bromo-5-nitro-thiophene-2-carbaldehyde (Example 25: step b, 426.0 g, 1.805 mol), absolute ethanol (4L) and pyridine (189.9 mL, 2.35 mol). Hydroxylamine hydrochloride (163.3 g, 2.35 mol) was added in one portion and the mixture was heated. The mixture became a slurry at 27° C., turned clear at 50° C. and was refluxed at 80° C. for 1.5 hour. TLC analysis showed reaction completion (2:1 heptane/EtOAc). The cooled reaction mixture was concentrated in vaccuo then dried azeotrophically using toluene (1L). The resulting moist solids were transferred to a 10-L glass carboy and stirred with $H_2O$ (3L). After 1 hour, the solids were isolated by filtration, rinsed with $H_2O$ (3L) and heptane (3L), then dried in vacuum oven to give the desired title compound as a brown powder (441.65 g, 97%). $^1$H-NMR (DMSO): δ 13.0 (1H, br s), 8.1 (1H, s), 7.8 (1H, s).

EXAMPLE 25d

4-Bromo-5-nitro-thiophene-2-carbonitrile

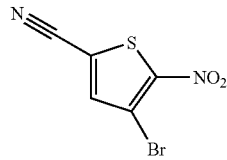

A 5-L, three neck, round bottom flask equipped with a temperature probe, mechanical stirrer, and a reflux condenser was charged with 4-Bromo-5-nitro-thiophene-2-carbaldehyde oxime (Example 25: step c; 441.0 g, 1.76 mol). Acetic anhydride (2.5 L) was added causing an endothermic reaction from 22° C. to 17° C. The resulting yellow slurry was heated to reflux. At 100° C. the reaction became a black solution. After 2 hours at 130° C., TLC analysis (2:1 heptane/EtOAc) showed reaction completion and the heat was removed. The mixture was transferred to a rotary evaporator and concentrated to dryness. The residue was diluted with $CH_2Cl_2$ (3L), and $H_2O$ (3L). The layers were separated and the organic layer was washed with $H_2O$ (3L), dried over $MgSO_4$, and concentrated to give the desired title compound as a tan solid (350.85 g, 86%). $^1$H-NMR (DMSO): δ 8.3 (1H, s).

EXAMPLE 25e 4-(3-Bromo-benzenesulfinyl)-5-nitro-thiophene-2-carbonitrile

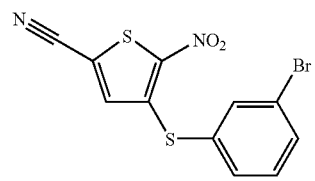

A 12-L, three neck, round bottom flask equipped with a mechanical stirrer and temperature probe was charged with 4-Bromo-5-nitro-thiophene-2-carbonitrile (Example 25: step d; 273 g, 1.174 mol), 3-bromothiophenol (127 mL, 1.232 mol) and THF (4L). A cold water bath was added. Triethylamine (172 mL, 1.232 mol) was charged to a 250 mL addition funnel and added dropwise to the mixture over 45 min, resulting in a temperature increase from 16.9° C. to 22.3° C. After 1 hour, the reaction was complete and transferred in portions to a 5-L rotary evaporator bulb and concentrated to dryness under vacuum. The solids were transferred to a 10-L glass carboy, diluted with EtOAc (2L) and satd. $NaHCO_3$ (2L) and stirred vigorously. The resulting solid precipitate was removed by filtration, washed with $H_2O$ (1L) and dried in a vacuum oven resulting in the title compound as a bright yellow powder (241.56 g, 60%). $^1$H-NMR (DMSO): δ 8.0 (1H, s), 7.8 (1H, d), 7.6 (1H, d), 7.3 (1H, t), 7.1 (1H, s).

EXAMPLE 25f

5-Amino-4-(3-bromo-phenylsulfanyl)-thiophene-2-carbonitrile

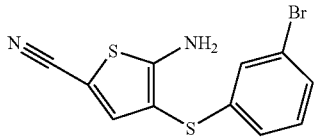

4-(3-Bromo-benzenesulfinyl)-5-nitro-thiophene-2-carbonitrile (Example 25: step e; 5.20 g, 15.33 mmol) was dissolved into EtOH (45 mL) and acetic acid (5 mL). The reaction was heated to 50° C. and then iron (4.28 g, 76.69 mmol) was added and the reaction was allowed to heat with stirring overnight. The reaction mixture was filtered through celite which was washed with MeOH and EtOAc to ensure that the product does not remain on the celite. The filtrate was concentrated and then dissolved into EtOAC and washed with brine. The organic layer was dried (MgSO$_4$) and concentrated. The crude reaction mixture was purified by flash column (20% EtOAc in Hexanes) resulting in the desired product as a brown oil (1.5 g, 32%). $^1$H-NMR (CDCl$_3$): δ 7.38 (1H, s), 7.31-7.29 (1H, m), 7.18 (1H, t, J=1.8, Hz), 7.14 (1H, t, J=7.9 Hz), 6.99-6.96 (1H, m), 5.06 (2H, br s).

EXAMPLE 25g

5-Bromo-4-(3-bromo-phenylsulfanyl)-thiophene-2-carbonitrile

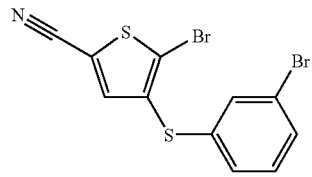

Copper (II) bromide (0.54 g, 2.43 mmol) was dissolved in acetonitrile (10 mL). To this solution was added t-butylnitrite (388 µL, 3.26 mmol), slowly while warming to 50° C. A brown gas formed in the reaction flask and was continued to heat at 50° C. for 30 minutes. To this reaction mixture was added a solution of 5-Amino-4-(3-bromo-phenylsulfanyl)-thiophene-2-carbonitrile (Example 25: step f; 0.50 g, 1.63 mmol) in acetonitrile (2 mL). The reaction was heated to 80° C. for 30 minutes. The reaction mixture was concentrated and then purified by flash column chromatography (100% hexane to 20% EtOAc in hexane). The product was isolated as a yellow solid (246 mg, 40%). $^1$H-NMR (CDCl$_3$): δ 7.45-7.43 (2H, m), 7.33 (1H, s), 7.33 (1H, s), 7.24-7.19 (1H, m).

EXAMPLE 25h

5-Bromo-4-(3-bromo-benzenesulfinyl)-thiophene-2-carbonitrile

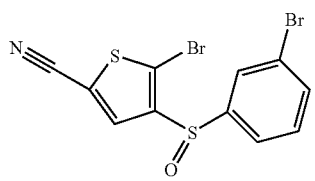

To a solution of 5-Bromo-4-(3-bromo-phenylsulfanyl)-thiophene-2-carbonitrile (Example 25: step g; 292 mg, 0.78 mmol) in AcOH (3 mL), 30% H$_2$O$_2$ (85 µL, 0.94 mmol) was added slowly and warmed to 50° C. for 2 hours. The reaction was concentrated and then dissolved in EtOAc and washed with water. The organic layer was dried (MgSO$_4$) and concentrated. The compound was used without further purification. $^1$H-NMR (CDCl$_3$): δ 7.87-7.85 (1H, m), 7.64 (2H, t, J=10.1, Hz), 7.57 (1H, s), 7.41 (1H, t, 7.91 Hz).

EXAMPLE 25i

5-Bromo-4-[S-(3-Bromophenyl)-N-Tosylsulfoximino]-thiophene-2-carbonitrile

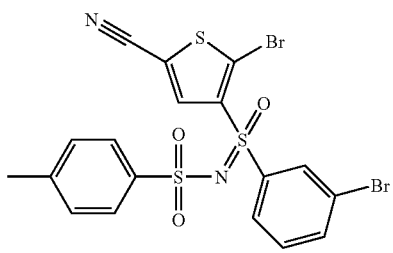

To a solution of 5-Bromo-4-(3-bromo-benzenesulfinyl)-thiophene-2-carbonitrile (Example 25: step h; 322 mg, 0.95 mmol) and (N-(p-Toluenesulfonyl)imino)phenyliodinane (Example 3: step a; 388 mg, 1.04 mmol) in acetonitrile (4 mL) was added copper (II) trifluoromethanesulfonate (34.4 mg, 0.095 mmol). The reaction turned pale green and was stirred at RT overnight. The reaction mixture was concentrated and then dissolved in EtOAc and filtered to remove copper salts. Purification by flash column chromatography (10% EtOAc in Hexane) yielded the desired product as a white solid (182 mg, 34%). $^1$H-NMR (CDCl$_3$): δ 8.18 (1H, t, J=1.9 Hz), 8.02-8.00 (1H, m), 8.01 (1H, s), 7.86-7.82 (4H, m), 7.48 (1H, t, J=8.1 Hz), 7.31 (1H, m), 2.43 (3H, s).

EXAMPLE 25j

4-[S-(3-Bromophenyl)-N-Tosylsulfoximino]-5-methylsulfanyl-thiophene-2-carbonitrile

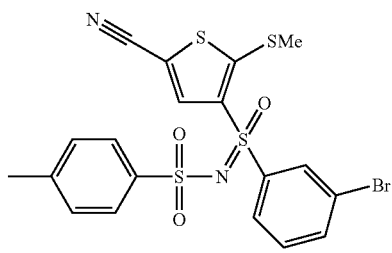

To a solution of 4-[S-(3-Bromophenyl)-N-Tosylsulfoximino]-5-bromo-thiophene-2-carbonitrile (Example 25: step i; 50 mg, 0.090 mmol) in THF (3 mL) was added 1.0 M NaSMe in EtOH at −78° C. slowly and stirred for 2 hours. The reaction was purified by prep plate TLC (50% EtOAc in hexanes). The desired compound was isolated as a solid (11 mg, 23%). $^1$H-NMR (CDCl$_3$): δ 8.43 (1H, d, J=1.4 Hz), 8.12 (1H, t, J=1.82 Hz), 7.99-7.96 (1H, m), 7.83-7.79 (3H, m), 7.77-7.76 (1H, d, J=1.53 Hz), 7.48 (1H, t, J=8.0 Hz), 7.30 (1H, m), 2.45 (3H, s), 2.43 (3H, s).

EXAMPLE 25k

4-[S-(3-Bromophenyl)-N-Tosylsulfoximino]-5-methylsulfanyl-thiophene-2-carboxamidine trifluoroacetate

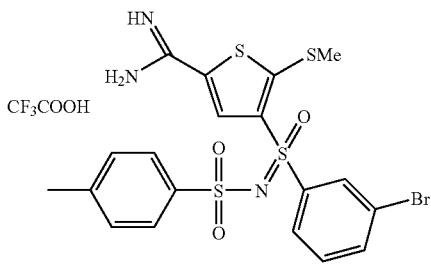

To a solution of 4-[S-(3-Bromophenyl)-N-Tosylsulfoximino]-5-methylsulfanyl-thiophene-2-carbonitrile (Example 25: step j; 5 mg, 0.009 mol) in MeOH (300 μL) and DCM (10 μL) was added sodium methoxide (2 μL, 0.009 mol) and stirred at RT for 10 minutes. The reaction was complete by ESI-MS (m/z): Calcd. For C$_{20}$H$_{19}$BrN$_2$O$_4$S$_4$: 557.9; found: 558.9, resulting in the formation of 4-[S-(3-Bromophenyl)-N-Tosylsulfoximino]-5-methylsulfanyl-thiophene-2-carboximidic acid methyl ester. To the 4-(4-Toluenesulfonyl-3-Bromo-benzenesulfoxamine)-5-methylsulfanyl-thiophene-2-carboximidic acid methyl ester intermediate formed, was added ammonia in methanol (7N) (2 μL, 0.009 mol) and the reaction was stirred for 2 hours. To this was added ammonium formate (NH$_4$HCO$_2$) (6 mg, 0.09 mol) and the reaction was stirred an additional 13 hours. The solvents were removed in vacuo followed by C$_{18}$-HPLC (5-60% CH$_3$CN/0.1% TFA water over 20 minutes). The final compound was isolated as a solid (1.8 mg, 30%). $^1$H-NMR (CD$_3$OD): δ 8.29 (1H, s), 8.08 (1H, t, J=1.90 Hz), 8.04-8.01 (1H, m), 7.93-7.91 (1H, m), 7.71 (2H, d, J=8.3 Hz), 7.56 (1H, d, J=8.1 Hz), 7.32 (2H, d, J=7.96 Hz), 2.71 (3H, s), 2.43 (3H, s).

EXAMPLE 26

4-(3-Bromo-benzenesulfoxamine)-5-methylsulfanyl-thiophene-2-carboxamidine

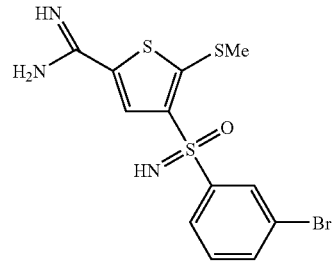

EXAMPLE 26a 4-(3-Bromo-benzenesulfoximine)-5-methylsulfanyl-thiophene-2-carboamide

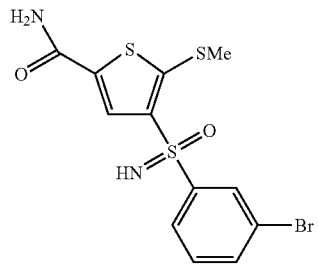

To 4-[S-(3-Bromophenyl)-N-Tosylsulfoximino]-5-methylsulfanyl-thiophene-2-carbonitrile (Example 25: step j, 47 mg, 0.09 mmol) was added concentrated H$_2$SO$_4$ (1 mL) and then stirred at RT for 24 hours. The reaction was complete by ESI-MS (m/z): Calcd. For C$_{12}$H$_{11}$BrN$_2$O$_2$S$_3$: 389.9; found: 391.0. The reaction was quenched by slowly adding water with stirring until the water was clear followed with extraction with EtOAc. The organic layer was dried and concentrated in vacuo followed by purification by flash column chromatography (50% Hexane/EtOAc to 100% EtOAc) which yielded the title compound (20 mg, 67%). $^1$H-NMR (CDCl$_3$): δ 8.12 (1H, t, J=1.9 Hz), 7.95-7.92 (1H, m), 7.81 (1H, s), 7.65-7.62 (1H, m), 7.32 (1H, t, J=7.93 Hz), 2.45 (3H, s).

EXAMPLE 26b 4-(3-Bromo-benzenesulfoximine)-5-methylsulfanyl-thiophene-2-carboxamidine

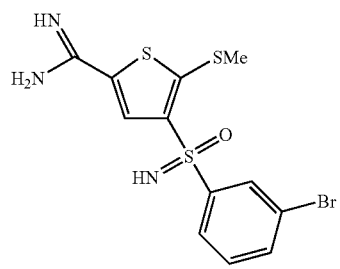

A solution of trimethyl aluminum (2.0 M in toluene) (1.54 mL, 3.07 mmol) was added to ammonium chloride (164 mg, 3.07 mmol) in toluene (500 µL) while under argon with stirring for 10 minutes. This was then added to 4-(3-Bromo-benzenesulfoximine)-5-methylsulfanyl-thiophene-2-carboamide (Example 26: step a; 30 mg, 0.77 mmol) and then the reaction was heated to 80° C. for 2 hours. The reaction was then quenched by pouring into a slurry of silica in DCM and stirring for 10 minutes. The reaction was then filtered and washed with 30% MeOH in DCM. The filtrate was concentrated in vacuo and redissolved in 10% MeOH in DCM and then filtered again to remove silica. The filtrate was then purified by $C_{18}$-HPLC (5-60% $CH_3CN$/0.1% TFA water over 30 minutes) resulting in the isolation of the title compound (5.4 mg, 19%). $^1$H-NMR (CD$_3$OD): δ 8.29 (1H, s), 8.26-8.25 (1H, m), 8.10-8.08 (1H, m), 7.84-7.81 (1H, m), 7.50 (1H, t, J=7.9 Hz), 2.69 (3H, s).

EXAMPLE 27

4-(3-Bromo-benzenesulfoxamineacetamide)-5-methylsulfanyl-thiophene-2-carboxamidine

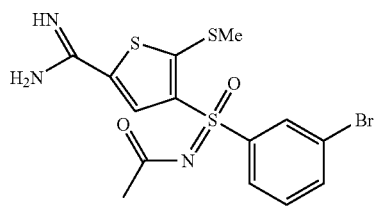

EXAMPLE 27a 4-(3-Bromo-benzenesulfoximine)-5-methylsulfanyl-thiophene-2-carbamic acid tert-butyl ester

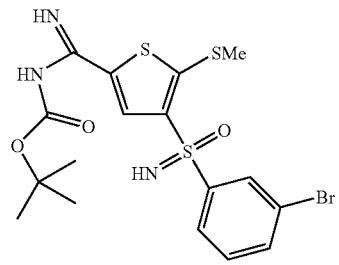

To a solution of 4-(3-Bromo-benzenesulfoximine)-5-methylsulfanyl-thiophene-2-carboxamidine (Example 26: step b; 17 mg, 0.31 mmol) was added DIEA (27 µL, 0.16 mmol) and Boc$_2$O (20 mg, 0.09 mmol) in DMF (500 µL). The reaction was stirred at RT for 12 hours. Solvent was removed in vacuo and triturated with hexane to remove Boc$_2$O resulting in the desired product (14 mg, 70%). $^1$H-NMR (CDCl$_3$): δ 8.24-8.23 (1H, m), 8.05-8.02 (1H, d, J=7.9 Hz), 7.87 (1H, s), 7.71-7.69 (1H, d, J=7.0 Hz), 7.41-7.36 (1H, t, J=7.8 Hz), 2.93 (3H, s), 1.52 (9H, s).

EXAMPLE 27b 4-(3-Bromo-benzenesulfoximineacetamide)-5-methylsulfanyl-thiophene-2-carboxamidine trifluoroacetate

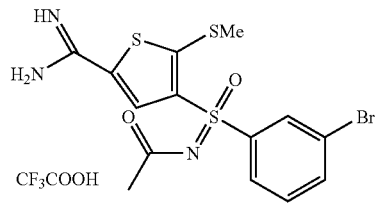

To a solution of 4-(3-Bromo-benzenesulfoximine)-5-methylsulfanyl-thiophene-2-carbamic acid tert-butyl ester (Example 27: step a; 1.3 mg, 0.0027 mmol) in AcOH (50 µL) was added acetic anhydride (0.4 µL, 0.0039 mmol) and the reaction was stirred at 45° C. for 2 hours. The reaction was purified by $C_{18}$-HPLC (5-80% $CH_3CN$/0.1% TFA water over 40 minutes) resulting in the isolation of the title compound (0.7 mg, 59%). $^1$H-NMR (CD$_3$OD): δ 8.36 (1H, s), 8.25-8.24 (1H, m), 8.09-8.06 (1H, d, J=8.0 Hz), 7.91-7.88 (1H, d, J=7.9 Hz), 7.58-7.54 (1H, t, J=7.9), 2.72 (3H, s), 2.23 (3H, s).

EXAMPLE 28

5-Bromo-4[S-(3-Bromophenyl)-N-Tosylsulfoximino]-thiophene-2-carboxamidine trifluoroacetate

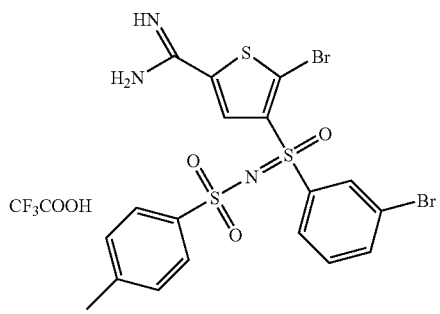

5-Bromo-4-[S-(3-Bromophenyl)-N-Tosylsulfoximino]-thiophene-2-carbonitrile (Example 25: step i; 10 mg, 0.018 mmol), and ammonium formate (excess) were stirred at RT in MeOH (400 μL). To this was added sodium methoxide (1 mg, 0.019 mmol) and the reaction was stirred at RT overnight. The reaction was purified by $C_{18}$-HPLC (5-80% $CH_3CN$/0.1% TFA water over 40 minutes) resulting in the isolation of the title compound (7.9 mg, 70%). $^1$H-NMR ($CD_3OD$): δ 8.36 (1H, s), 8.13 (1H, s), 8.06-8.04 (1H, d, J=9.70 Hz), 7.94-7.95 (1H, d, J=6.91 Hz), 7.74-7.72 (2H, d, J=8.28 Hz), 7.59 (1H, t, J=10.1 Hz), 7.34-7.32 (2H, d, J=8.86 Hz). ESI-MS (m/z): Calcd. For $C_{18}H_{15}Br_2N_3O_3S_3$: 574.86; found: 575.9.

EXAMPLE 29

4-[S-[3-(2-Tolylphenyl)phenyl]-N-Tosylsulfoximino]-5-methylsulfanyl-thiophene-2-carboxamidine trifluoroacetate

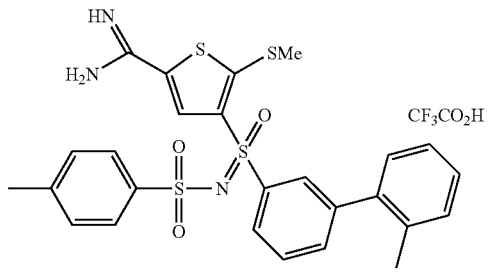

EXAMPLE 29a

4-[S-[3-(2-Tolylphenyl)phenyl]-N-Tosylsulfoximino]-5-methylsulfanyl-thiophene-2-carbonitrile

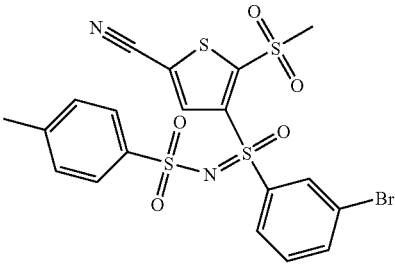

5-Bromo-4-[S-(3-Bromophenyl)-N-Tosylsulfoximino]-thiophene-2-carbonitrile (Example 25: step i; 188 mg, 0.36 mmol) was dissolved into DMF (3.5 mL) and cooled to −30° C. To this was added sodium methanesulfinate (36 mg, 0.36 mmol) as a solution in MeOH and the reaction was stirred at −30° C. for 2 hours. The reaction was then warmed to 0° C. for 4 hours and then warmed to RT overnight. TLC analysis indicated spots nearly identical, UV HPLC analysis showed shift in retention time. The crude reaction mixture was purified by flash column chromatography (20% EtOAc/Hexanes) resulting in the title compound as a clear glassy solid (124 mg, 66%). ESI-MS (m/z): Calcd. For $C_{19}H_{15}BrN_2O_5S_4$: 557.9; found: 558.7.

EXAMPLE 29b

4[S-(3-Bromophenyl)-N-Tosylsulfoximino]-5-methylsulfanyl-thiophene-2-formamide methyl ester

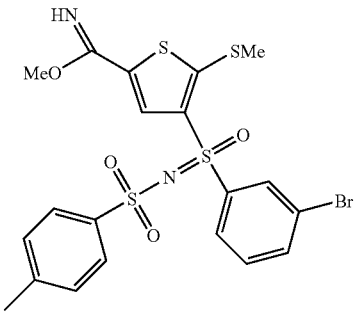

4-[S-[3-(2-Tolylphenyl)phenyl]-N-Tosylsulfoximino]-5-methylsulfanyl-thiophene—2-carbonitrile (Example 29: step a; 124 mg, 0.24 mmol) was dissolved in THF (5 mL). This was cooled to −78° C. followed by the slow addition of sodium thiomethoxide (0.5 M in MeOH, 720 μL, 0.36 mmol). The reaction was stirred at −78° C. for 2 hours and then warmed to RT overnight. The reaction was used without purification In the next step. ESI-MS (m/z): Calcd. For $C_{20}H_{19}BrN_2O_4S_4$: 557.94; found: 560.9.

EXAMPLE 29c 4-(S-(3-Bromophenyl)-N-Tosylsulfoximino)-5-methylsulfanyl-thiophene-2-carboxamidine trifluoroacetate

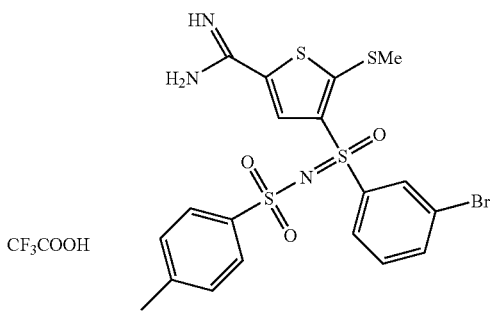

The crude reaction mixture of 5-Methylsulfonyl-4[S-(3-Bromophenyl)-N-Tosylsulfoximino]-thiophene-2-formamide methyl ester (Example 29: step b; 0.22 mmol) was concentrated to remove THF, dissolved in ammonia in methanol (2.0 M, 1.5 mL, 3 mmol). To this was added ammonium formate (14 mg, 0.22 mmol). The reaction was stirred at 30° C. for 2 days. ESI-MS (m/z): Calcd. For $C_{19}H_{18}BrN_3O_3S_4$: 542.94; found: 545.5.

EXAMPLE 29d 4-(S-(3-Bromophenyl)-N-Tosylsulfoximino)-5-methylsulfanyl-thiophene-2-carbamic acid-tert-butyl ester

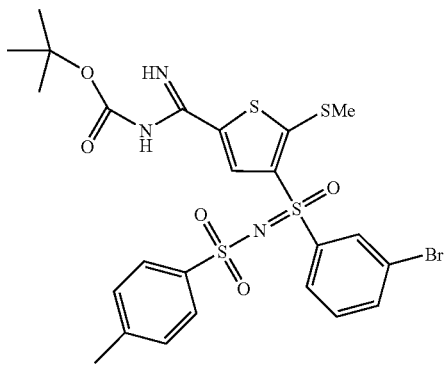

To a solution of 4-(S-(3-Bromophenyl)-N-Tosylsulfoximino)-5-methylsulfanyl-thiophene-2-carboxamidine trifluoroacetate (Example 29: step c; 124 mg, 0.23 mmol) in THF (5 mL) was added DIEA (0.72 µL, 0.046 mmol) and Boc$_2$O (60.2 mg, 0.27 mmol). The reaction was stirred at RT for 12 hours. The reaction was not complete therefore it was heated to 40° C. for 8 hours. The reaction was concentrated and purified by flash column chromatography (40% EtOAc/Hexanes) to isolate the title compound as a solid (86 mg, 59%). ESI-MS (m/z): Calcd. For $C_{24}H_{26}BrN_3O_5S_4$: 642.9; found: 645.6.

EXAMPLE 29e

4-[S-[3-(2-Tolylphenyl)phenyl]-N-Tosylsulfoximino]-5-methylsulfanyl-thiophene-2-carbamic acid tert-butyl ester

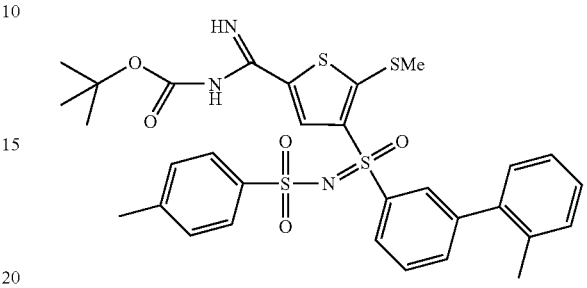

A solution of 4-(S-(3-Bromophenyl)-N-Tosylsulfoximino)-5-methylsulfanyl-thiophene-2-carbamic acid-tert-butyl ester (Example 29: step d; 35.5 mg, 0.055 mmol), o-tolyl boronic acid (15 mg, 0.110 mmol) and 2M Na$_2$CO$_3$ (220 µL, 0.44 mmol) was dissolved in Acetonitrile (1 mL). Argon gas was bubbled through the reaction mixture and then tetrakis(triphenylphosphine)palladium (0) (13 mg, 0.011 mmol) was added and the reaction was heated to 80° C. for 2 hours. The reaction mixture was dissolved in EtOAc and washed with brine. The organic layer was separated and dried with MgSO$_4$ and concentrated in vacuo. The reaction was purified by preparative thin layer chromatography (25% EtOAc/Hexane) resulting in the title compound (17 mg). ESI-MS (m/z): Calcd. For $C_{31}H_{33}N_3O_5S_4$: 655.1; found: 655.8.

EXAMPLE 29f

4-[S-[3-(2-Tolylphenyl)phenyl]-N-Tosylsulfoximino]-5-methylsulfanyl-thiophene-2-amidine trifluoroacetate

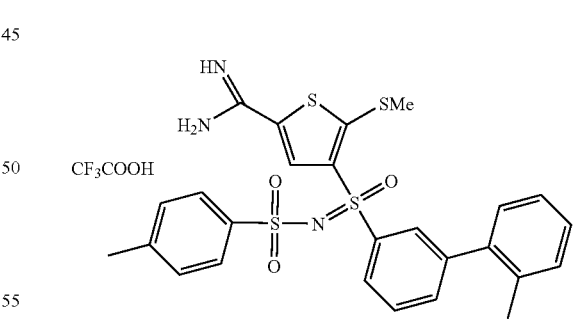

4-[S-[3-(2-Tolylphenyl)phenyl]-N-Tosylsulfoximino]-5-methylsulfanyl-thiophene-2-carbamic acid-tert-butyl ester (Example 29: step e; 17 mg, 0.03 mmol) was dissolved in 50% TFA/DCM (1 mL) and stirred for 1 hour. The reaction was concentrated in vacuo and purified by C$_{18}$-HPLC (10-80% CH$_3$CN/0.1% TFA water over 30 minutes) resulting in the isolation of the title compound (7.6 mg, 46%). $^1$H-NMR (CD$_3$OD): δ 8.28 (1H, s), 8.03-8.00 (1H, m), 7.94-7.93 (1H, m), 7.74-7.70 (4H, m), 7.32-7.26 (5H, m), 7.19-7.16 (1H, d, J=7.11 Hz), 2.67 (3H, s), 2.39 (3H, s), 2.20 (3H, s).

EXAMPLE 30

4-[S-(3-Bromophenyl)-N-Nosylsulfoximino]-5-methylsulfanyl-thiophene-2-amidine trifluoroacetate

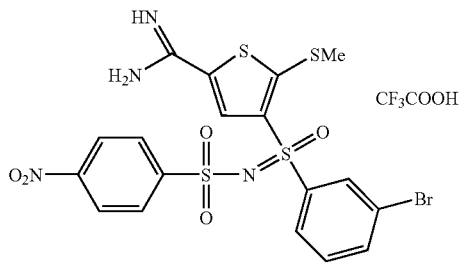

EXAMPLE 30a

4-[S-(3-Bromophenyl)-N-Nosylsulfoximino]-5-methanesulfonyl -thiophene-2-carbonitrile

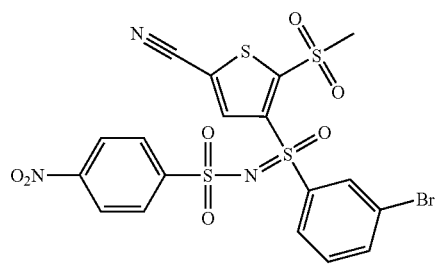

4-[S-(3-Bromophenyl)-N-Nosylsulfoximino]-5-chloro-thiophene-2-carbonitrile (Example 24: step g; 67.4 mg, 0.12 mmol) was dissolved in DMF (2 mL) and cooled to −30° C. To this was added 1M sodium methanesulfonyl in MeOH (140 μL, 0.14 mmol) and the reaction was stirred for one hour. The reaction was monitored by analytical $C_{18}$-HPLC (10-80% $CH_3CN$/0.1% TFA water over 8 minutes) which shows the conversion of starting material at rt=3.37 to product at rt=3.26. The reaction was concentrated, dissolved in EtOAc and washed with brine. The organic layer was dried with $MgSO_4$ and concentrated followed by preparative TLC purification (30% EtOAc/Hexanes). The title compound was isolated as a white solid (31 mg, 44%). $^1$H-NMR ($CD_3OD$): δ 8.38-8.36 (2H, d, J=9.0 Hz), 8.24 (1H, t, J=1.8 Hz), 8.18-8.16 (3H, m), 8.13-8.15 (1H, d, J=7.0 Hz), 7.87-7.84 (1H, d, J=7.5 Hz), 7.51 (1H, t, J=8.0 Hz), 3.70 (3H, s).

EXAMPLE 30b

4-[S-(3-Bromophenyl)-N-Nosylsulfoximino]-5-methylsulfanyl-thiophene-2-carboximidic acid methyl ester

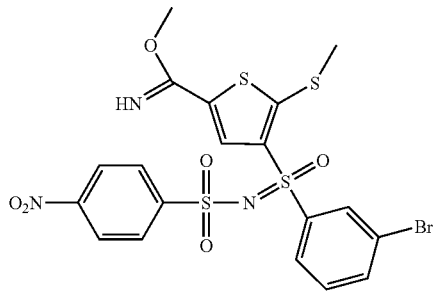

4-[S-(3-Bromophenyl)-N-Nosylsulfoximino]-5-methanesulfonyl -thiophene-2-carbonitrile (Example 30: step a; 31 mg, 0.049 mmol) was dissolved in THF (2 mL) and cooled to −78° C. To this was added 0.5 M sodium thiomethoxide in MeOH (120 μL, 0.059 mmol) slowly and stirred for 1 hour at −78° C. and then for 1 hour at RT. The reaction was quenched with MeOH and AcOH then dissolved into EtOAc and washed with sat. $NaHCO_3$. The organic layer was dried ($MgSO_4$) and then concentrated. The desired product was obtained without further purification as a yellow solid (30 mg, 90%). ESI-MS (m/z): Calcd. For $C_{19}H_{16}BrN_3O_6S_4$: 588.9; found: 591.8.

EXAMPLE 30c

4-[S-(3-Bromophenyl)-N-Nosylsulfoximino]-5-methylsulfanyl-thiophene-2-amidine trifluoroacetate

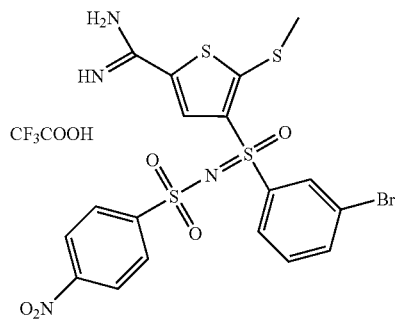

4-[S-(3-Bromophenyl)-N-Nosylsulfoximino]-5-methylsulfanyl-thiophene-2-carboximidic acid methyl ester (Example 30: step b; 28 mg, 0.047 mmol) was dissolved in MeOH (4 mL) and to this was added ammonium formate (29 mg, 0.47 mmol) and 2M ammonia in MeOH (2 mL). The reaction was stirred at RT for 24 hours followed by purification by $C_{18}$-HPLC (10-100% $CH_3CN$/0.1% TFA water over 30 minutes) resulting in the title compound as a white solid (2.3 mg, 10%). $^1$H-NMR ($CD_3OD$): δ 8.39-8.35 (3H, m), 8.13-8.10 (3H, m), 8.07-8.05 (1H, d, J=7.0 Hz), 7.96-7.93 (1H, d, J=8.0 Hz), 7.59 (1H, t, J=8.0 Hz), 2.73 (3H, s).

EXAMPLE 31

4-[S-(3-Bromophenyl)-N-sulfonyl-3-nitro-benzene sulfoximino]-5-methylsulfanyl-thiophene-2-amidine trifluoroacetate

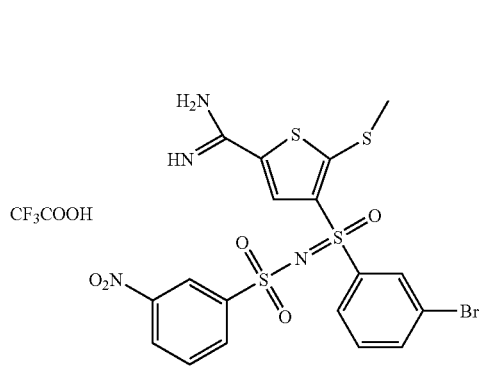

EXAMPLE 31a

4-[S-(3-Bromophenyl)-N-sulfonyl-3-nitro-benzene sulfoximino]-5-methylsulfanyl-thiophene-2-carbamic acid tert-butyl ester

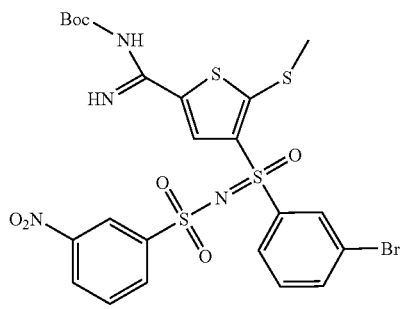

To a solution of 4-[S-(3-Bromophenyl)-sulfoximino]-5-methylsulfanyl-thiophene-2-carbamic acid tert-butyl ester (Example 24: step j; 94 mg, 0.139 mmol) in DCM (4 mL, and still slightly cloudy) was added triethylamine (39 µL, 0.28 mmol) and 3-nitrobenzene sulfonyl chloride (37 mg, 0.16 mmol). This reaction stirred at RT for several days. ESI-MS (m/z): Calcd. For $C_{23}H_{23}BrN_4O_7S_4$: 673.9; found: 676.5.

EXAMPLE 31b

4-[S-(3-Bromophenyl)-N-sulfonyl-3-nitro-benzene sulfoximino]-5-methylsulfanyl-thiophene-2-amidine trifluoroacetate

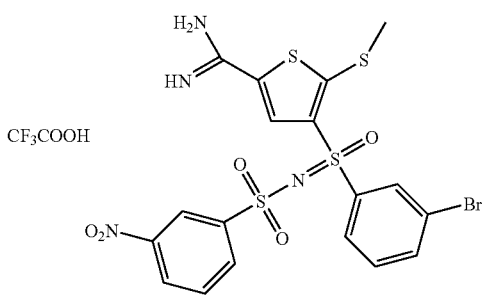

4-[S-(3-Bromophenyl)-N-sulfonyl-3-nitro-benzene sulfoximino]-5-methylsulfanyl-thiophene-2-carbamic acid tert-butyl ester (Example 31: step a; 10 mg, 0.01 mmol) was dissolved in 50% TFA/DCM (2 mL) and stirred at RT for 1 hour. The reaction was purified by $C_{18}$-HPLC (10-100% $CH_3CN$/0.1% TFA water over 30 minutes) resulting in the title compound as a white solid (6.2 mg, 73%). $^1$H-NMR ($CD_3OD$): δ 8.59-8.58 (1H, m), 8.49-8.47 (1H, d, J=7.25 Hz), 8.37 (1H, s), 8.30-8.27 (1H, d, J=6.9 Hz), 8.15-8.14 (1H, m), 8.07-8.05 (1H, d, J=9.0 Hz), 7.95-7.93 (1H, d, J=9.0 Hz), 7.83 (1H, t, J=8.0 Hz), 7.58 (1H, t, J=8.0 Hz), 2.71 (3H, s).

EXAMPLE 32

4-[S-(3-Bromophenyl)-N-sulfonyl-3-N-(5-Methanesulfonyl-4-methyl-thiazol-2-yl)-acetamide sulfoximino]-5-methylsulfanyl-thiophene-2-amidine trifluoroacetate

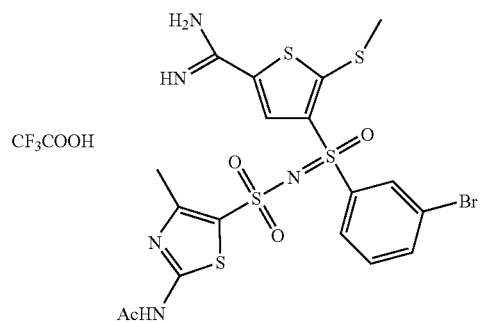

EXAMPLE 32a

4-[S-(3-Bromophenyl)-N-sulfonyl-3-N-(5-Methanesulfonyl-4-methyl-thiazol-2-yl)-acetamide sulfoximino]-5-methylsulfanyl-thiophene-2-carbamic acid tert-butyl ester

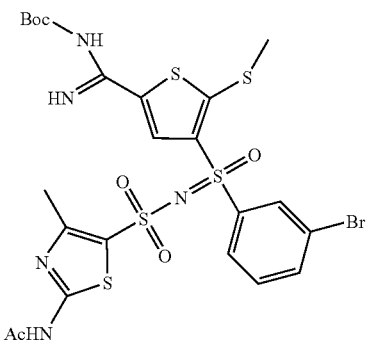

To a solution of 4-[S-(3-Bromophenyl)-sulfoximino]-5-methylsulfanyl-thiophene-2-carbamic acid tert-butyl ester (Example 24: step j; 13 mg, 0.019 mmol), in DCM (1 mL) was added Et$_3$N (5 µL, 0.038 mmol) and 2-Acetylamino-4-methyl-thiazole-5-sulfonyl chloride (5.9 mg, 0.024 mmol). The reaction was stirred at RT for 24 hours followed by purification by preparative TLC (40% EtOAc/Hexane) resulting in the title compound. ESI-MS (m/z): Calcd. For $C_{23}H_{26}BrN_5O_6S_5$: 706.9; found: 709.6.

EXAMPLE 32b

4-[S-(3-Bromophenyl)-N-sulfonyl-3-N-(5-Methanesulfonyl-4-methyl-thiazol-2-yl)-acetamide sulfoximino]-5-methylsulfanyl-thiophene-2-amidine trifluoroacetate

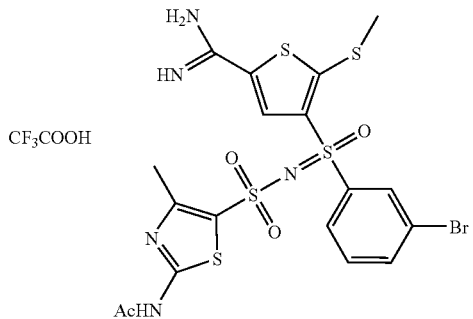

4-[S-(3-Bromophenyl)-N-sulfonyl-3-N-(5-Methanesulfonyl-4-methyl-thiazol-2-yl)-acetamide sulfoximino]-5-methylsulfanyl-thiophene-2-carbamic acid tert-butyl ester (Example 32, step a) was treated with 50% TFA/DCM (2 mL) and stirred for 1 hour. The reaction was concentrated and purified by C$_{18}$-HPLC (10-100% CH$_3$CN/0.1% TFA water over 30 minutes) resulting in the title compound as a clear glass (2.4 mg). $^1$H-NMR (CD$_3$OD): δ 8.37 (1H, s), 8.14 (1H, t, J=1.8 Hz), 8.05 (1H, d, J=9.0 Hz), 7.94 (1H, d, J=9.8 Hz), 7.58 (1H, t, J=8.0 Hz), 2.70 (3H, s), 2.50 (3H, s), 2.24 (3H, s).

EXAMPLE 33

4-[S-(3-Bromophenyl)-N-sulfonyl-4-aminophenyl-sulfoximino]-5-methylsulfanyl-thiophene-2-amidine trifluoroacetate

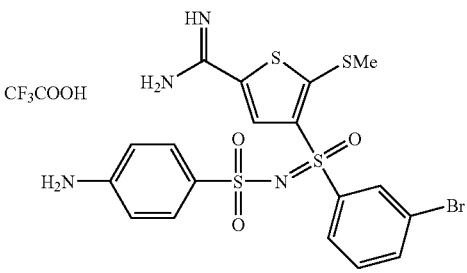

EXAMPLE 33a

4-[S-(3-Bromophenyl)-N-sulfonyl-4-nitro-benzene sulfoximino]-5-methylsulfanyl-thiophene-2-carbamic acid tert-butyl ester

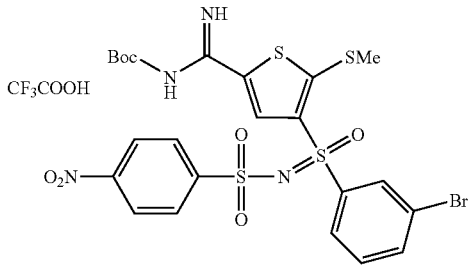

To a solution of 4-[S-(3-Bromophenyl)-N-Nosylsulfoximino]-5-methylsulfanyl-thiophene-2-amidine trifluoroacetate (Example 30: step c; 70 mg, 0.12 mmol) in THF (5 mL) and DIEA (42 µL, 0.24 mmol) was added Boc$_2$O (53 mg, 0.24 mmol) and the reaction was stirred at RT for 12 hours. The reaction was concentrated, dissolved in EtOAc and washed with saturated NaHCO$_3$. The organic layer was dried (MgSO$_4$) and concentrated resulting in desired product. $^1$H-NMR (CD$_3$OD): δ 8.30 (2H, d, J=8.8 Hz), 8.18 (2H, d, J=8.8 Hz), 8.01 (1H, s), 7.99 (1H, 8.0 Hz), 7.79 (1H, d, J=7.2 Hz), 7.44 (1H, t, J=8.0 Hz), 2.59 (3H, s), 1.53-1.46 (9H, m).

EXAMPLE 33b

4-[S-(3-Bromophenyl)-N-sulfonyl-4-amino-benzene sulfoximino]-5-methylsulfanyl-thiophene-2-carbamic acid tert-butyl ester

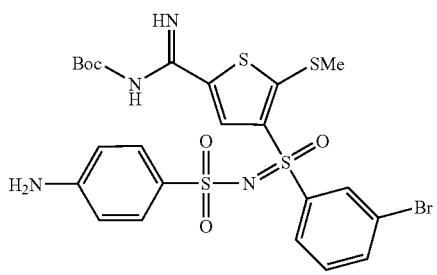

To a solution of 4-[S-(3-Bromophenyl)-N-sulfonyl-4-nitro-benzene sulfoximino]-5-methylsulfanyl-thiophene-2-carbamic acid tert-butyl ester (Example 33: step a; 15 mg, 0.02 mmol) in MeOH (1 mL) and H$_2$O (1 mL) was added NH$_4$Cl (11.6 mg, 0.22 mmol) and Fe (12.2 mg, 0.22 mmol). The reaction was heated to 80° C. for 1 hour and was then filtered through a pad of celite and washed with DCM and EtOAc. The combined filtrates were concentrated. ESI-MS (m/z): Calcd. For C$_{23}$H$_{25}$BrN$_4$O$_5$S$_4$: 643.9; found: 646.5.

EXAMPLE 33c

4-[S-(3-Bromophenyl)-N-sulfonyl-4-aminophenyl-sulfoximino]-5-methylsulfanyl-thiophene-2-amidine trifluoroacetate

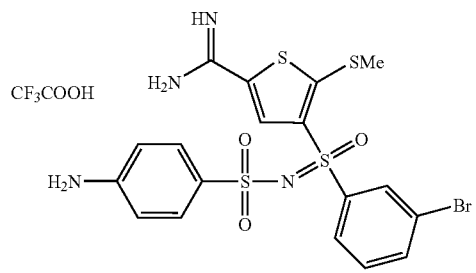

4-[S-(3-Bromophenyl)-N-sulfonyl-4-amino-benzene sulfoximino]-5-methylsulfanyl-thiophene-2-carbamic acid tert-butyl ester (Example 33: step b) was dissolved in DCM (1 mL) and TFA (1 mL) and stirred at RT for 1 hour. The reaction was concentrated and purified by C$_{18}$-HPLC (10-100% CH$_3$CN/0.1% TFA water over 30 minutes) resulting in the title compound as a yellow solid (5.9 mg). $^1$H-NMR (CD$_3$OD): δ 8.23 (1H, s), 8.08 (1H, s), 7.98 (1H, d, J=7.1 Hz), 7.89 (1H, d, J=9.8 Hz), 7.52 (1H, t, J=8.0 Hz), 7.47-7.44 (2H, m), 6.58-6.56 (2H, m), 2.67 (3H, s).

EXAMPLE 34

4-[S-(3-Bromophenyl)-N-sulfonyl-3-analine sulfoximino]-5-methylsulfanyl-thiophene-2-amidine trifluoroacetate

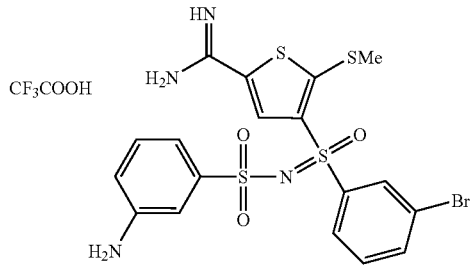

EXAMPLE 34a

4-[S-(3-Bromophenyl)-N-sulfonyl-3-nitro-benzene sulfoximino]-5-methylsulfanyl-thiophene-2-carbamic acid tert-butyl ester

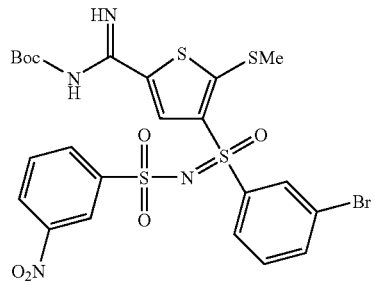

To a solution of 4-[S-(3-Bromophenyl)-sulfoximino]-5-methylsulfanyl-thiophene-2-carbamic acid tert-butyl ester (Example 24: step j; 58 mg, 0.11 mmol) in THF (5 mL) and TEA (35 µL, 0.24 mmol) was added 3-nitrobenzene sulfonylchloride (53 mg, 0.24 mmol) and the reaction was stirred at RT for 5 hours. The reaction was concentrated, and purified by preparative TLC (30% EtOAc/Hexane). ESI-MS (m/z): Calcd. For C$_{23}$H$_{23}$BrN$_4$O$_7$S$_4$: 673.9; found: 674.5.

EXAMPLE 34b

4-[S-(3-Bromophenyl)-N-sulfonyl-3-analine sulfoximino]-5-methylsulfanyl-thiophene-2-carbamic acid tert-butyl ester

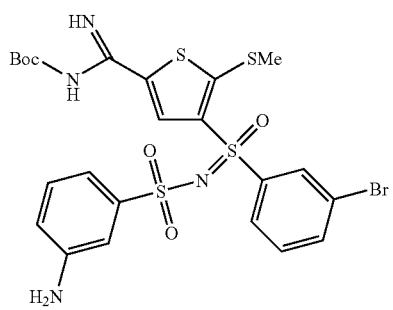

To a solution of 4-[S-(3-Bromophenyl)-N-sulfonyl-3-nitro-benzene sulfoximino]-5-methylsulfanyl-thiophene-2-carbamic acid tert-butyl ester (Example 34: step a; 20 mg, 0.03 mmol) in MeOH (1 mL) was and H₂O (1 mL) was added NH₄Cl (15.5 mg, 0.29 mmol) and Fe (16.6 mg, 0.29 mmol). The reaction was heated to 80° C. for 1 hour and was then filtered through a pad of celite and washed with DCM and EtOAc. The combined filtrates were concentrated. ESI-MS (m/z): Calcd. For $C_{23}H_{25}BrN_4O_5S_4$: 643.9; found: 646.6.

EXAMPLE 34c

4-[S-(3-Bromophenyl)-N-sulfonyl-3-analine sulfoximino]-5-methylsulfanyl-thiophene-2-amidine trifluoroacetate

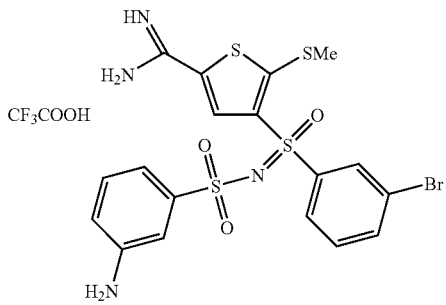

4-[S-(3-Bromophenyl)-N-sulfonyl-4-amino-benzene sulfoximino]-5-methylsulfanyl-thiophene-2-carbamic acid tert-butyl ester (Example 34: step b) was dissolved in DCM (1 mL) and TFA (1 mL) and stirred at RT for 1 hour. The reaction was concentrated and purified by $C_{18}$-HPLC (10-80% CH₃CN/0.1% TFA water over 30 minutes) resulting in the title compound as a clear glass (1.1 mg). ¹H-NMR (CD₃OD): δ 8.28 (1H, s), 8.15 (1H, s), 8.03 (1H, d, J=7.0 Hz), 7.93 (1H, d, J=9.9 Hz), 7.56 (1H, t, J=10.2 Hz), 7.25-7.15 (3H, m), 6.93 (1H, d, J=7.8 Hz), 2.70 (3H, s).

EXAMPLE 35

4-[S-(3-Bromophenyl)-N-(6-cyano-3-pyridinecarboxamido)-sulfoxamino]-5-methylsulfanyl-thiophene-2-carboxamidine trifluoroacetate

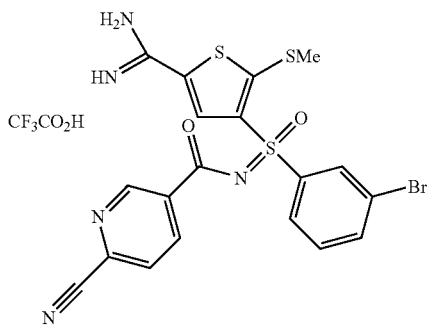

EXAMPLE 35a

4-[S-(3-Bromophenyl)-N-(6-cyano-3-pyridinecarboxamido)-sulfoxamino]-5-methylsulfanyl-thiophene-2-carbamic acid tert-butyl ester

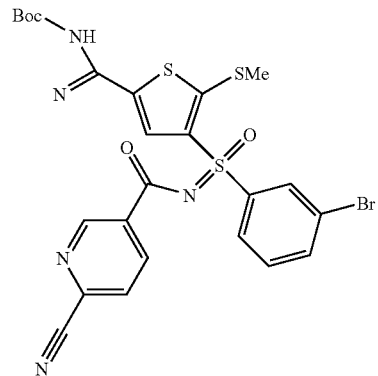

6-Cyano nicotinic acid (18 mg, 0.118 mmol), DIC (18.5 μL, 0.118 mmol), and DMAP (29 mg, 0.236 mmol) were dissolved in DCM (1 ml). The mixture was stirred for 10 min and then transferred to a solution of 4-[S-(3-bromophenyl)-sulfoxamino]-5-methylsulfanyl-thiophene-2-carbamic acid tert-butyl ester (29 mg, 0.059 mmol, as prepared in Example 24: step j) in THF. After 12 h at RT, another portion of 6-cyano nicotinic acid (37 mg, 0.236 mmol) was activated with DIC (37 μL, 0.236 mmol) and DMAP (58 mg, 0.472 mmol) in DCM (2 mL) for 10 min and then transferred to the reaction mixture. The final mixture was stirred for another 48 h at RT. The reaction mixture was evaporated in vacuo and the residue was purified using preparative TLC (2×1000μ, 1:1 EtOAc/Hexanes) to provide 10 mg 4-[S-(3-bromophenyl)-N-(6-cyano-3-pyridinecarboxamido)-sulfoxamino]-5-methylsulfanyl-thiophene-2-carbamic acid tert-butyl ester.

EXAMPLE 35b

4-[S-(3-Bromophenyl)-N-(6-cyano-3-pyridinecarboxamido)-sulfoxamino]-5-methylsulfanyl-thiophene-2-carboxamidine trifluoroacetate

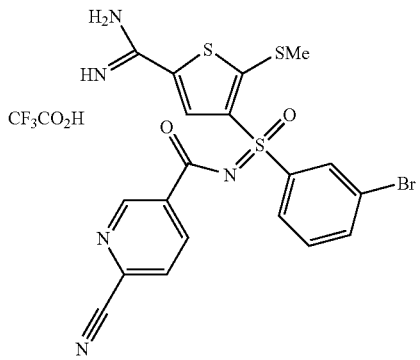

4-[S-(3-bromophenyl)-N-(6-cyano-3-pyridinecarboxamido)-sulfoxamino]-5-methylsulfanyl-thiophene-2-carbamic acid tert-butyl ester (4 mg, 0.0065 mmol, as prepared in Example 35: step a) was treated with TFA (50% in DCM) for 1 h at RT. The reaction mixture was evaporated in vacuo and the residue was purified using RP-HPLC to give 2.0 mg of the title compound 4-[S-(3-bromophenyl)-N-(6-cyano-3-pyridinecarboxamido)-sulfoxamino]-5-methylsulfanyl-thiophene-2-carboxamidine trifluoroacetate as a white solid. $^1$H-NMR (CD$_3$OD): δ 9.45-9.46 (m, 1H), 8.69 (dd, 1H, J=2.1, 8.1 Hz), 8.52 (s, 1H), 8.35-8.37 (m, 1H), 8.23 (dm, 1H, J=8.1 Hz), 8.04 (dd, 1H, J=0.8, 8.1 Hz), 7.98 (dm, 1H, J=8.0 Hz), 7.64 (t, 1H, J=8.0 Hz), and 2.73 (s, 3H). ESI-MS (m/z): Calcd. for C$_{19}$H$_{14}$BrN$_5$O$_2$S$_3$: 520 (M+1); found: 519.9.

EXAMPLE 36

4-[S-(3-Bromophenyl)-N-(acyl-3-pyridine-4-carboxamide)-sulfoxamino]-5-methylsulfanyl-thiophene-2-carboxamidine trifluoroacetate

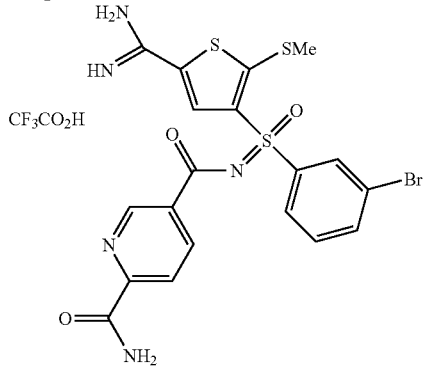

To 4-[S-(3-bromophenyl)-N-(6-cyano-3-pyridinecarboxamido)-sulfoxamino]-5-methylsulfanyl-thiophene-2-carbamic acid tert-butyl ester (4 mg, 0.0065 mmol, as prepared in Example 35: step a) in an ice bath was added concentrated H$_2$SO$_4$ (1 mL). The reaction was slowly warmed up to 60° C. for 1 hr. The mixture was diluted with MeOH (2 mL) and H$_2$O (7 mL) and purified using RP-HPLC to provide 1.8 mg of the titled compound 4-[S-(3-bromophenyl)-N-(acyl-3-pyridine-4-carboxamide)-sulfoxamino]-5-methylsulfanyl-thiophene-2-carboxamidine trifluoroacetate. $^1$H-NMR (CD$_3$OD): δ 9.36-9.40 (m, 1H), 8.67-8.72 (m, 1H), 8.51 (s, 1H), 8.36-8.38 (m, 1H), 8.22-8.28 (m, 2H), 7.96-8.00 (m, 1H), 7.61-7.67 (m, 1H), and 2.72 (s, 3H). ESI-MS (m/z): Calcd. for C$_{19}$H$_{16}$BrN$_5$O$_3$S$_3$: 538 (M+1); found: 537.9.

EXAMPLE 37

4-[S-(3-Bromophenyl)-N-(sulfonyl-3-phenylcarbonitrile)-sulfoxamino]-5-methylsulfanyl-thiophene-2-carboxamidine trifluoroacetate

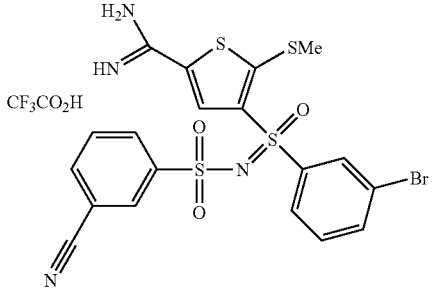

4-[S-(3-Bromophenyl)-sulfoxamino]-5-methylsulfanyl-thiophene-2-carbamic acid tert-butyl ester (10 mg, 0.02 mmol, as prepared in Example 24: step j) was dissolved in THF in a microwave tube and to it was added 2,6-lutidine (5 μL, 0.044 mmol) and 3-cyano-benzenesulfonyl chloride (5.6 mg, 0.028 mmol). The tube was sealed and heated in a microwave oven at 110° C. for 20 min. The reaction mixture was allowed to cool, concentrated in vacuo, and then chromatographed using preparative TLC (1000 μm, 1:1 EtOAc/hexanes) to give an oily residue. A portion of this material was immediately treated with 50% TFA in DCM for 1 h at RT and the resulting mixture was purified on RP-HPLC to provide 1 mg of the titled compound 4-[S-(3-bromophenyl)-N-(sulfonyl-3-phenylcarbonitrile)-sulfoxamino]-5-methylsulfanyl-thiophene-2-carboxamidine trifluoroacetate. $^1$H-NMR (CD$_3$OD): δ 8.38 (s, 1H), 8.14-8.19 (m, 3H), 7.94-8.04 (m, 3H), 7.57-7.77 (m, 2H), and 2.72 (s, 3H). ESI-MS (m/z): Calcd. for C$_{19}$H$_{15}$BrN$_4$O$_3$S$_4$: 554.9 (M+1); found: 554.8.

EXAMPLE 38

4-[S-(3-Bromophenyl)-N-(sulfonyl-3-benzamide)-sulfoxamino]-5-methylsulfanyl-thiophene-2-carboxamidine trifluoroacetate

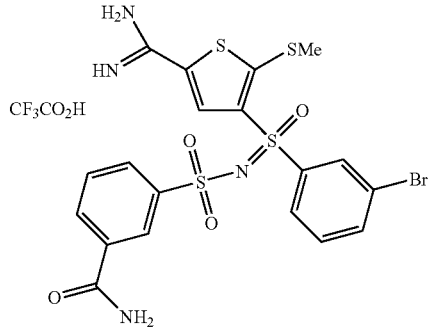

EXAMPLE 38a 3-(1-Methyl-1-phenyl-ethylcarbamoyl)-benzenesulfonyl chloride

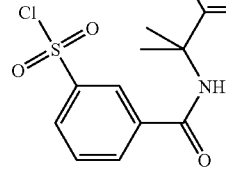

3-Chlorosulfonyl-benzoyl chloride (1 g, 4.2 mmol) was dissolved in DCM (10 mL) and cooled in an ice bath. To the solution was added 1-methyl-1-phenyl-ethylamine (0.9 g, 3.8 mmol) and 2,6-lutidine (1 mL, 8.4 mmol). The mixture was allowed to warm up to RT and stirred for 4 h. The reaction mixture was diluted with EtOAc (100 mL) and washed with 1 N HCl (2×75 mL) and brine. The organic layer was dried (MgSO$_4$) and evaporated in vacuo to provide 1.37 g (98%) of 3-(1-methyl-1-phenyl-ethylcarbamoyl)-benzenesulfonyl chloride as a tan solid. $^1$H-NMR (CDCl$_3$): δ 8.40 (t, 1H, J=1.7 Hz), 8.15-8.18 (m, 2H), 7.72 (t, 1H, J=7.8 Hz), 7.46-7.50 (m, 2H), 7.36-7.41 (m, 2H), 7.27-7.32 (m, 1H), 6.56 (br s, 1H), and 1.87 (s, 6H).

EXAMPLE 38b

4-[S-(3-Bromophenyl)-N-(sulfonyl-3-benzamide)-sulfoxamino]-5-methylsulfanyl-thiophene-2-carboxamidine trifluoroacetate

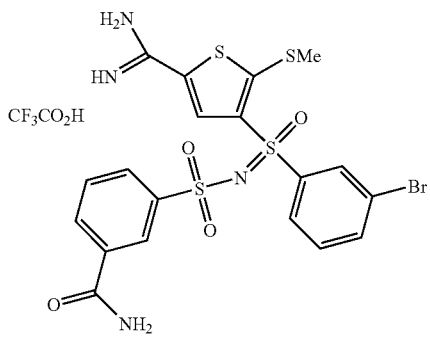

4-[S-(3-Bromophenyl)-sulfoxamino]-5-methylsulfanyl-thiophene-2-carbamic acid tert-butyl ester (33 mg, 0.067 mmol, as prepared in Example 24: step j), 3-(1-methyl-1-phenyl-ethylcarbamoyl)-benzenesulfonyl chloride (68 mg, 0.20 mmol, as prepared in Example 38: step a), and 2,6-lutidine (25 μL, 0.21 mmol) were dissolved in THF (4 mL) and then warmed up to 50° C. After 48 h, the reaction mixture was diluted with EtOAc (50 mL) and then washed with saturated NaHCO₃. The organic layer was dried (MgSO₄) and then evaporated in vacuo to give a residue that was treated with 50% TFA in DCM for 2 h at RT. The volatiles were removed in vacuo and the crude product was purified using RP-HPLC (CH₃CN/H₂O gradient) to provide 2.0 mg of the title compound 4-[S-(3-bromophenyl)-N-(sulfonyl-3-benzamide)-sulfoxamino]-5-methylsulfanyl-thiophene-2-carboxamidine trifluoroacetate. $^1$H-NMR (CD₃OD): δ 8.81 (m, 1H), 8.55 (s, 1H), 8.28 (t, 1H, J=1.7 Hz), 8.13-8.18 (m, 2H), 8.04-8.06 (m, 1H), 7.90-7.92 (m, 1H), 7.54-7.60 (m, 2H), and 2.70 (s, 3H). ESI-MS (m/z): Calcd. for $C_{19}H_{17}BrN_4O_4S_4$: 573.9 (M+1); found: 573.9.

EXAMPLE 39

4-[S-(3-Bromophenyl)-N-(sulfonyl-3-trifluoromethylbenzene)-sulfoxamino]-5-methylsulfanyl-thiophene-2-carboxamidine trifluoroacetate

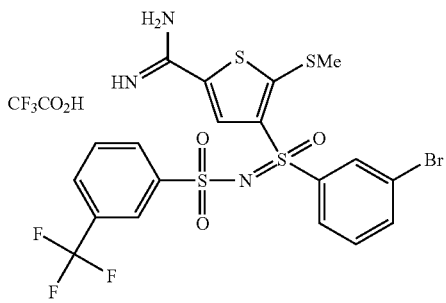

The title compound was prepared following the same procedure described for Example 38: step b. Reaction of 4-[S-(3-bromophenyl)-sulfoxamino]-5-methylsulfanyl-thiophene-2-carbamic acid tert-butyl ester (10 mg, 0.02 mmol, as prepared in Example 24: step j), 3-trifluoromethyl-benzenesulfonyl chloride (10 mg, 0.04 mmol), and 2,6-lutidine (25 μL, 0.21 mmol) in THF (2 mL), followed by analogous work up and purification as described in Example 38: step b, provided 4.5 mg of the title compound 4-[S-(3-bromophenyl)-N-(sulfonyl-3-trifluoromethylbenzene)-sulfoxamino]-5-methylsulfanyl-thiophene-2-carboxamidine trifluoroacetate. $^1$H-NMR (CD₃OD): δ 8.37 (s, 1H), 8.15-8.19 (m, 2H), 8.09-8.11 (m, 1H), 8.04-8.07 (m, 1H), 7.93-7.97 (m, 2H), 7.56-7.80 (m, 2H), and 2.72 (s, 3H). ESI-MS (m/z): Calcd. for $C_{19}H_{15}BrFN_3O_3S_4$: 597.9 (M+1); found: 597.8.

EXAMPLE 40

4-[S-(3-Bromophenyl)-N-(sulfonyl-2-methyl-5-nitro-benzene)-sulfoxamino]-5-methylsulfanyl-thiophene-2-carboxamidine trifluoroacetate

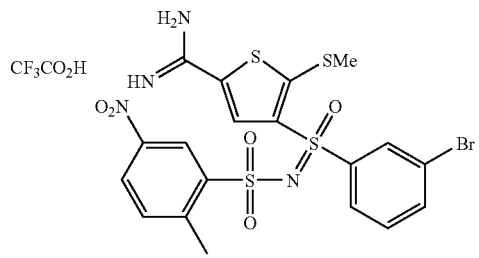

The title compound was prepared following the same procedure described for Example 38: step b. Reaction of 4-[S-(3-bromophenyl)-sulfoxamino]-5-methylsulfanyl-thiophene-2-carbamic acid tert-butyl ester (10 mg, 0.02 mmol, as prepared in Example 24: step j), 4-methyl-3-nitro-benzenesulfonyl chloride (10 mg, 0.04 mmol), and 2,6-lutidine (25 μL, 0.21 mmol) in THF (2 mL), followed by analogous work up and purification as described in Example 38: step b, provided 2.0 mg of the title compound 4-[S-(3-Bromophenyl)-N-(sulfonyl-2-methyl-5-nitro-benzene)-sulfoxamino]-5-methylsulfanyl-thiophene-2-carboxamidine trifluoroacetate. $^1$H-NMR (CD₃OD): δ 8.34-8.46 (m, 3H), 8.11-8.14 (m, 1H), 8.05 (dm, 1H, J=8.1 Hz), 7.95 (dm, 1H, J=8.0 Hz), 7.65-7.68 (m, 1H), 7.59 (t, 1H, J=8.1 Hz), 2.89 (s, 3H), and 2.65 (s, 3H). ESI-MS (m/z): Calcd. for $C_{19}H_{17}BrN_4O_5S_4$: 588.9 (M+1); found: 588.9.

EXAMPLE 41

4-[S-(3-Bromophenyl)-N-(sulfonyl-5-methanesulfonyl-2-methyl-benzene)-sulfoxamino]-5-methylsulfanyl-thiophene-2-carboxamidine trifluoroacetate

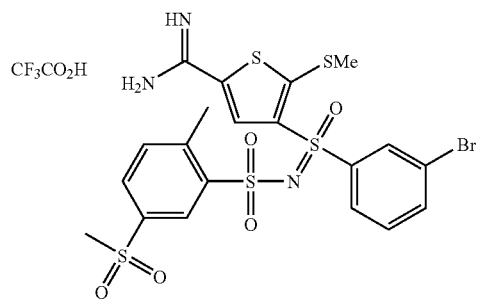

The title compound was prepared following the same procedure described for Example 38: step b. Reaction of 4-[S-(3-bromophenyl)-sulfoxamino]-5-methylsulfanyl-thiophene-2-carbamic acid tert-butyl ester (10 mg, 0.02 mmol, as prepared in Example 24: step j), 5-methanesulfonyl-2-methyl-benzenesulfonyl chloride (11 mg, 0.04 mmol), and 2,6-lutidine (25 µL, 0.21 mmol) in THF (2 mL), followed by analogous work up and purification as described in Example 38: step b, provided 1.0 mg of the title compound. $^1$H-NMR (CD$_3$OD): δ 8.35 (s, 1H), 8.15-8.17 (m, 1H), 8.03-8.08 (m, 2H), 7.95-7.98 (m, 1H), 7.73 (d, 1H, J=8.1 Hz), 7.68 (d, 1H, J=7.9 Hz), 7.60 (t, 1H, J=8.1 Hz), 3.14 (s, 3H), 2.88 (s, 3H), and 2.65 (s, 3H). ESI-MS (m/z): Calcd. for C$_{20}$H$_{20}$BrN$_3$O$_5$S$_5$: 621.9 (M+1); found: 621.9.

EXAMPLE 42

4-[S-(3-Bromophenyl)-N-(sulfonyl-5-bromo-4-chloro 3-pyridine)-sulfoxamino]-5-methylsulfanyl-thiophene-2-carboxamidine bistrifluoroacetate

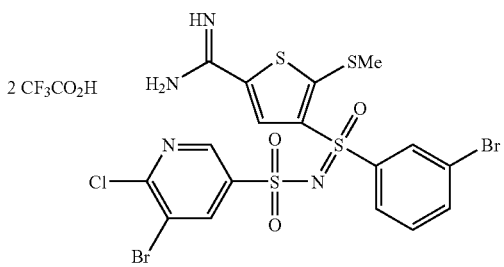

The title compound was prepared following the same procedure described for Example 38: step b. Reaction of 4-[S-(3-bromophenyl)-sulfoxamino]-5-methylsulfanyl-thiophene-2-carbamic acid tert-butyl ester (10 mg, 0.02 mmol, as prepared in Example 24: step j), 5-bromo-6-chloro-pyridine-3-sulfonyl chloride (12 mg, 0.04 mmol), and 2,6-lutidine (25 µL, 0.21 mmol) in THF (2 mL), followed by analogous work up and purification as described in Example 38: step b, provided 2.0 mg of the title compound 4-[S-(3-bromophenyl)-N-(sulfonyl-5-bromo-4-chloro 3-pyridine)-sulfoxamino]-5-methylsulfanyl-thiophene-2-carboxamidine bistrifluoroacetate. $^1$H-NMR (CD$_3$OD): δ 8.77 (d, 1H, J=2.2 Hz), 8.49 (d, 1H, J=2.2 Hz), 8.39 (s, 1H), 8.16-8.17 (m, 1H), 8.07 (dm, 1H, J=8.1 Hz), 7.98 (dm, 1H, J=8.1 Hz), 7.62 (t, 1H, J=8.1 Hz), and 2.74 (s, 3H). ESI-MS (m/z): Calcd. for C$_{17}$H$_{13}$Br$_2$ClN$_4$O$_3$S$_4$: 642.8 (M+1); found: 642.8.

EXAMPLE 43

4-[S-(3-Bromophenyl)-N-[sulfonyl-7-(4-methyl-3,4-dihydro-2H-benzo[1,4]oxazine)]-sulfoxamino]-5-methylsulfanyl-thiophene-2-carboxamidine bistrifluoroacetate

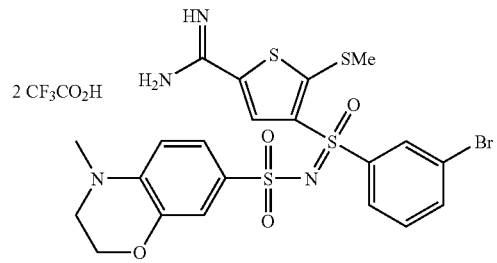

The title compound was prepared following the same procedure described for Example 38: step b. Reaction of 4-[S-(3-bromophenyl)-sulfoxamino]-5-methylsulfanyl-thiophene-2-carbamic acid tert-butyl ester (10 mg, 0.02 mmol, as prepared in Example 24: step j), 4-methyl-3,4-dihydro-2H-benzo[1,4]oxazine-7-sulfonyl chloride (10 mg, 0.04 mmol), and 2,6-lutidine (25 µL, 0.21 mmol) in THF (2 mL), followed by analogous work up and purification as described in Example 38: step b, provided 2.6 mg of the title compound 4-[S-(3-bromophenyl)-N-[sulfonyl-7-(4-methyl-3,4-dihydro-2H-benzo[1,4]oxazine)]-sulfoxamino]-5-methylsulfanyl-thiophene-2-carboxamidine bistrifluoroacetate. $^1$H-NMR (CD$_3$OD): δ 8.25 (s, 1H), 8.07 (t, 1H, J=1.7 Hz), 7.96-7.80 (m, 1H), 7.89-7.92 (m, 1H), 7.54, (t, 1H, J=8.0 Hz), 7.08 (dd, 1H, J=8.4, 2.1 Hz), 7.00 (d, 1H, J=2.3 Hz), 6.72 (d, 1H, J=8.4 Hz), 4.30-4.35 (m, 2H), 3.48-3.72 (m, 2H), 2.90 (s, 3H), and 2.71 (s, 3H). ESI-MS (m/z): Calcd. for C$_{21}$H$_{21}$BrN$_4$O$_4$S$_4$: 600.9 (M+1); found: 600.9.

EXAMPLE 44

4-[S-(3-Bromophenyl)-N-(sulfonyl-3-guanidinobenzene)-sulfoxamino]-5-methylsulfanyl-thiophene-2-carboxamidine bistrifluoroacetate

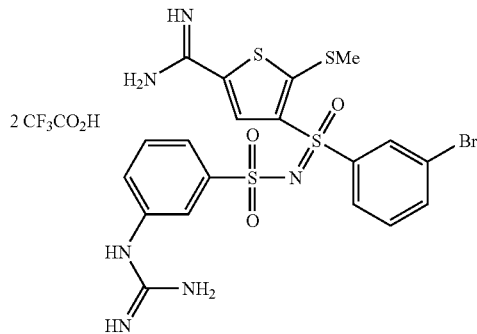

4-[S-(3-Bromophenyl)-N-(6-cyano-3-pyridinecarboxamido)-sulfoxamino]-5-methylsulfanyl-thiophene-2-carbamic acid tert-butyl ester (10 mg, 0.016 mmol, prepared in Example 34: step b) and N,N'-di-Boc-S-methylisothiourea (15 mg, 0.05 mmol) were dissolved in AcOH/MeOH (1:15, 3 ml). The solution was heated at 50° C. for 24 h and then concentrated in vacuo. The residue was dissolved in EtOAc and washed with water and brine. The EtOAc layer was removed in vacuo and the residue was redissolved in TFA/DCM (1:1, 4 mL). After 1 h at RT, the solvents were evaporated and the crude product was purified using RP-HPLC as described in Example 38: step b to provide 2.0 mg of the title compound 4-[S-(3-bromophenyl)-N-(sulfonyl-3-guanidinobenzene)-sulfoxamino]-5-methylsulfanyl-thiophene-2-carboxamidine bistrifluoroacetate. $^1$H-NMR (CD$_3$OD): δ 8.41 (s, 1H), 8.21 (t, 1H, J=1.7 Hz), 8.08 (ddd, 1H, J=7.9, 1.9, 0.9 Hz), 7.96 (ddd, 1H, J=7.9, 1.9, 0.9 Hz), 7.89 (ddd, 1H, 7.9, 1.9, 1.0 Hz), 7.80-7.82 (m, 1H), 7.67 (t, 1H, 7.9 Hz), 7.54-7.62 (m, 2H), and 2.76 (s, 3H). ESI-MS (m/z): Calcd. for C$_{19}$H$_1$BrN$_6$O$_3$S$_4$: 586.9 (M+1); found: 586.8.

EXAMPLE 45

4-[S-(3-Bromophenyl)-N-(sulfonyl-3-methanesulfonyl benzene)-sulfoxamino]-5-methylsulfanyl-thiophene-2-carboxamidine trifluoroacetate

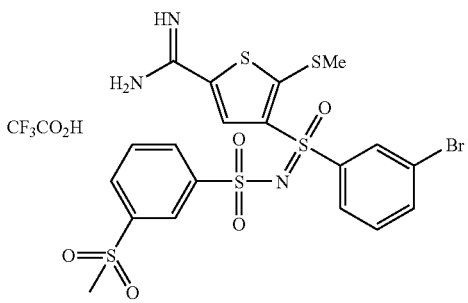

EXAMPLE 45a

3-Methanesulfonyl-benzenesulfonyl chloride

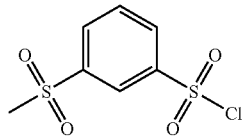

3-Methanesulfonyl-benzenesulfonyl chloride was prepared according to a previously described procedure (Tetrahedron 59 (2003) 1317-1325). 3-Methanesulfonyl-phenylamine (1 gm, 4.8 mmol) was dissolved in CH$_3$CN (40 mL). The solution was cooled in an ice bath (0-5° C.) and 4 mL of acetic acid and 2 mL of concentrated HCl were added. To the mixture was added NaNO$_2$ (397 mg, 5.76 mmol, in 3 mL water) over 10 min at 5° C. After stirring 20 min, SO$_2$ gas was bubbled in over 30 min (~200 drops) keeping the reaction mixture <7° C. A solution of CuCl$_2$ (840 mg, 6.24 mmol) in water (2.5 mL) was added and the mixture was allowed to warm and stir for 16 h at RT. The mixture was concentrated in vacuo and the remaining mixture was diluted with 1 N HCl and extracted with EtOAc (3×100 mL). The combined organic layer was washed with brine, dried (MgSO$_4$), and evaporated in vacuo to provide 1.2 gm of 3-methanesulfonyl-benzenesulfonyl chloride as a pale yellow solid. $^1$H-NMR (CDCl$_3$): δ 8.62 (t, 1H, J=1.6 Hz), 8.33-8.36 (m, 2H), 7.92t, 1H, J=8.0 Hz), 7.28 (s, 1H), and 3.18 (s, 3H).

EXAMPLE 45b

4-[S-(3-Bromophenyl)-N-(sulfonyl-3-methanesulfonyl benzene)-sulfoxamino]-5-methylsulfanyl-thiophene-2-carboxamidine trifluoroacetate

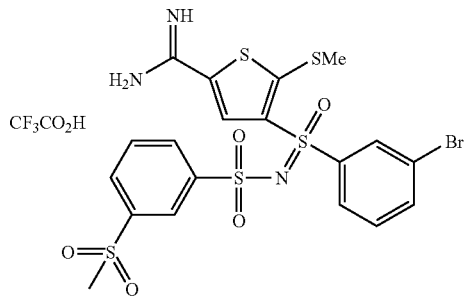

The title compound was prepared following the same procedure described for Example 37. Reaction of 4-[S-(3-bromophenyl)-sulfoxamino]-5-methylsulfanyl-thiophene-2-carbamic acid tert-butyl ester (33 mg, 0.066 mmol, as prepared in Example 24: step j), 3-methanesulfonyl-benzenesulfonyl chloride (88 mg, 0.35 mmol, as prepared in Example 45: step a), and 2,6-lutidine (500 μL) in THF (2 mL), followed by analogous work up and purification as described in Example 38: step b, provided 2.5 mg of the title compound 4-[S-(3-bromophenyl)-N-(sulfonyl-3-methanesulfonyl benzene)-sulfoxamino]-5-methylsulfanyl-thiophene-2-carboxamidine trifluoroacetate. $^1$H-NMR (CD$_3$OD): δ 8.34-8.36 (m, 2H), 8.19-5-8.24 (m, 2H), 8.17 (t, 1H, J=1.9 Hz), 8.05 (ddd, 1H, J=8.1, 1.9, 0.9 Hz), 7.96 (ddd, 1H, J=8.0, 1.9, 0.9 Hz), 7.83 (t, 1H, J=7.9 Hz), 7.59 (t, 1H, 8.1 Hz), 3.19 (s, 3H), and 2.69 (s, 3H). ESI-MS (m/z): Calcd. for $C_{19}H_{18}BrN_3O_5S_5$: 607.9 (M+1); found: 607.9.

EXAMPLE 46

4-[S-[3-(4-guanidino-6-methyl-phenyl)phenyl]-N-(3-nitro benzene-sulfonyl)sulfoximino]-5-methylsulfanyl-thiophene-2-carboxamidine bistrifluoroacetate

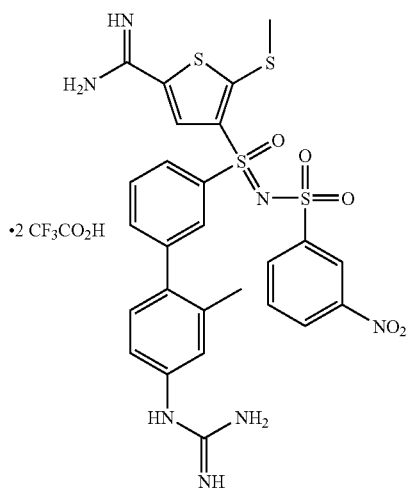

EXAMPLE 46a

2'-Methyl-4'-nitro-biphenyl-3-sulfinic acid methyl ester

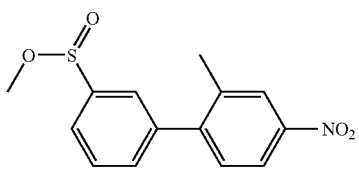

A solution of 3-bromobenzene methyl sulfinate (541 mg, 2.3 mmol), 4,4,5,5-tetramethyl-2-(2-methyl-4-nitro-phenyl)-[1,3,2]dioxaborolane (484 mg, 1.84 mmol), cesium carbonate (900 mg, 2.76 mmol), and Pd(dppf)Cl$_2$ (145 mg, 0.18 mmol) was stirred in DMF at 80° C. for 4 h under argon. The mixture was partitioned between EtOAc (100 mL) and aq NH$_4$Cl (30 mL) and the layers were separated. The organic layer was further washed with water (4×30 mL), brine (30 mL), and was dried over Na$_2$SO$_4$. Concentration of the solution followed by purification of the residue via silica gel chromatography (2-10% EtOAc in hexanes) yielded the product as a colorless oil (300 mg, 56%). $^1$H NMR (CDCl$_3$): δ 8.19 (m, 1H), 8.12 (ddd, 1H, J=0.6, 2.5, 8.4 Hz), 7.77 (ddd, 1H, J=1.2, 1.8, 7.8 Hz), 7.65-7.71 (m, 2H), 7.54 (ddd, 1H, J=1.2, 1.8, 7.6 Hz), 7.41 (d, 1H, J=8.4 Hz), 6.65 (s, 1H), 3.58 (s, 3H), 2.38 (s, 3H).

EXAMPLE 46b

4'-tert-Butoxycarbonylamino-2'-methyl-biphenyl-3-sulfinic acid methyl ester

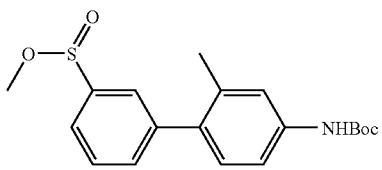

A mixture of 2'-methyl-4'-nitro-biphenyl-3-sulfinic acid methyl ester (Example 46, step a 200 mg, 0.69 mmol)) and palladium (10% on carbon, 100 mg) in MeOH (10 mL) was stirred under a hydrogen atmosphere (1 atm via balloon) for 2 h. Di-tert-butyl dicarbonate (358 mg, 1.24 mmol) was added and the reaction was stirred for 3 h at RT. The mixture was filtered through celite and then was partitioned between EtOAc (100 mL) and water (30 mL). The layers were separated and the organic layer was further washed with water (4×30 µL), brine (30 mL), and was dried over Na$_2$SO$_4$. Concentration of the solution followed by purification of the residue via silica gel chromatography (5-10% EtOAc in hexanes) yielded the product as a colorless oil (191 mg, 77%). $^1$H NMR(CDCl$_3$): δ7.68 (ddd, 1H, J=1.2, 1.6, 7.6 Hz), 7.66 (m, 1H), 7.60 (dt, 1H, J=0.6, 7.6 Hz), 7.51 (ddd, 1H, J=1.2, 1.6, 7.6 Hz), 7.37 (br s, 1H), 7.24 (dd, 1H, J=2.2, 8.4 Hz), 7.17 (d, 1H, J=8.2 Hz), 6.57 (br s, 1H), 3.56 (s, 3H), 2.26 (s, 3H), 1.51 (s, 9H). $C_{19}H_{23}NO_4S$: 362.1 (M+1) found: 262.0 ((M+1)-Boc).

EXAMPLE 46c

[3'-(2-Chloro-5-cyano-thiophene-3-sulfinyl)-biphenyl-4-yl]-carbamic acid tert-butyl ester

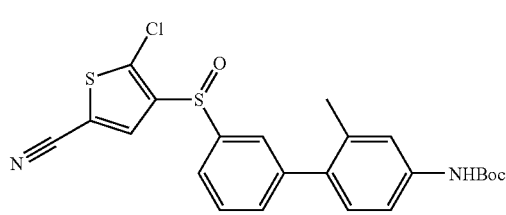

To a solution of 4'-tert-Butoxycarbonylamino-2'-methyl-biphenyl-3-sulfinic acid methyl ester in THF (Example 46, step b 350 mg, 0.97 mmol) was added a solution of 4-(5-chloro-thiophene-2-carbonitrile) magnesium chloride (prepared as in Example 24: step e, 0.5M, 2 mL, 1 mmol) at −78° C. The solution was allowed to warm to −20° C. over 30 min. Additional 4-(5-chloro-thiophene-2-carbonitrile) magnesium chloride (4 mL) was added, the solution was stirred for 1 h, and an additional amount of thiophene-grignard was added (2 mL). After stirring at −20 for 1 h, the reaction was quenched with NaHCO$_3$ (30 mL), and EtOAc (80 mL) was added. The layers were separated and the organic layer was washed with water (2×30 mL), brine (40 mL), and was dried over Na$_2$SO$_4$. The solution was concentrated in vacuo and the residue was purified by silica gel flash chromatography to yield the product (380 mg, 83%). $^1$H NMR (CDCl$_3$): δ 7.66 (ddd, 1H, J=1.4, 1.8, 7.6 Hz), 7.65 (s, 1H), 7.60 (t, 1H, J=1.6 Hz), 7.57 (t, 1H, J=7.6 Hz), 7.47 (dt, 1H, J=1.4, 7.6 Hz), 7.36 (br s, 1H), 7.22 (dd, 1H, J=2.2, 8.4 Hz), 7.13 (d, 1H, J=8.4 Hz), 6.51 (br s, 1H), 2.22 (s, 3H), 1.53 (s, 9H). $C_{19}H_{23}NO_4S$: 362.1 (M+1) found: 262.0 ((M+1)-Boc). $C_{23}H_{21}ClN_2O_3S_2$: 473.1 (M+1) found: 417.0 ((M+1)-tBu), 373.0 ((M+1)-Boc).

EXAMPLE 46d

4-[S-[3-(4-carbamic acid tert-butyl ester-6-methyl phenyl)phenyl]-N-3-nitro phenyl sulfoximino]-5-chloro-thiophene-2-carbonitrile

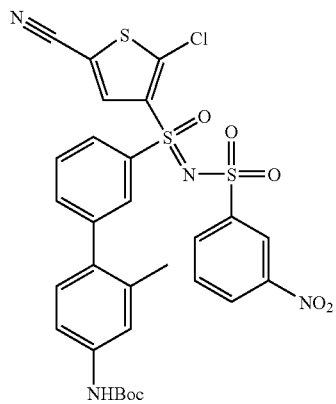

To a suspension of [3'-(2-Chloro-5-cyano-thiophene-3-sulfinyl)-biphenyl-4-yl]-carbamic acid tert-butyl ester (Example 46, step c 380 mg, 0.8 mmol) and 3-nitrophenylsulfonyl-iodinane (646 mg, 1.6 mmol) in acetonitrile (4 mL) was added copper (II) triflate (58 mg, 016 mmol). The reaction was stirred for 5 min and the reaction turned brown. TLC analysis indicated that a decomposition might be occurring so the reaction was quenched with aq NaHCO₃ (2 mL). The solution was partitioned between EtOAc (100 mL) and NaHCO₃ (30 mL) and the layers were separated. The organic layer was washed with water (3×20 μL) and brine (30 mL). The organic solution was dried over Na₂SO₄, concentrated in vacuo, and the residue was purified via silica gel flash chromatography to yield the product (156 mg, 14%). ¹H NMR (CDCl₃): δ 8.84 (t, 1H, J=1.8 Hz), 8.42 (ddd, 1H, J=1.0, 2.2, 8.2 Hz), 8.34 (ddd, 1H, J=1.0, 1.6, 7.8 Hz), 8.06 (s, 1H), 8.02 (m, 1H), 8.00 (m, 1H), 7.74 (t, 1H, J=8.1 Hz), 7.67 (m, 1H), 7.39 (br s, 1H), 7.26 (dd, 1H, J=2.2, 8.2 Hz), 7.11 (d, 1H, J=8.2 Hz), 6.63 (br s, 1H), 2.22 (s, 3H), 1.54 (s, 9H). $C_{19}H_{23}NO_4S$: 362.1 (M+1) found: 262.0 ((M+1)-Boc).

EXAMPLE 46e

4-[S-[3-(4-guanidino-6-methyl-phenyl)phenyl]-N-3-nitro phenyl sulfoximino]-5-chloro-thiophene-2-carbonitrile

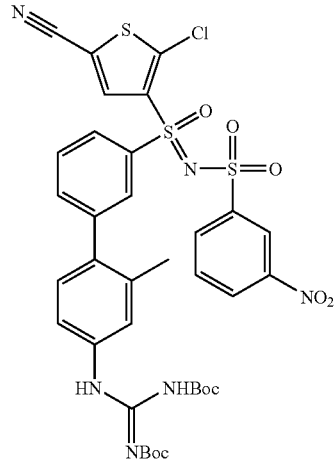

To a solution of 4-[S-[3-(4-carbamic acid tert-butyl ester-6-methyl phenyl)phenyl]-N-3-nitro phenyl sulfoximino]-5-chloro-thiophene-2-carbonitrile (Example 46, step d 46 mg, 0.068 mmol) in DCM (2 mL) was added TFA (2 mL) and the solution was stirred for 30 min at RT. The solvent was removed in vacuo and the residue was taken up in EtOAc (23 mL). The organic layer was washed with NaHCO₃ (2×10 mL), brine (10 mL), and was dried over Na₂SO₄. The solvent was evaporated in vacuo and a portion of the residue (30 mg, 0.52 mmol) was dissolved in DCM (5 mL) and cooled to 0° C. Mercuric (II) chloride (41 mg, 0.15 mmol) was added followed by dropwise addition of 1,3-Bis(tert-butoxycarbonyl)2-methyl-2-thiopseudourea (0.25M in DCM, 250 uL, 0.63 mmol). The reaction warmed to RT over 30 min and was complete by TLC analysis. The solution was transferred to a silica gel column and was eluted with a 5-20% gradient of EtOAc in hexanes to yield the product (36 mg, 84%). $C_{35}H_{35}ClN_6O_9S_3$: 815.1 (M+1); found: 814.6.

EXAMPLE 46f

4-[S-[3-(4-guanidino-6-methyl-phenyl)phenyl]-N-(3-nitro benzene-sulfonyl)sulfoximino]-5-methylsulfanyl-thiophene-2-carboxamidine bistrifluoroacetate

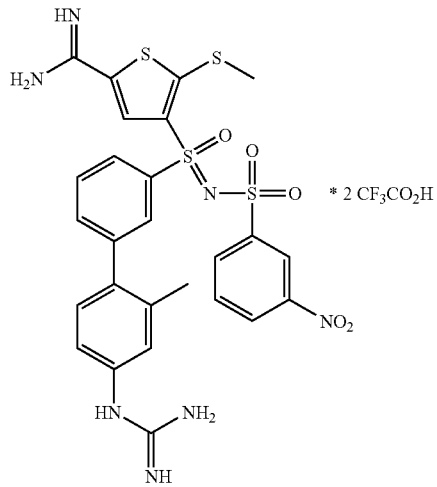

To a solution of 4-[S-[3-(4-guanidino-6-methyl-phenyl) phenyl]-N-3-nitro phenyl sulfoximino]-5-chloro-thiophene-2-carbonitrile (Example 46, step e; 36 mg, 0.044 mmol) in THF at −78° C. was added a solution of NaSMe (0.25M, 528 uL, 0.132 mmol) in MeOH. The reaction was allowed to warm to RT over 30 min and was stirred for an additional hr at RT. Ethyl acetate (30 mL) and aqueous NaHCO$_3$ (10 mL) were added and the layers were separated. The organic layer was washed with water (10 mL), brine (10 mL), and was dried over Na$_2$SO$_4$. The solution was concentrated and the residue was dissolved in methanolic ammonia (7N, 20 mL). Ammonium formate (500 mg) was added and the reaction was heated at 40° C. for 12 h. The solution was concentrated and the residue was dissolved in 1:1 TFA/DCM (10 mL). After stirring for 1 h at RT, the solution was concentrated and the resulting residue was purified by RP-HPLC (10-55% acetonitrile in 0.1% TFA/water over 40 min.) to afford the title compound (6 mg, 26%) as a colorless glassy solid. $^1$H NMR (CD$_3$OD): δ $^1$H NMR (CD$_3$OD): δ 8.61 (m, 1H), 8.48 (ddd, 1H, J=1.0, 2.3, 8.2 Hz), 8.43 (s, 1H), 8.30 (ddd, 1H, J=1.0, 1.8, 7.9 Hz), 8.08 (m, 1H), 8.02 (m, 1H), 7.83 (t, 1H, J=8.1 Hz), 7.77 (m, 1H), 7.73 (m, 1H), 7.35 (d, 1H, J=8.1 Hz), 7.29 (m, 1H), 7.24 (m, 1H), 2.70 (s, 3H), 2.29 (s, 3H). C$_{26}$H$_{25}$N$_7$O$_5$S$_4$: 644.1 (M+1); found: 644.0.

EXAMPLE 47

[3-Methyl-2-(4,4,5,5-tetramethyl-[1,3,2]dioxaborolan-2-yl)-5-(2-trimethylsilanyl-ethoxycarbonylamino)-phenyl]-carbamic acid 2-trimethylsilanyl-ethyl ester To a 0° C. solution of [3-Methyl-2-(4,4,5,5-tetramethyl-[1,3,2]dioxaborolan-2-yl)-5-(2-trimethylsilanyl-ethoxycarbonylamino)-phenyl]-carbamic acid 2-trimethylsilanyl-ethyl ester (synthesis described in WO03099805) 195 mg, 0.5 mmol) and pyridine (200 uL, 2.5 mmol) in DCM (10 mL) was added a solution of trimethylsilylethyl chloroformate (0.4 M in toluene, 1.5 mL, 0.6 mmol) over 5 min. After stirring for 30 min, ethyl acetate (80 mL) and aqueous NaHCO$_3$ (20 mL) were added and the layers were separated. The organic layer was washed with aqueous citric acid (3×20 mL), aqueous NaHCO$_3$ (20 mL), brine (20 mL), and was dried over Na$_2$SO$_4$. The solution was concentrated in vacuo and the residue was purified via silica gel flash chromatography (5-15% EtOAc in hexanes) yielding the product (190 mg, 71%) as an oil. $^1$H NMR (CDCl$_3$): δ 9.18 (s, 1H), 7.93 (d, 1H, J=2.0 Hz), 7.27 (br s, 1H), 6.62 (s, 1H), 4.27 (m, 2H), 4.09 (m, 4H), 2.50 (s, 3H), 1.37 (s, 9H), 1.06 (m, 4H), 0.09 (s, 9H), 0.07 (s, 9H).

EXAMPLE 48

4-[S-([6-Methyl-4-(2-trimethylsilanyl-ethoxycarbonylamino)-biphenyl-2-yl]-carbamic acid 2-trimethylsilanyl-ethyl ester)-N-sulfony-4-analine sulfoximino]-5-methylsulfanyl-thiophene-2-carbamic acid tert-butyl ester The procedure outlined in Example 18, step c was followed using 4-[S-(3-Bromophenyl)-N-sulfonyl-3-analine sulfoximino]-5-methylsulfanyl-thiophene-2-carbamic acid tert-butyl ester (Example 33: step b; 101 mg, 0.16 mmol), [3-Methyl-2-(4,4,5,5-tetramethyl-[1,3,2]dioxaborolan-2-yl)-5-(2-trimethylsilanyl-ethoxycarbonylamino)-phenyl]-carbamic acid 2-trimethylsilanyl-ethyl ester (190 mg, 0.35 mmol), and saturated NaHCO$_3$ (2 mL), tetrakis(triphenylphosphine)palladium (0) (60 mg, 0.054 mmol), and dimethoxyethane (4 mL). Analogous purification yielded the product (78 mg, 50%). $^1$H NMR (CDCl$_3$): δ 7.9-8.05 (m, 3H), 7.69 (m, 1H), 7.67 (m, 1H), 7.60 (m, 1H), 7.44 (m, 1H), 7.28 (br s, 1H), 6.72 (m, 1H), 6.57 (m, 2H), 6.08 (br m, 1H), 4.28 (m, 2H), 4.10 (m, 2H), 2.52 (br d, 3H), 1.93 (br d, 3H), 1.52 (s, 9H), 1.08 (m, 2H), 0.92 (m, 2H), 0.08 (s, 9H), −0.02 (br d, 9H). C$_{42}$H$_{58}$N$_6$O$_9$S$_4$Si$_2$: 975.3 (M+1); found: 932.8 ((M+1)-CO$_2$).

EXAMPLE 49

Tablet Preparation

Tablets containing 25.0, 50.0, and 100.0 mg, respectively, of an active compound are prepared as illustrated below:

| TABLET FOR DOSES CONTAINING FROM 25-100 MG OF THE ACTIVE COMPOUND | | | |
|---|---|---|---|
| | Amount-mg | | |
| Active Compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the cornstarch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 50

Intravenous Solution Preparation

An intravenous dosage form of the above-indicated active compounds is prepared as follows:

| | |
|---|---|
| Active Compound | 0.5-10.0 mg |
| Sodium Citrate | 5-50 mg |
| Citric Acid | 1-15 mg |
| Sodium Chloride | 1-8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

EXAMPLE 51

In Vitro Inhibition of C1s

Reagents: All buffer salts were obtained from Sigma Chemical Company (St. Louis, Mo.), and were of the highest purity available. DTNB was purchased from Pierce (Rockford, Ill.). Z-Gly-Arg-S-Bzl was purchased from Enzyme Systems Products (Livermore, Calif.). Activated human C1s was purchased from Calbiochem (La Jolla, Calif.).

$K_i$ Determinations: All assays were based on the ability of the test compound to inhibit the C1s-catalyzed hydrolysis of the substrate Z-Gly-Arg-S-Bzl, which was observed via a secondary reaction with 5,5'-dithio-bis(2-nitrobenzoic acid) (DTNB). In a typical $K_i$ determination, substrate was prepared in DMSO, and diluted into an assay buffer consisting of 50 mM HEPES, 200 mM NaCl, pH 7.5, 0.05% n-octyl-β-D-glucopyranoside. Substrate solutions were prepared at a concentration of 45 µM ($K_m$=190 µM) with DTNB at a concentration of 200 µM in assay buffer. Test compounds were prepared as a 10 µM solution in DMSO. Dilutions were prepared in DMSO yielding 7 final concentrations encompassing a 700-fold concentration range. Purified activated C1s was diluted into assay buffer for a working concentration of 66 nM.

In a typical $K_i$ determination, into each well of a 96-well plate was pipetted 280 µL of substrate solution, 10 µL of test compound solution, and the plate allowed to thermally equilibrate at 37° C. for 15 minutes. Reactions were initiated by the addition of a 10 µL aliquot of the enzyme, and the absorbance increase at 405 nm was continuously recorded for 15 minutes in a Molecular Devices plate reader. Final DMSO concentration was 4.3%. Final reagent concentrations were: [C1s]=2.3 nM, [Z-Gly-Arg-S-Bzl]=45 µM, [DTNB]=200 µM. The ratio of the velocity (rate of change in absorbance as a function of time) for a sample containing no test compound was divided by the velocity of a sample containing test compound, and was plotted as a function of test compound concentration. The data were fit to a linear regression, and the value of the slope of the line calculated. The inverse of the slope was the experimentally determined $K_i$ value.

EXAMPLE 52

In Vitro Inhibition of MASP-2

Reagents: All buffer salts were obtained from Sigma Chemical Company (St. Louis, Mo.), and were of the highest purity available. DTNB was purchased from Pierce (Rockford, Ill.). Z-Gly-Arg-S-Bzl was purchased from Enzyme Systems Products (Livermore, Calif.). Autoactivated 2-chain human MASP-2 (His-tag, Cys300-Phe686) was produced in-house from a Baculovirus expression system in insect cells.

$K_i$ Determinations: All assays were based on the ability of the test compound to inhibit the MASP-2-catalyzed hydrolysis of the substrate Z-Gly-Arg-S-Bzl, which was observed via a secondary reaction with 5,5'-dithio-bis(2-nitrobenzoic acid) (DTNB). In a typical $K_i$ determination, substrate was prepared in DMSO, and diluted into an assay buffer consisting of 50 mM HEPES, 200 mM NaCl, pH 7.5, 0.05% n-octyl-β-D-glucopyranoside. Substrate solutions were prepared at a concentration of 45 µM ($K_m$=8.6 µM) with DTNB at a concentration of 200 µM in assay buffer. Test compounds were prepared as a 10 µM final concentration in assay buffer. Dilutions of test compounds were prepared in assay buffer yielding at least 7 final concentrations encompassing a 700-fold concentration range. Purified activated MASP-2 was diluted into assay buffer for a working concentration of 30 nM.

In a typical $K_i$ determination, into each well of a 96-well plate was pipetted 280 µL of substrate solution followed by 10 µL of test compound solution, and the plate was allowed to thermally equilibrate at 37° C. for 10 minutes. Reactions were initiated by the addition of a 10 µL aliquot of the enzyme, and the absorbance increase at 405 nm was continuously recorded for 15 minutes in a Molecular Devices plate reader. Final reagent concentrations were: [MASP-2] =1.0 nM, [Z-Gly-Arg-S-Bzl]=45 µM, [DTNB]=200 µM. The ratio of the velocity (rate of change in absorbance as a function of time) for a sample containing no test compound was divided by the velocity of a sample containing test compound, and was plotted as a function of test compound concentration. The data were fit to a linear regression, and the value of the slope of the line calculated. The inverse of the slope was the experimentally determined apparent $K_i$ value ($K_i$ app). The $K_i$ app was corrected for true $K_i$ from the relationship between the substrate concentration [S] and the substrate Km, where $K_i = K_i$ app $\times(1/(1+[S]/Km))$.

Complement Inhibition Data

The following compounds have Ki values in the range of 0.008 to 6.0 micromolar (µM) for C1s: Examples 3-22, 25-28, 30-46.

The compound of Example 46 has a Ki value of 0.010 µM for C1s. The compound of Example 18 has a Ki value of 0.011 µM for C1s and 0.44 µM for MASP-2. The results indicate that the compounds of the present invention are inhibitors of complement, specifically C1s.

It will be understood to those of ordinary skill in the art that the invention as described herein can be performed within a wide and equivalent range of conditions, formulations, and other parameters without affecting the scope of the invention or any embodiment thereof. All patents and publications cited herein are fully incorporated by reference into this text in their entirety.

We claim:

1. A racemic or homochiral compound of Formula I:

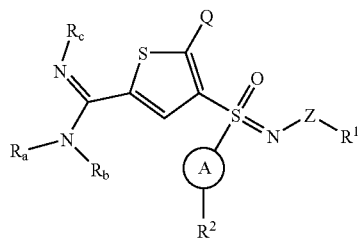

or a solvate, hydrate, pharmaceutically acceptable salt, or prodrug thereof; wherein:

Z is —CO—, —SO$_2$—, —SO$_2$CH$_2$—, —COCH$_2$—, —CONH—, or a direct bond wherein the carbonyl carbon or the sulfur is bonded to the nitrogen;

Q is C$_{1-4}$ alkyl, halo, amino, C$_{1-6}$ alkylthio, C$_{2-6}$ alkenylthio, C$_{1-6}$ alkoxy, trifluoromethyl, methylsulfonyl, or benzylthio;

R$^1$ is hydrogen, C$_{1-4}$ alkyl, or aryl, any of which except hydrogen is optionally substituted with one or two substituents independently selected from: guanidinyl, halogen, —CF$_3$, —CN, —NO$_2$, —NR$_d$COR$_e$, —CONR$_d$R$_e$, —NR$_d$SO$_2$R$_e$, —SO$_2$NR$_d$R$_e$, —NR$_d$CONHR$_e$, —R$_d$, —NR$_d$R$_e$, —CO$_2$R$_d$, or —SO$_2$R$_d$;

R$^2$ is hydrogen, halogen, or aryl, wherein the aryl is optionally substituted with up to three substituents independently selected from the group consisting of: C(1-4)alkyl, —NR$_f$R$_g$, and guanidinyl;

A is aryl; and

R$_a$, R$_b$, R$_c$, R$_d$, R$_e$, R$_f$ and R$_g$ are independently hydrogen, C$_{1-4}$ alkyl, C$_{6-10}$ aryl, C$_{1-4}$ hydroxyalkyl, C$_{1-4}$ aminoalkyl, mono (C$_{1-4}$)alkylamino(C$_{2-6}$)alkyl, di(C$_{1-4}$)alkylamino(C$_{2-6}$)alkyl, carboxy(C$_{1-4}$)alkyl, cyano, nitro, amino, C$_{1-4}$ alkoxy, hydroxy, or —CO$_2$R$^w$, wherein R$^w$ is hydrogen, hydroxy, C$_{1-4}$ alkoxy, cyano, C$_{1-4}$ alkoxycarbonyl, C$_{1-4}$ alkyl, C$_{3-8}$ cycloalkyl, phenyl, or benzyl.

2. A compound of claim 1, wherein:
Q is —SC$_{(1-4)}$alkyl; and
A is phenyl.

3. A compound of claim 1, wherein:
Q is —SC$_{(1-4)}$alkyl;
A is phenyl; and
R$^1$ is hydrogen, C$_{1-4}$ alkyl, or aryl, any of which except hydrogen is optionally substituted with one or two substituents independently selected from: guanidinyl, halogen, —CF$_3$, —CN, —NO$_2$, —NR$_d$COR$_e$, NR$_d$SO$_2$R$_e$, NR$_d$CONHR$_e$, R$_d$, NH$_2$, CO$_2$R$_e$, or SO$_2$R$_d$.

4. A compound of claim 1, wherein:
Q is —SC$_{(1-4)}$alkyl;
A is phenyl;
R$_a$, R$_b$, and R$_c$ are hydrogens; and
R$^1$ is hydrogen, C$_{1-4}$ alkyl, or phenyl, any of which except hydrogen is optionally substituted with one or two substituents independently selected from: guanidinyl, halogen, —CF$_3$, —CN, —NO$_2$, NR$_d$COR$_e$, NR$_d$SO$_2$R$_e$, NR$_d$CONHR$_e$, R$_d$, NH$_2$, CO$_2$R$_e$, or SO$_2$R$_d$.

5. A compound selected from the group consisting of the following:

4-[S-(3-Bromophenyl)-N-(2-nitrobenzene-sulfonyl)sulfoxamino]-5-methylsulfanyl-thiophene-2-carboxamidine trifluoroacetate;

4-[S-(3-Bromophenyl)-N-(3-acetamidobenzene-sulfonyl)sulfoxamino]-5-methylsulfanyl-thiophene-2-carboxamidine trifluoroacetate;

4-[S-(3-Bromophenyl)-N-(3-{N,N-bismethanesulfonyl}aminobenzene-sulfonyl)sulfoxamino]-5-methylsulfanyl-thiophene-2-carboxamidine trifluoroacetate;

4-[S-(3-Bromophenyl)-N-(3-ureidobenzene-sulfonyl)sulfoxamino]-5-methylsulfanyl-thiophene-2-carboxamidine trifluoroacetate;

4-[S-(3-Bromophenyl)-N-(3-methanesulfonamidobenzene-sulfonyl)sulfoxamino]-5-methylsulfanyl-thiophene-2-carboxamidine trifluoroacetate;

4-[S-(3-Bromo-benzenesulfonyl)-N-(m-sulfonyl benzoic acid)-sulfoxamino]-5-methylsulfanyl-thiophene-2-carboxamidine trifluoroacetate;

4-[S-(3-Bromo-benzenesulfonyl)-N-(p-sulfonyl benzoic acid)-sulfoxamino]-5-methylsulfanyl-thiophene-2-carboxamidine trifluoroacetate;

4-[S-(3-Bromophenyl)-N-Tosylsulfoximino]-5-methylsulfanyl-thiophene-2-carboxamidine trifluoroacetate;

5-Bromo-4[S-(3-Bromophenyl)-N-Tosylsulfoximino]-thiophene-2-carboxamidine trifluoroacetate;

4-[S-(3-Bromophenyl)-N-Tosylsulfoximino]-5-methylsulfanyl-thiophene-2-amidine trifluoroacetate;

4-[S-(3-Bromophenyl)-N-sulfonyl-3-nitro-benzene sulfoximino]-5-methylsulfanyl-thiophene-2-amidine trifluoroacetate;

4-[S-(3-Bromophenyl)-N-sulfonyl-4-aminophenylsulfoximino]-5-methylsulfanyl-thiophene-2-amidine trifluoroacetate;

4-[S-(3-Bromophenyl)-N-sulfonyl-3-analine sulfoximino]-5-methylsulfanyl-thiophene-2-amidine trifluoroacetate;

4-[S-(3-Bromophenyl)-N-(sulfonyl-3-phenylcarbonitrile)-sulfoxamino]-5-methylsulfanyl-thiophene-2-carboxamidine trifluoroacetate;

4-[S-(3-Bromophenyl)-N-(sulfonyl-3-benzamide)-sulfoxamino]-5-methylsulfanyl-thiophene-2-carboxamidine trifluoroacetate;

4-[S-(3-Bromophenyl)-N-(sulfonyl-3-trifluoromethyl-benzene)-sulfoxamino ]-5-methylsulfanyl-thiophene-2-carboxamidine trifluoroacetate;

4-[S-(3-Bromophenyl)-N-(sulfonyl-2-methyl-5-nitro-benzene)-sulfoxamino]-5-methylsulfanyl-thiophene-2-carboxamidine trifluoroacetate;

4-[S-(3-Bromophenyl)-N-(sulfonyl-5-methanesulfonyl-2-methyl-benzene)-sulfoxamino]-5-methylsulfanyl-thiophene-2-carboxamidine trifluoroacetate;

4-[S-(3-Bromophenyl)-N-(sulfonyl-3-guanidinobenzene)-sulfoxamino]-5-methylsulfanyl-thiophene-2-carboxamidine bistrifluoroacetate; and 4-[S-(3-Bromophenyl)-N-(sulfonyl-3-methanesulfonyl benzene)-sulfoxamino]-5-methylsulfanyl-thiophene-2-carboxamidine trifluoroacetate.

6. A compound which is:

4-[S-(3-Bromophenyl)-N-p-tolyl-formamide]-5-methylsulfanyl-thiophene-2-carboxamidine trifluoroacetate.

7. A compound selected from the group consisting of the following:
- 4-[S-(3-Bromophenyl)-N-benzamide]-5-methylsulfanyl-thiophene-2-carboxamidine trifluoroacetate;
- 4-[S-(3-Bromophenyl)-N-3-nitro-benzamide]-5-methyl-sulfanyl-thiophene-2-carboxamidine trifluoroacetate; and
- 4-[S-(3-Bromophenyl)-N-3-amino-benzamide]-5-methylsulfanyl-thiophene-2-carboxamidine trifluoroacetate.

8. A compound selected from the group consisting of the following:
- 4-[S-(3-Bromophenyl)-N-(phenylmethane-sulfonyl) sulfoxamino]-5-methylsulfanyl-thiophene-2-carboxamidine trifluoroacetate;
- 4-[S-(3-Bromophenyl)-N-(methanesulfonyl)-sulfoxamino]-5-methylsulfanyl-thiophene-2-carboxamidine trifluoroacetate; and
- 4-[S-(3-Bromophenyl)-N-({2-aminophenyl}methanesulfonyl)sulfoxamino]-5-methylsulfanyl-thiophene-2-carboxamidine trifluoroacetate.

9. A compound selected from the group consisting of the following:
- 4-[S-[3-(2-Amino-4-guanidino-6-methyl-phenyl)phenyl]-N-(3-ureidobenzene-sulfonyl)sulfoxamino]-5-methylsulfanyl-thiophene-2-carboxamidine bistrifluoroacetate;
- 4-[S-[3-(2-Tolylphenyl)phenyl]-N-Tosylsulfoximino]-5-methylsulfanyl-thiophene-2-carboxamidine trifluoroacetate;
- 4-[S-[3-(2-amino-4-guanidino-6-methyl-phenyl)phenyl]-N-(4-ureidobenzene-sulfonyl)sulfoxamino]-5-methylsulfanyl-thiophene-2-carboxamidine bistrifluoroacetate; and
- 4-[S-[3-(4-guanidino-6-methyl-phenyl)phenyl]-N-(3-nitrobenzene-sulfonyl)sulfoximino]-5-methylsulfanyl-thiophene-2-carboxamidine bistrifluoroacetate.

10. A compound selected from the group consisting of the following:
- 4-[S-(3-Bromophenyl)-N-(phenyl)-sulfoxamino]-5-methylsulfanyl-thiophene-2-carboxamidine trifluoroacetate;
- 4-[S-(3-Bromophenyl)-sulfoximino]-5-methylsulfanyl-thiophene-2-carbamic acid tert-butyl ester; and
- 4-(3-Bromo-benzenesulfoxamine)-5-methylsulfanyl-thiophene-2-carboxamidine.

11. A compound which is:
- 4-(3-Bromo-benzenesulfoxamineacetamide)-5-methylsulfanyl-thiophene-2-carboxamidine.

12. A pharmaceutical composition, comprising a compound of claim 1 and a pharmaceutically-acceptable carrier or diluent.

* * * * *